US011413270B2

(12) United States Patent
Lee et al.

(10) Patent No.: US 11,413,270 B2
(45) Date of Patent: Aug. 16, 2022

(54) METHOD FOR THE TREATMENT OF PANCREATITIS

(71) Applicant: NOVMETAPHARMA CO., LTD., Seoul (KR)

(72) Inventors: Heon Jong Lee, Incheon-si (KR); Hoe Yune Jung, Pohang-si (KR); In-Kyu Lee, Daegu (KR); Jae-Han Jeon, Daegu (KR); Sung Jin Cho, Daegu (KR)

(73) Assignee: NOVMETAPHARMA CO., LTD., Seoul (KR)

( * ) Notice: Subject to any disclaimer, the term of this patent is extended or adjusted under 35 U.S.C. 154(b) by 0 days.

(21) Appl. No.: 16/908,195

(22) Filed: Jun. 22, 2020

(65) Prior Publication Data

US 2021/0393583 A1 Dec. 23, 2021

(51) Int. Cl.
| | | |
|---|---|---|
| *A61K 31/397* | (2006.01) | |
| *A61K 31/495* | (2006.01) | |
| *A61K 31/4453* | (2006.01) | |
| *A61K 31/5375* | (2006.01) | |
| *A61K 31/4025* | (2006.01) | |
| *A61P 1/18* | (2006.01) | |
| *A61K 31/454* | (2006.01) | |
| *A61K 31/407* | (2006.01) | |
| *A61K 31/4525* | (2006.01) | |
| *A61K 31/403* | (2006.01) | |
| *A61K 31/4192* | (2006.01) | |
| *A61K 31/396* | (2006.01) | |

(52) U.S. Cl.
CPC .......... *A61K 31/397* (2013.01); *A61K 31/396* (2013.01); *A61K 31/403* (2013.01); *A61K 31/407* (2013.01); *A61K 31/4025* (2013.01); *A61K 31/4192* (2013.01); *A61K 31/4453* (2013.01); *A61K 31/454* (2013.01); *A61K 31/4525* (2013.01); *A61K 31/495* (2013.01); *A61K 31/5375* (2013.01); *A61P 1/18* (2018.01)

(58) Field of Classification Search
CPC .................................................. A61K 31/397

USPC ..................................................... 514/210.01
See application file for complete search history.

(56) References Cited

U.S. PATENT DOCUMENTS

| | | | |
|---|---|---|---|
| 6,875,775 B2 | 4/2005 | Sodervall et al. | |
| 10,934,303 B2 * | 3/2021 | Hwang | ................ A61K 31/397 |
| 2008/0255089 A1 | 10/2008 | Katamreddy | |
| 2019/0167820 A1 | 6/2019 | Hwang et al. | |
| 2020/0078476 A1 | 3/2020 | Hwang et al. | |

FOREIGN PATENT DOCUMENTS

| | | | | |
|---|---|---|---|---|
| KR | 2018001240 | * | 1/2018 | ........... C07D 241/04 |
| KR | WO2018004065 | * | 1/2018 | ........... C07D 241/04 |
| WO | 2018/004065 A1 | | 1/2018 | |

OTHER PUBLICATIONS

Kim, J. Med. Chem. 2016, 59, 10209-10227.*
Misra Trends in Endocrinology & Metabolism, Apr. 2017, vol. 28, No. 4, 2611-272.*
Yoshihara Cell Metab. Apr. 12, 2016; 23(4): 622-634.*
International Search Report dated Sep. 27, 2021 in International Application No. PCT/IB2021/055508.
Written Opinion of the International Searching Authority dated Sep. 27, 2021 in International Application No. PCT/IB2021/055508.
Kim et al., "Synthesis and biological evaluation of novel 4-hydroxytamoxifen analogs as estrogen-related receptor gamma inverse agonists", European Journal of Medicinal Chemistry, 2016, vol. 120, pp. 338-352 (15 pages total).
Lei et al., "Candidate genes mediated by estrogen-related receptor γ in pancreatic β cells", J Biochem Mol Toxicol., 2019, vol. 33, e22390, pp. 1-6 (6 pages total).

* cited by examiner

*Primary Examiner* — Nizal S Chandrakumar
(74) *Attorney, Agent, or Firm* — Sughrue Mion, PLLC

(57) ABSTRACT

A composition for preventing and/or treating pancreatitis and a method of prevention and/or treatment of pancreatitis are disclosed. The composition include an aryl ethene compound, a pharmaceutically acceptable salt thereof, or a solvate thereof, as an active ingredient. The method includes administering the aryl ethene compound, an isomer, a pharmaceutically acceptable salt thereof, or a solvate thereof, in an effective amount to a subject in need thereof.

7 Claims, 8 Drawing Sheets
(2 of 8 Drawing Sheet(s) Filed in Color)
Specification includes a Sequence Listing.

SEQUENCE LISTING

```
<160> NUMBER OF SEQ ID NOS: 6

<210> SEQ ID NO 1
<211> LENGTH: 20
<212> TYPE: DNA
<213> ORGANISM: artificial sequence
<220> FEATURE:
<223> OTHER INFORMATION: Esrra forward primer

<400> SEQUENCE: 1
tacggtgtgg catcctgtga                                               20

<210> SEQ ID NO 2
<211> LENGTH: 20
<212> TYPE: DNA
<213> ORGANISM: Artificial Sequence
<220> FEATURE:
<223> OTHER INFORMATION: Essr reverse primer

<400> SEQUENCE: 2
ctcccctgga tggtcctctt                                               20

<210> SEQ ID NO 3
<211> LENGTH: 18
<212> TYPE: DNA
<213> ORGANISM: Artificial sequence
<220> FEATURE:
<223> OTHER INFORMATION: Esrrg forward primer

<400> SEQUENCE: 3
gcccagccac gaatgaat                                                 18
```

```
<210> SEQ ID NO 4
<211> LENGTH: 18
<212> TYPE: DNA
<213> ORGANISM: Artificial sequence
<220> FEATURE:
<223> OTHER INFORMATION: Esrrg reverse primer

<400> SEQUENCE: 4
gcaggcctgg caggattt                                                 18

<210> SEQ ID NO 5
<211> LENGTH: 20
<212> TYPE: DNA
<213> ORGANISM: Artificial sequence
<220> FEATURE:
<223> OTHER INFORMATION: 36b4 forward primer

<400> SEQUENCE: 5
acctccttct tccaggcttt                                               20

<210> SEQ ID NO 6
<211> LENGTH: 20
<212> TYPE: DNA
<213> ORGANISM: Artificial sequence
<220> FEATURE:
<223> OTHER INFORMATION: 3664 reverse primer

<400> SEQUENCE: 6
ctccagtctt tatcagctgc                                               20
```

METHOD FOR THE TREATMENT OF PANCREATITIS

STATEMENT OF GOVERNMENT INTEREST

A study described in this application was supported by a grant of the Daegu-Gyeongbuk/Osong Medical Cluster R&D Project funded by the Ministry of Science and ICT, the Ministry of Trade, Industry and Energy, the Ministry of Health & Welfare, Republic of Korea (Grant Number: HI19C0760).

FIELD

This disclosure includes methods and compositions for the treatment of acute pancreatitis. In an aspect, the disclosure concerns the use of a molecule to reduce or prevent the secretion of pancreatic digestive enzymes within the pancreas. This molecule serves to prevent mitochondrial dysfunction and autophagic dysfunction in pancreatic acinar cells which leads to prevention of immature activation of pancreatic digestive enzymes and autodigestion of the pancreas. The disclosure is also concerned with methods of treating a mammal suffering from pancreatitis through the administration of this molecule.

BACKGROUND

In mammals, the pancreas, a large gland structurally similar to the salivary gland, contains acinar cells, responsible for digestive enzyme production, and ductal cells, which secrete large amounts of sodium bicarbonate solution. The physiological function of the pancreatic acinar cell is to synthesize, transport, store, and secrete digestive enzymes. This is accomplished through coordinated and sequential actions of the endoplasmic reticulum (ER), Golgi apparatus, the endolysosomal system, storage and secretory organelles, as well as the mitochondria. The combined secretion product is termed as "pancreatic juice"; this liquid flows through the pancreatic duct into the duodenum. The precise composition of pancreatic juice appears to be influenced by the types of compounds (carbohydrate, lipid, protein, and/or nucleic acid) in the chyme.

Pancreatic juice consists of various proteases (trypsin, chymotrypsin, carboxypolypeptidase), nucleases (RNase and DNase), pancreatic amylase, and lipases (pancreatic lipase, cholesterol esterase and phospholipase). Many of these enzymes are initially synthesized by the acinar cells in an inactive form as zymogens, e.g., trypsin is synthesized as trypsinogen. These enzymes are activated in a cascade manner, wherein, initially, trypsin is activated through proteolytic cleavage by the enzyme enterokinase. Trypsinogen can also be autoactivated by trypsin. Trypsin, in turn, activates both chymotypsinogen and procarboxypolypeptidase to form their active protease counterparts. The enzymes are normally activated only when they enter the intestinal mucosa in order to prevent autodigestion of the pancreas. As an in-built counter-mechanism to prevent premature activation, the acinar cells additionally secrete a trypsin inhibitor. This inhibitor prevents premature activation of the proteolytic enzymes within the secretory cells and in the ducts of the pancreas. Subsequently, inhibition of trypsin activity also prevents activation of the other proteases.

Pancreatitis is a serious medical condition involving an inflammation of the pancreas and can occur when an excess amount of trypsin saturates the supply of trypsin inhibitor. Trypsin accumulation in the pancreatic acinar cells can be caused by underproduction of trypsin inhibitor, or the overabundance of trypsin production. In acute or chronic pancreatitis, this precipitates into inflammation which manifests itself in the release and activation of pancreatic enzymes within the organ, thus leading to initiation of pancreatic autodigestion. In many cases of acute pancreatitis, the condition can lead to death. Genetic factors, gallstones, and alcohol abuse are among the major factors that have been associated with the development of pancreatitis. The current paradigm is that pancreatitis is initiated by acinar cell injury, leading to parenchymal necrosis and inflammation, which are the main pathologic features of the disease. It is understood and extensively documented, both scientifically as well as clinically, that chronic pancreatitis (CP) results from repetitive bouts of acute pancreatitis (AP), or can develop without prior AP.

AP is a leading cause for gastrointestinal-related complications in humans, the primary etiologic factor being development of gallstones. Although AP is most commonly mild to moderate in severity, the fatality rate is significantly high (approximately, 1 out of 3) in patients owing to persistent multi-organ dysfunction. Additionally, several studies have demonstrated that patients with hereditary pancreatitis carry mutations in genes encoding for digestive enzymes. However, these patients have been reported to develop recurrent attacks and falls in a high risk group of developing CP rather than severe AP.

As mentioned earlier, AP is believed to be initiated from the damaged pancreatic acinar cells. Digestive enzymes are synthesized, stored and exported from the pancreatic acinar cells upon appropriate stimulus. The synthesis of these enzymes begin in the endoplasmic reticulum and ends with the secretion of proteins which are temporarily stored in zymogen granules. ATP, produced by the mitochondria, is utilized by distinct pancreatic organelles to transport and modify these unprocessed proteins in a sequential manner through several vesicular compartments. As with several other cellular processes, the autophagy-lysosomal-endosomal pathways acts as a checkpoint to maintain acinar cell homeostasis by removing damaged/dysfunctional organelles and recycling cell constituents to be reutilized as source substrate and energy.

In an attempt to investigate and delineate the step-by-step initiation, progression and treatment of this disease, several non-invasive models of experimental acute pancreatitis have been developed. Among them, caerulein (a cholecystokinin-pancreozymin analogue) has been extensively used to successfully induce acute pancreatitis in mammals. Caerulein-induced acute pancreatitis model can be generated by intravenous, subcutaneous or intraperitoneal injection routes in experimental animals. Additionally, caerulein has been successfully used to understand the molecular pathogenesis of pancreatitis in various in vitro models. The structural changes of acinar cells observed in human acute pancreatitis exhibit significant similarities to caerulein-induced acute pancreatitis in mouse. In particular, specific changes to intracellular organelles in the acinar cells were similar in both human and caerulein-induced acute pancreatitis.

In addition to the caerulein-induced AP model, various compounds have been infused into the pancreatic duct to induce acute pancreatitis. Following duodenotomy, retrograde injection of bile salts into the pancreatic duct at the ampulla has been demonstrated to induce severe acute pancreatitis. The pressure or the concentration of bile salt used in this model is a critical determinant of the severity of the disease. Bile salt-induced acute severe pancreatitis develops within 2-24 h and is characterized by the development of oedema, necrosis of the pancreas and haemorrhage. One of the best standardized compounds used to develop acute pancreatitis is sodium taurocholate. Infusion of 1-5% solution induces acute haemorrhagic pancreatitis with significant mortality rates within a 72 hour period. This model is appropriate for studies of systemic issues underlying pancreatitis.

Despite extensive research (experimental and clinical) and significant progress has been made to unraveled the disease pathophysiology associated with pancreatitis, along with some potentially promising therapeutic approaches, no drugs have been approved by the Food and Drug Administration for treatment of AP or CP, and morbidity remains high, thus underlining the unmet need to identify potential therapeutic targets for drug targeting.

The nuclear receptor (NR) superfamily represents a large group of ligand dependent transcription factors. The nuclear receptor family is uniquely differently from other classes of receptors in their ability to directly interact with and control the expression of genomic DNA. As a consequence, nuclear receptors play key roles in both embryonic development and adult metabolic homeostasis. The estrogen-related receptors (ERRs) were the first orphan members of the superfamily of nuclear receptors to be identified, and the subfamily is now known to contain three related isoforms, ERRα (also known as NR3B1, Esrra, ERRa), β (also known as NR3B2, Esrr, ERRb), and γ (also known as NR3B3, Esrrg, ERRg). Although named after the estrogen receptors due to their structural homology, the ERRs are not activated by estrogens (ligand for estrogen receptors) or any known natural compounds. ERRs play an important role in the transcriptional control of metabolic genes involved in the generation and utilization of cellular energy and thus plays a critical role in key facets of organ development as well as cellular homeostasis. ERRs are primarily expressed in the heart, skeletal muscle, brain, kidney, pancreas, placenta, and liver and are predicted to have significant differences in their synthetic ligand binding preferences.

Recent findings in various mammalian experimental models show that ERRg, as a downstream mediator of multiple extracellular signals, plays a key role in coordinating endocrine and metabolic signals, resulting in changes in glucose, alcohol, lipid, and iron metabolism. Therefore, dysregulation of ERRg contributes to the pathogenesis of metabolic diseases such as hyperglycemia, insulin resistance, and alcoholic liver injury. Interestingly, ERRg has been shown to be involved in the pathogenesis of bacterial infection. These findings indicate the importance of ERRg in the endocrine and metabolic control of metabolism, and suggest that ERRg may be a promising therapeutic target for several diseases.

U.S. application Ser. No. 16/313,360 (US Application Publication No. 2019/0167820 A1) and Ser. No. 16/677,596 (Application Publication No. 20200078476 A1), of which entire contents are incorporated herein by reference, disclose novel aryl ethane derivatives as estrogen-related receptor gamma (ERRg) inhibitors.

The disclosure is based on the new finding that certain compounds with ERRg inhibiting activity may be useful in the treatment of pancreatitis and acute inflammation conditions.

SUMMARY

In general, the present disclosure relates to methods and/or uses for treating pancreatitis, which comprises administering an arylethene compound of Chemical Formula (I), an isomer, a prodrug, a pharmaceutically acceptable salt, or a solvate thereof.

The disclosure is directed to a method for preventing and/or treating pancreatitis in a subject in need thereof, comprising administering to the subject an aryethene compound of the following Chemical Formula 1:

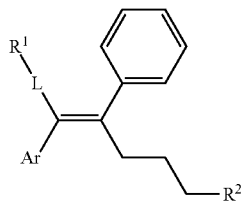

Chemical Formula 1 wherein

L is (C6-C20)arylene, (C3-C20)heteroarylene, or (C3-C20)fused heterocycle;

$R^1$ is (C3-C20)heterocycloalkyl, (C3-C20)heteroaryl, —O—$(CH_2)_m$—$R^{11}$, —$(CH_2)_m$—$R^{12}$, —NH—$(CH_2)_m$—$R^{13}$, —NHCO—$(CH_2)_n$—$R^{14}$, or —$SiR^{16}R^{17}$—$(CH_2)_m$—$R^{15}$;

$R^{11}$ to $R^{15}$ are independently of one another (C3-C20) heterocycloalkyl;

$R^{16}$ and $R^{17}$ are independently of each other (C1-C20) alkyl;

m is an integer of 1 to 3; and n is an integer of 0 or 1;

Ar is (C6-C20)aryl or (C3-C20)heteroaryl, in which the aryl or heteroaryl of Ar may be further substituted by one or more selected from the group consisting of hydroxy, halogen, (C1-C20)alkyl, halo(C1-C20)alkyl, (C1-C20)alkoxy, nitro, cyano, —$NR^{21}R^{22}$, (C1-C20)alkylcarbonyloxy, (C1-C20)alkylcarbonylamino, guanidino, —$SO_2$—$R^{23}$, and —$OSO_2$—$R^{24}$;

$R^{21}$ and $R^{22}$ are independently of each other hydrogen, (C1-C20)alkylsulfonyl, or (C3-C20)cycloalkylsulfonyl;

$R^{23}$ and $R^{24}$ are independently of each other (C1-C20) alkyl, halo(C1-C20)alkyl, or (C3-C20)cycloalkyl;

$R^2$ is hydroxy, halogen, (C1-C20)alkylcarbonyloxy, or (C1-C20)alkylsulfonyloxy;

the heterocycloalkyl or heteroaryl of $R^1$ and the heterocycloalkyl of $R^{11}$ to $R^{15}$ may be further substituted by one or more selected from the group consisting of (C1-C20)alkyl, (C3-C20)cycloalkyl, (C2-C20)alkenyl, amidino, (C1-C20) alkoxycarbonyl, hydroxy, hydroxy(C1-C20)alkyl, and di(C1-C20)alkylamino(C1-C20)alkyl; and the heterocycloalkyl and heteroaryl contains one or more heteroatoms selected from the group consisting of N, O and S, and the heterocycloalkyl is a saturated or unsaturated mono-, bi-, or spirocycle having a carbon atom or nitrogen atom in a ring as a binding site, or a solvate, an isomer, or a pharmaceutically acceptable salt thereof.

Another aspect of this disclosure is a method for treating and/or preventing pancreatitis in a subject in need thereof, comprising administering a compound of Chemical Formula 2, or a pharmaceutically acceptable salt thereof, or a solvate thereof, Chemical Formula 2

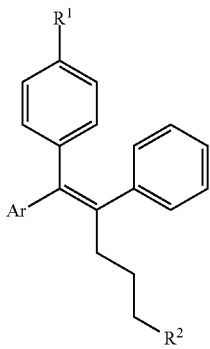

wherein
R¹ is (C3-C10)heterocycloalkyl or —O—(CH$_2$)$_m$—R¹¹;
R¹¹ is (C3-C10)heterocycloalkyl;
m is an integer of 1 to 3;
the heterocycloalkyl of R¹ and R¹¹ may be further substituted by one or more selected from the group consisting of (C1-C10)alkyl, (C3-C10)cycloalkyl, (C2-C10)alkenyl, amidino, (C1-C10)alkoxycarbonyl, hydroxy(C1-C10)alkyl, and di(C1-C20)alkylamino(C1-C20)alkyl;
Ar is (C6-C12)aryl or (C3-C12)heteroaryl, in which the aryl or heteroaryl of Ar may be further substituted by one or more selected from the group consisting of hydroxy, halogen, (C1-C10)alkyl, halo(C1-C10)alkyl, (C1-C10)alkoxy, nitro, cyano, amino, (C1-C10)alkylsulfonylamino, (C3-C10)cycloalkylsulfonylamino, di((C1-C10)alkylsulfonyl)amino, (C1-C10)alkylcarbonyloxy, (C1-C10)alkyl carbonyl amino, guanidino, (C1-C10)alkylsulfonyl, (C1-C10)alkylsulfonyloxy, halo(C1-C10)alkylsulfonyloxy, and (C3-C10)cycloalkylsulfonyloxy; and
R² is hydroxy, fluoro, (C1-C10)alkylcarbonyloxy, or (C1-C10)alkylsulfonyloxy.

Another aspect of this disclosure is a method for treating and/or preventing pancreatitis in a subject in need thereof, comprising administering a compound of Chemical Formula 6, or a pharmaceutically acceptable salt thereof, or a solvate thereof, Chemical Formula 6

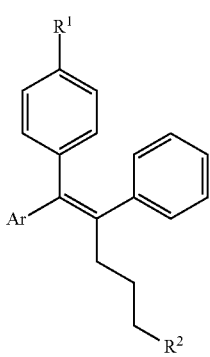

wherein
R¹ is (C3-C10)heterocycloalkyl or —O—(CH2)$_m$-R¹¹;
R¹¹ is (C3-C10)heterocycloalkyl;
m is an integer of 1 to 3;
Ar is s (C6-C12)aryl or (C3-C12)heteroaryl,
wherein the heterocycloalkyl, the aryl, or heteroaryl may be further substituted by one or more selected from the group consisting of hydroxy, halogen, (C1-C10)alkyl, halo(C1-C10)alkyl, (C1-C10)alkoxy, nitro, cyano, amino, (C1-C10)alkylsulfonylamino, (C3-C10)cycloalkylsulfonylamino, di((C1-C10)alkyl sulfonyl)amino, (C1-C10) alkylcarbonyloxy, (C1-C10)alkylcarbonylamino, guanidino, (C1-C10)alkyl sulfonyl, (C1-C10)alkylsulfonyloxy, halo(C1-C10)alkylsulfonyloxy, and (C3-C10)cycloalkylsulfonyloxy; and
R² is hydroxyl, halogen, (C1-C10) alkyl carbonyl oxy, or (C1-C10)alkylsulfonyloxy.

According to one embodiment, the compound of Chemical Formula 1 is selected from the following compounds:

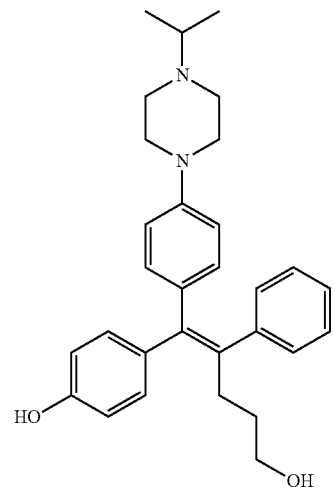

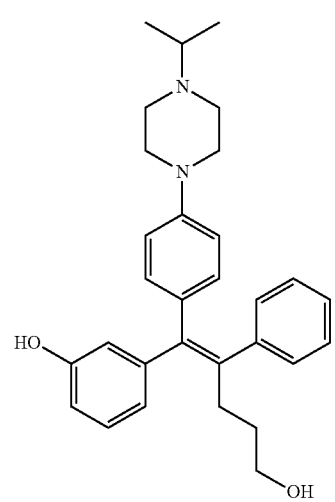

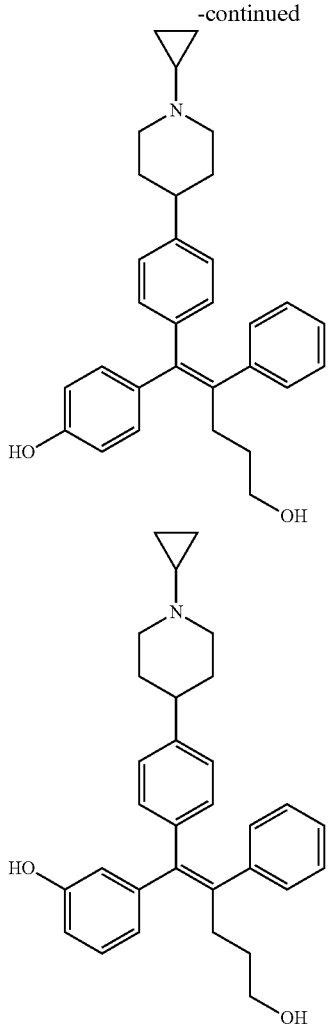

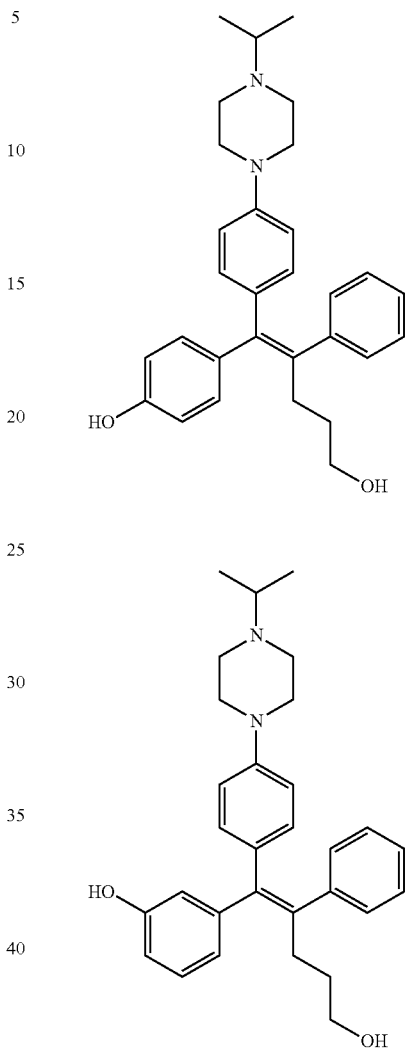

In one aspect, the pancreatitis is acute pancreatitis.

In still another aspect, the subject is a mammal, in particular human.

An aspect of the disclosure is further directed to a pharmaceutical composition for prevention and/or treatment of pancreatitis, comprising a therapeutically effective amount of a compound of Chemical Formula 1, a solvate, an isomer, or a pharmaceutically acceptable salt thereof, as an active ingredient, and a pharmaceutically acceptable excipient.

An aspect of the disclosure is further directed to a pharmaceutical composition for prevention and/or treatment of pancreatitis, comprising a therapeutically effective amount of a compound of Chemical Formula 2, a solvate, an isomer, or a pharmaceutically acceptable salt thereof, as an active ingredient, and a pharmaceutically acceptable excipient.

An aspect of the disclosure is further directed to a pharmaceutical composition for prevention and/or treatment of pancreatitis, comprising a therapeutically effective amount of a compound of Chemical Formula 6, a solvate, an isomer, or a pharmaceutically acceptable salt thereof, as an active ingredient, and a pharmaceutically acceptable excipient.

In an embodiment, the composition comprises a compound selected from the following compounds:

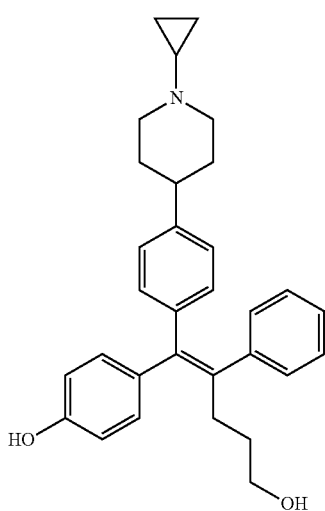

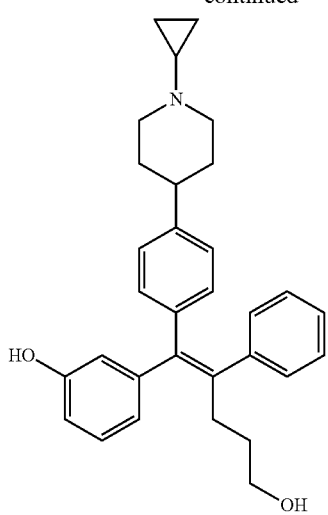

,

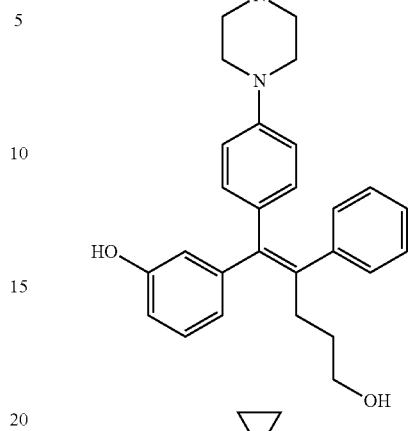

a solvate, an isomer, or a pharmaceutically acceptable salt thereof.

Still another aspect of the disclosure is directed to the use of a compound of Chemical Formula 1, a solvate, an isomer, or a pharmaceutically acceptable salt thereof in the manufacture of a medicament for the prevention and/or treatment of pancreatitis. In an embodiment, pancreatitis is acute pancreatitis.

Another aspect of the disclosure is a use of a compound of the Chemical Formula 2 or a pharmaceutically acceptable salt thereof in the manufacture of a medicament for the prevention and/or treatment of pancreatitis. In an embodiment, pancreatitis is acute pancreatitis.

Another aspect of the disclosure is a use of a compound of the Chemical Formula 6 or a pharmaceutically acceptable salt thereof in the manufacture of a medicament for the prevention and/or treatment of pancreatitis. In an embodiment, pancreatitis is acute pancreatitis.

Still another aspect of the embodiment is a use of the following compound:

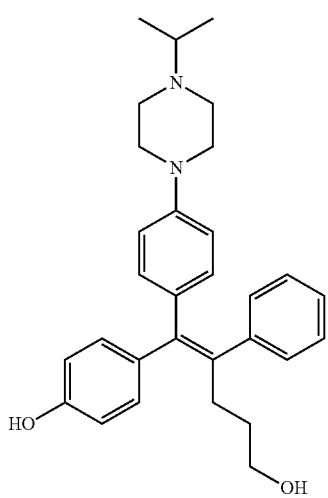

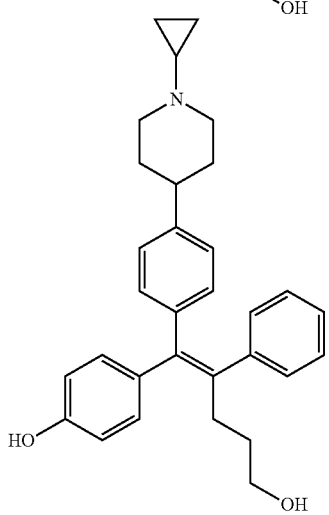

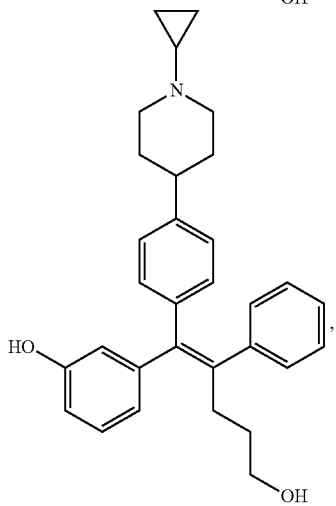

, or a pharmaceutically acceptable salt thereof, or a solvate, or an isomer thereof, in the manufacture of a medicament for the prevention and/or treatment of pancreatitis. In an embodiment, pancreatitis is acute pancreatitis.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The disclosure may be better understood by reference to one or more of these drawings in combination with the detailed description of specific have embodiments presented herein.

FIG. 1A shows ERRa or ERRg mRNA expression levels from indicated mouse pancreas (n=4 per group) 16 hr after Caerulein challenge (50 ug/kg i.p., hourly injection, 6×), determined by real-time quantitative PCR (RT-qPCR) upon and expressed as fold change compared to the levels of expression in mice treated with saline (n=3). FIG. 1B shows the results of immunoblotting of pancreas tissue extracts, wherein the pancreas tissue extracts were subjected to SDS-PAGE and immunoblotted by anti-ERRa or anti-ERRg antibodies.

DETAILED DESCRIPTION OF EMBODIMENTS

Figure 1A:
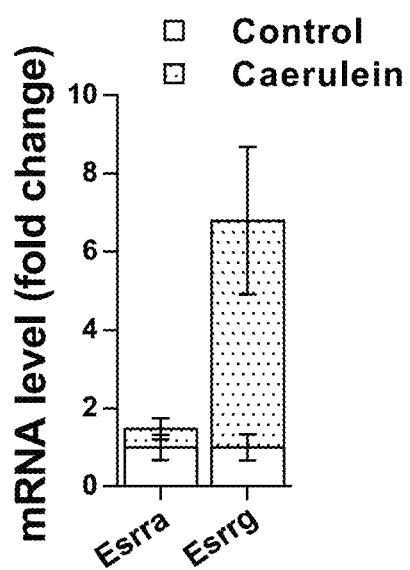
FIGS. 1A and 1B show differential regulation of ERRa and ERRg in mouse pancreas by Caerulein.

The disclosure is directed to a method for preventing and/or treating pancreatitis, comprising administering an arylethene compound of Chemical Formula 1:

Chemical Formula 1

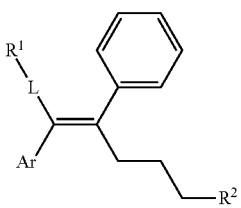

wherein

L is (C6-C20)arylene, (C3-C20)heteroarylene, or (C3-C20)fused heterocycle;

$R^1$ is (C3-C20)heterocycloalkyl, (C3-C20)heteroaryl, —O—$(CH_2)_m$—$R^{11}$, —$(CH_2)_m$—$R^{12}$, —NH—$(CH_2)_m$—$R^{13}$, —NHCO—$(CH_2)_n$—$R^{14}$, or —$SiR^{16}R^{17}$—$(CH_2)_m$—$R^{15}$;

$R^{11}$ to $R^{15}$ are independently of one another (C3-C20) heterocycloalkyl;

$R^{16}$ and $R^{17}$ are independently of each other (C1-C20) alkyl;

m is an integer of 1 to 3; and n is an integer of 0 or 1;

Ar is (C6-C20)aryl or (C3-C20)heteroaryl, in which the aryl or heteroaryl of Ar may be further substituted by one or more selected from the group consisting of hydroxy, halogen, (C1-C20)alkyl, halo(C1-C20)alkyl, (C1-C20)alkoxy, nitro, cyano, —$NR^{21}R^{22}$, (C1-C20)alkylcarbonyloxy, (C1-C20)alkylcarbonylamino, guanidino, —$SO_2$—$R^{23}$, and —$OSO_2$—$R^{24}$;

$R^{21}$ and $R^{22}$ are independently of each other hydrogen, (C1-C20)alkylsulfonyl, or (C3-C20)cycloalkylsulfonyl;

$R^{23}$ and $R^{24}$ are independently of each other (C1-C20) alkyl, halo(C1-C20)alkyl, or (C3-C20)cycloalkyl;

$R^2$ is hydroxy, halogen, (C1-C20)alkylcarbonyloxy, or (C1-C20)alkylsulfonyloxy;

the heterocycloalkyl or heteroaryl of $R^1$ and the heterocycloalkyl of $R^{11}$ to $R^{15}$ may be further substituted by one or more selected from the group consisting of (C1-C20)alkyl, (C3-C20)cycloalkyl, (C2-C20)alkenyl, amidino, (C1-C20) alkoxycarbonyl, hydroxy, hydroxy(C1-C20)alkyl, and di(C1-C20)alkylamino(C1-C20)alkyl; and the heterocycloalkyl and heteroaryl contains one or more heteroatoms selected from the group consisting of N, O and S, and the heterocycloalkyl is a saturated or unsaturated mono-, bi-, or spirocycle having a carbon atom or nitrogen atom in a ring as a binding site, or a solvate, an isomer, or a pharmaceutically acceptable salt thereof.

According to an embodiment, the compound can be a compound of the following Chemical Formula 2:

Chemical Formula 2

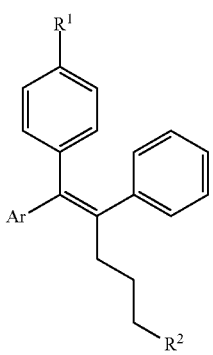

wherein $R^1$ is (C3-C10)heterocycloalkyl or —O—$(CH_2)_m$—$R^{11}$;

$R^{11}$ is (C3-C10)heterocycloalkyl;

m is an integer of 1 to 3;

the heterocycloalkyl of $R^1$ and $R^{11}$ may be further substituted by one or more selected from the group consisting of (C1-C10)alkyl, (C3-C10)cycloalkyl, (C2-C10)alkenyl, amidino, (C1-C10)alkoxycarbonyl, hydroxy(C1-C10)alkyl, and di(C1-C20)alkylamino(C1-C20)alkyl;

Ar is (C6-C12)aryl or (C3-C12)heteroaryl, in which the aryl or heteroaryl of Ar may be further substituted by one or more selected from the group consisting of hydroxy, halogen, (C1-C10)alkyl, halo(C1-C10)alkyl, (C1-C10)alkoxy, nitro, cyano, amino, (C1-C10)alkylsulfonylamino, (C3-C10)cycloalkylsulfonylamino, di((C1-C10)alkylsulfonyl)amino, (C1-C10)alkylcarbonyloxy, (C1-C10)alkylcarbonylamino, guanidino, (C1-C10)alkylsulfonyl, (C1-C10)alkylsulfonyloxy, halo(C1-C10)alkylsulfonyloxy, and (C3-C10)cycloalkylsulfonyloxy; and $R^2$ is hydroxy, fluoro, (C1-C10)alkylcarbonyloxy, or (C1-C10)alkylsulfonyloxy, or a solvate, an isomer, or a pharmaceutically acceptable salt thereof.

According to an embodiment, the compound can be a compound of the following Chemical Formula 6:

Chemical Formula 6

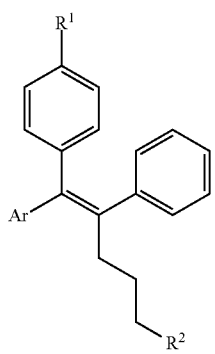

wherein $R^1$ is (C3-C10)heterocycloalkyl or —O—(CH2)$_m$-$R^{11}$;

$R^{11}$ is (C3-C10)heterocycloalkyl;

m is an integer of 1 to 3;

Ar is s (C6-C12)aryl or (C3-C12)heteroaryl, wherein the heterocycloalkyl, the aryl, or heteroaryl may be further substituted by one or more selected from the group consisting of hydroxy, halogen, (C1-C10)alkyl, halo(C1-C10)alkyl, (C1-C10)alkoxy, nitro, cyano, amino, (C1-C10)alkylsulfonylamino, (C3-C10)cycloalkylsulfonylamino, di((C1-C10)alkyl sulfonyl)amino, (C1-C10)alkylcarbonyloxy, (C1-C10)alkylcarbonylamino, guanidino, (C1-C10)alkyl sulfonyl, (C1-C10)alkylsulfonyloxy, halo(C1-C10)alkylsulfonyloxy, and (C3-C10)cycloalkylsulfonyloxy; and $R^2$ is hydroxyl, halogen, (C1-C10) alkylcarbonyloxy, or (C1-C10)alkylsulfonyloxy, a pharmaceutically acceptable salt thereof or a solvate thereof.

According to another embodiment, the compound of Chemical Formula 1 can be one selected from the following compounds:

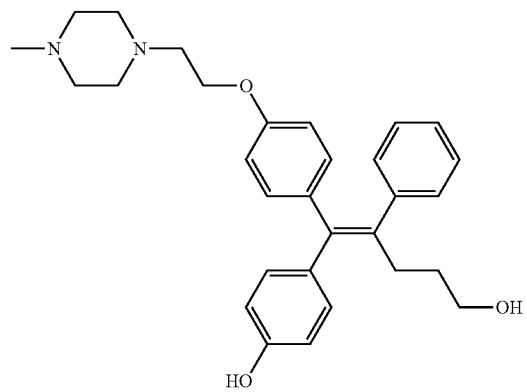

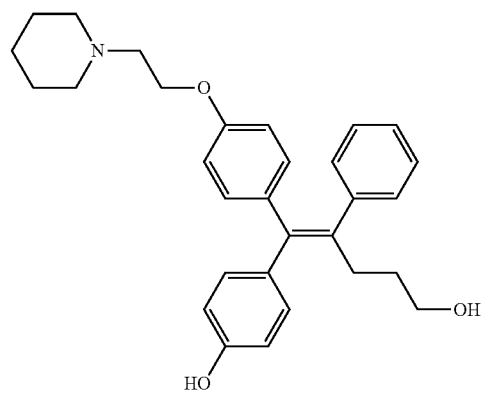

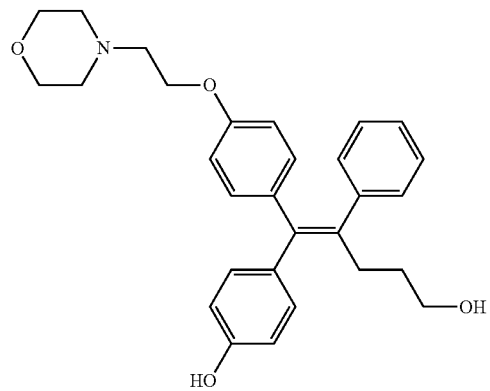

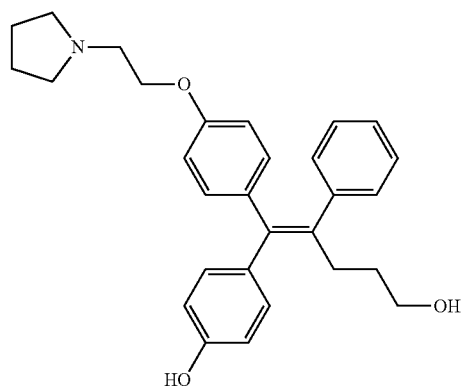

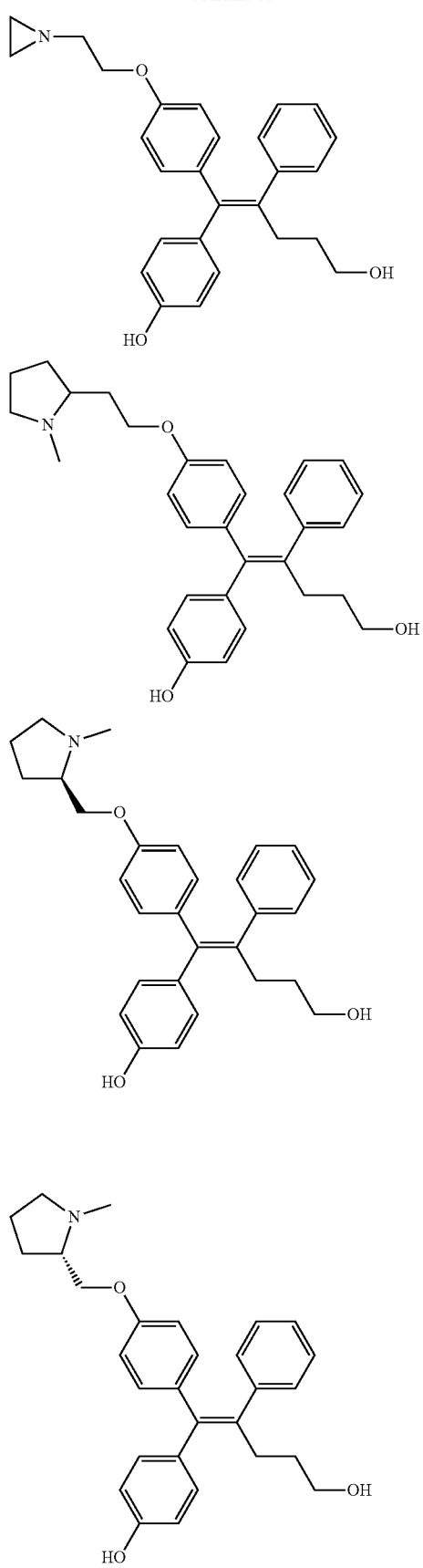
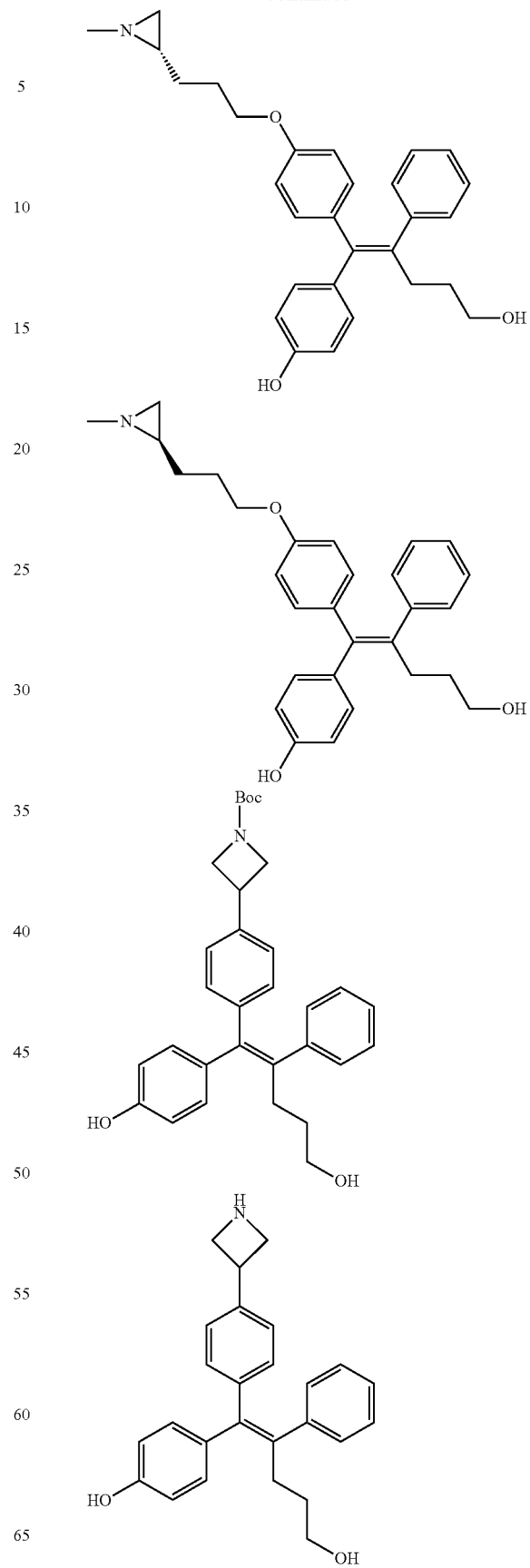

17
-continued
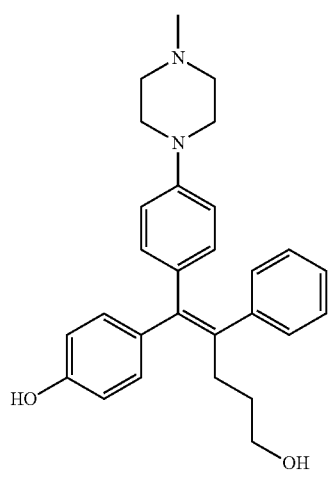
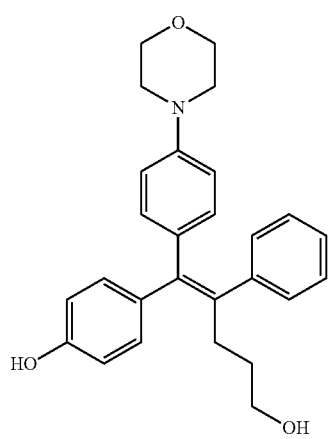
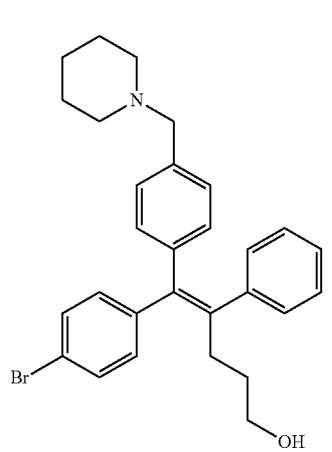
18
-continued
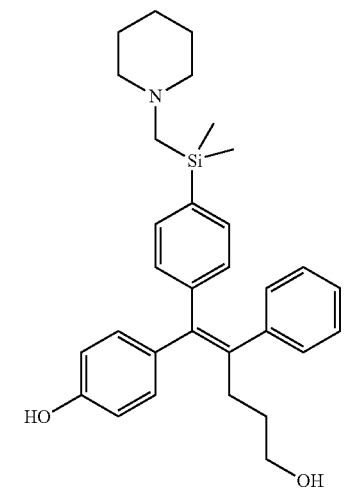
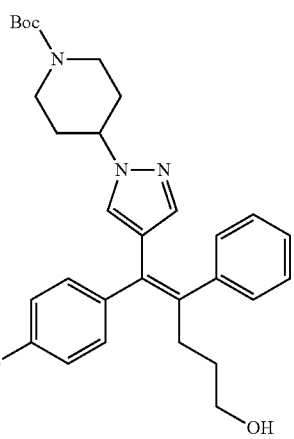
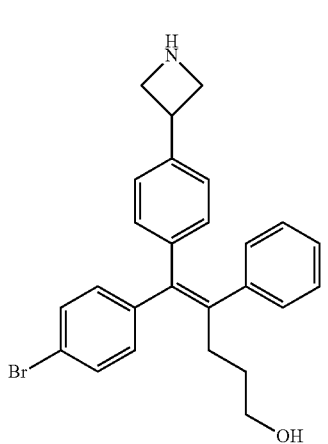

19
-continued
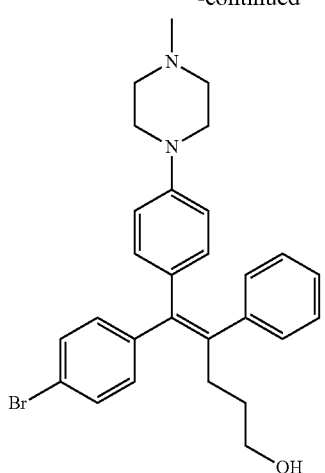
20
-continued
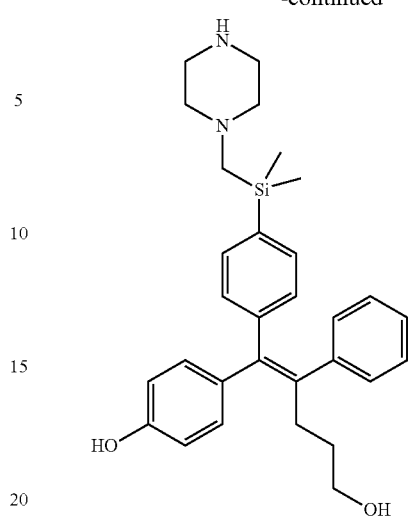
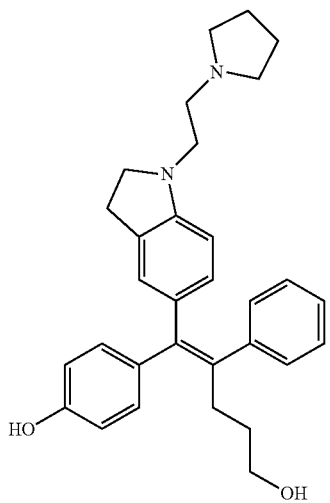
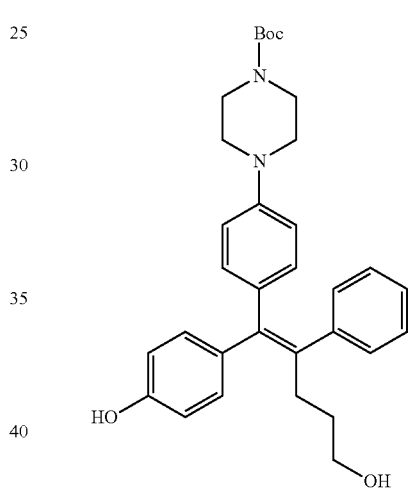
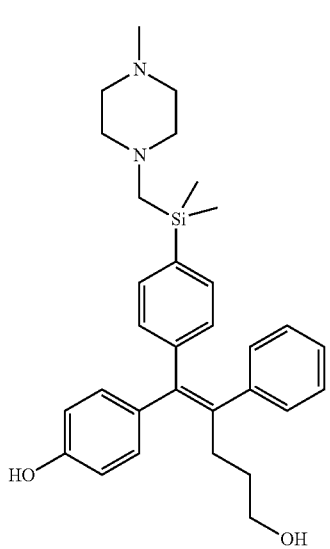
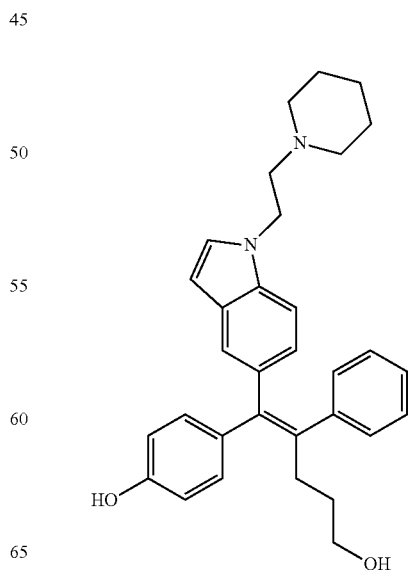

-continued
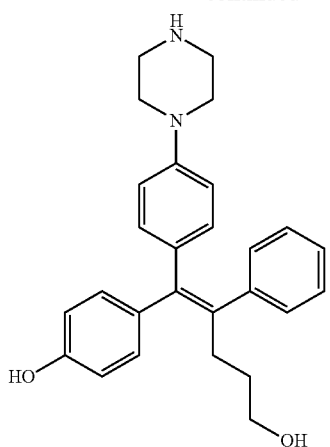
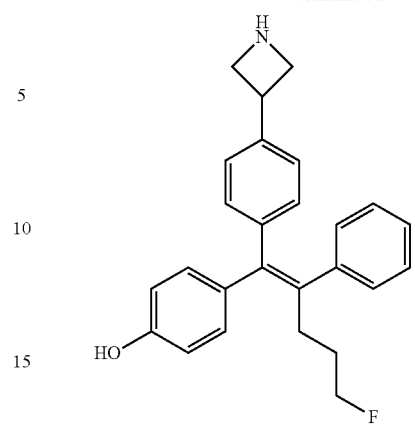
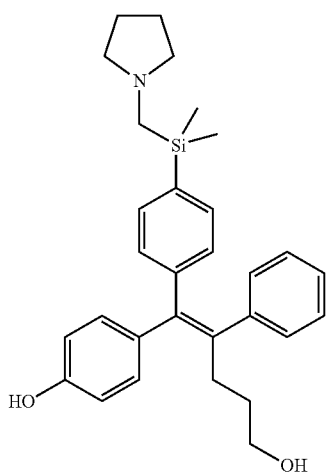
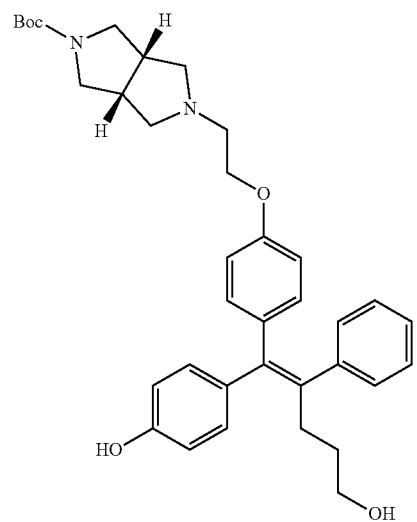
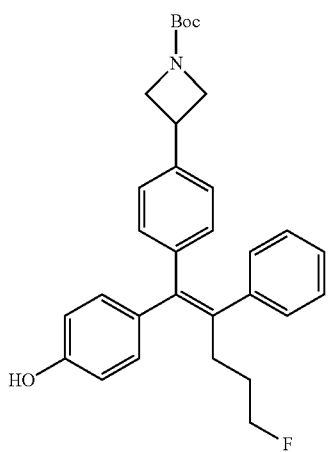
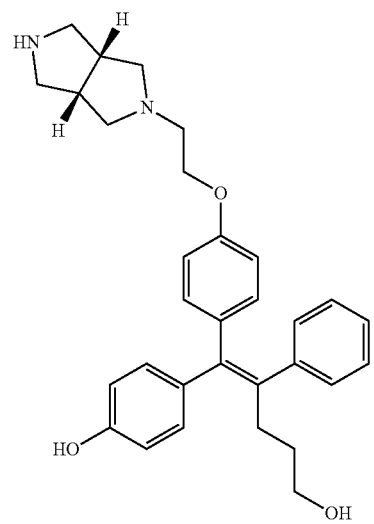

23
-continued
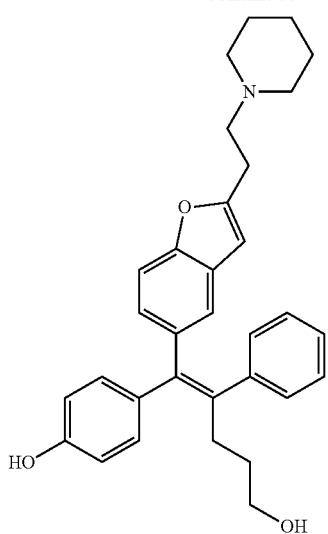
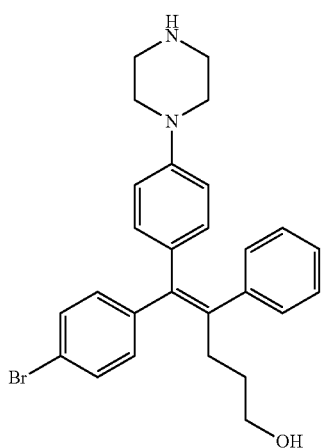
24
-continued
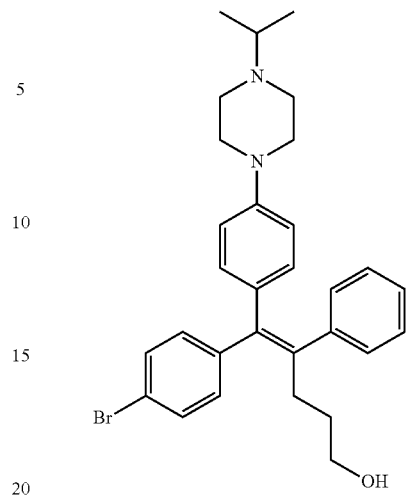
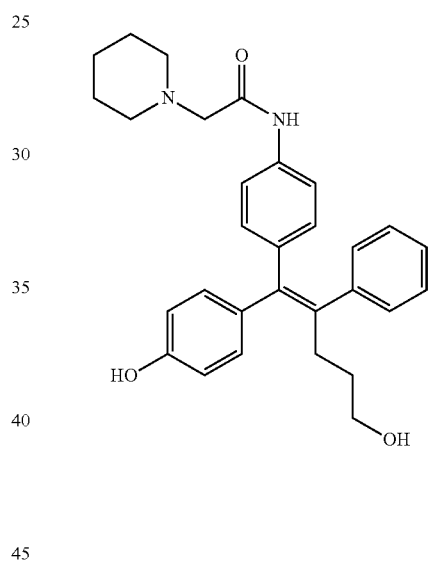
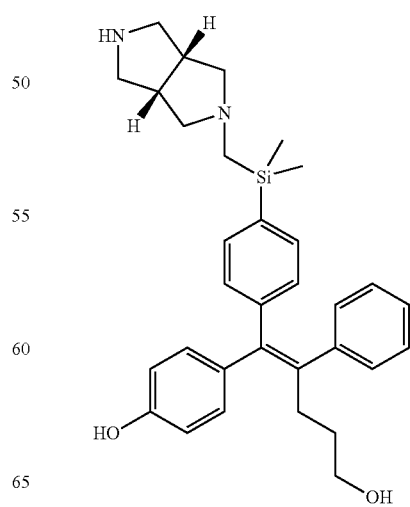

25
-continued
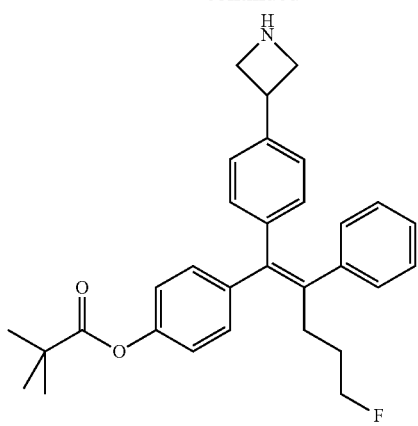
26
-continued
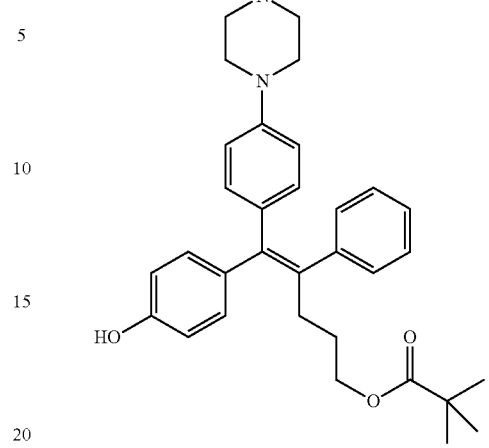
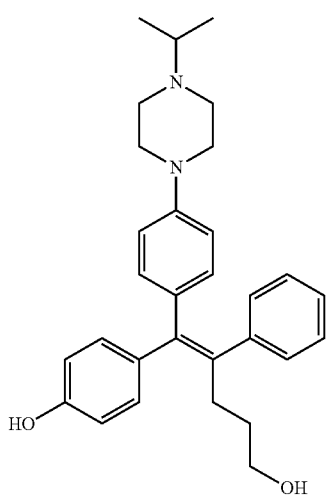
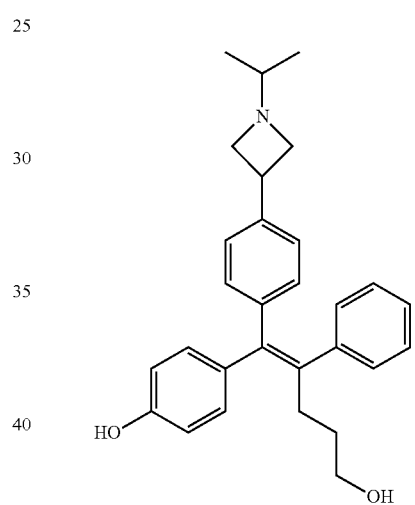
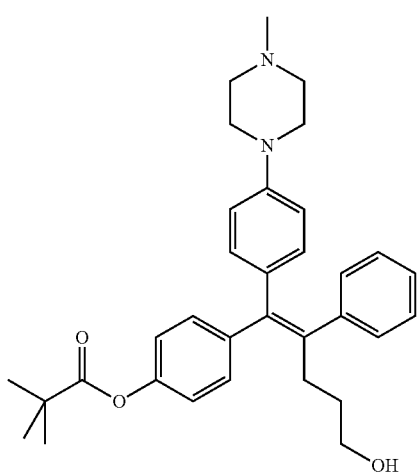
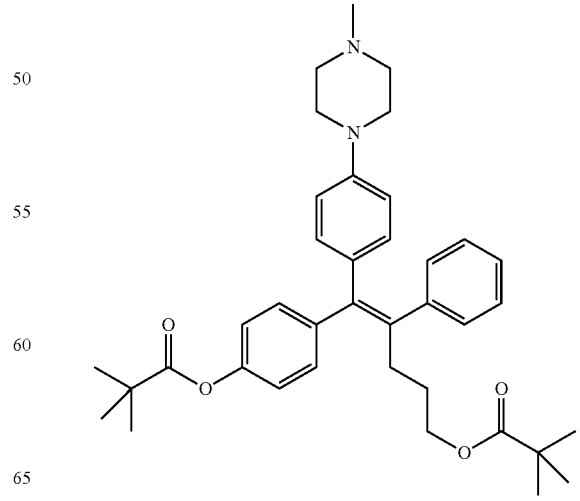

27
-continued
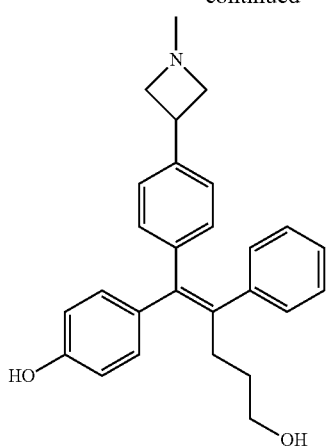
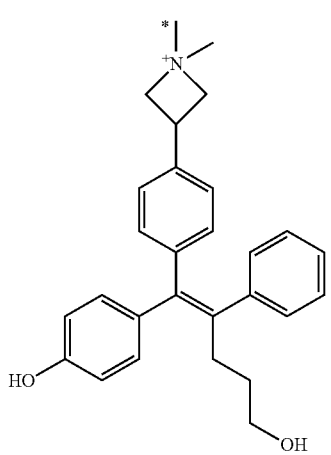
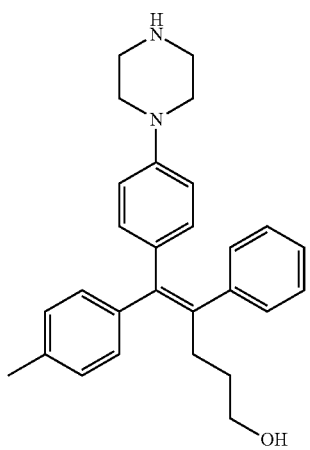
28
-continued
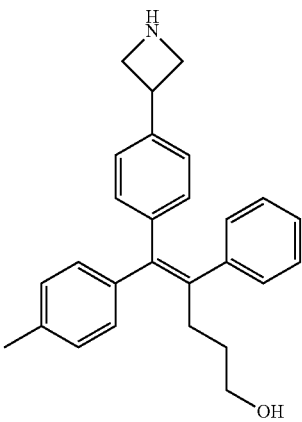
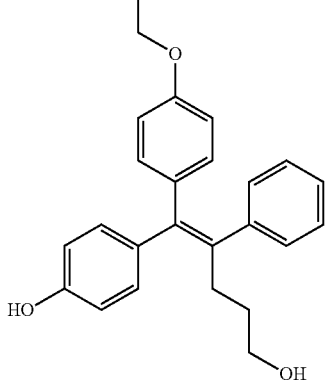

29
-continued
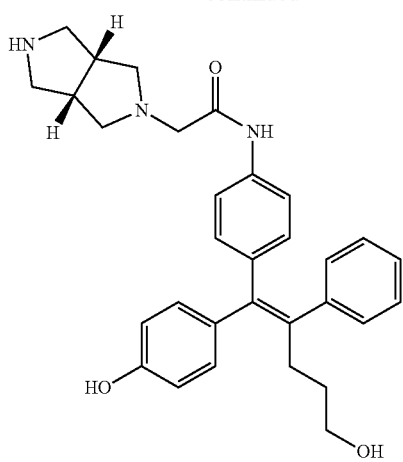
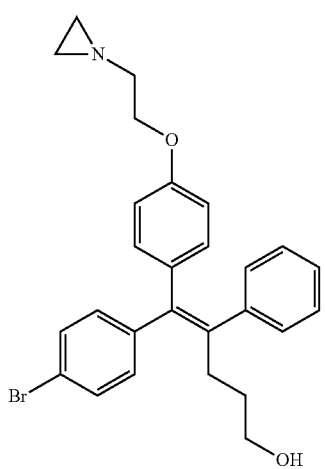
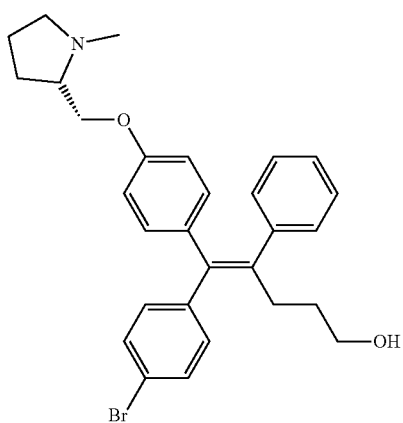
30
-continued
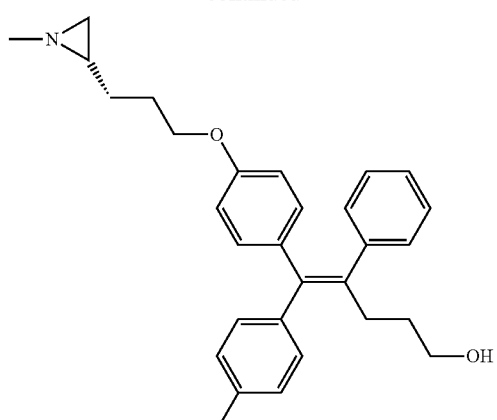
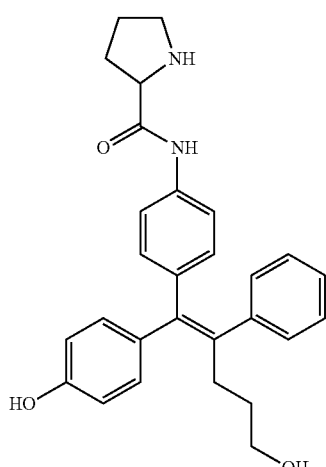
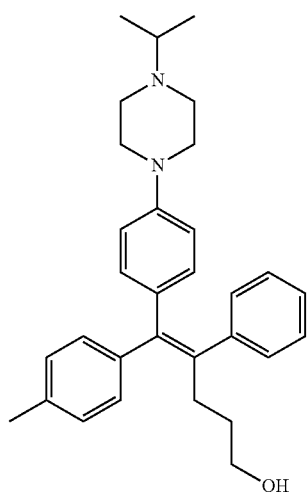

31
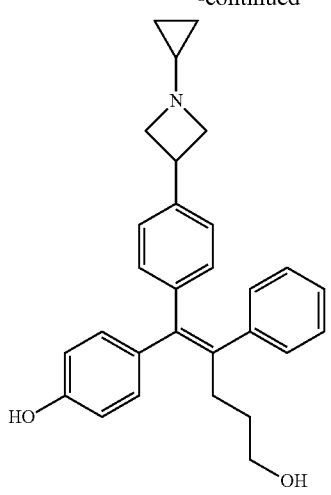
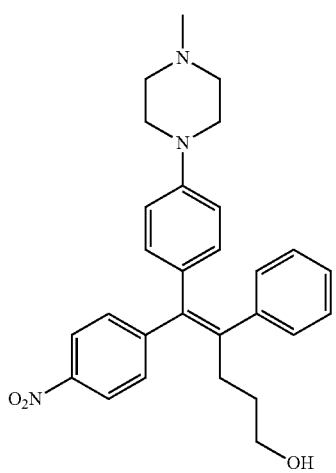
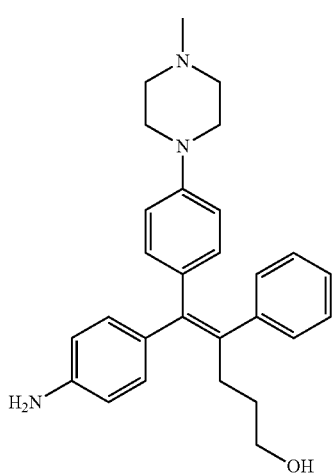
32
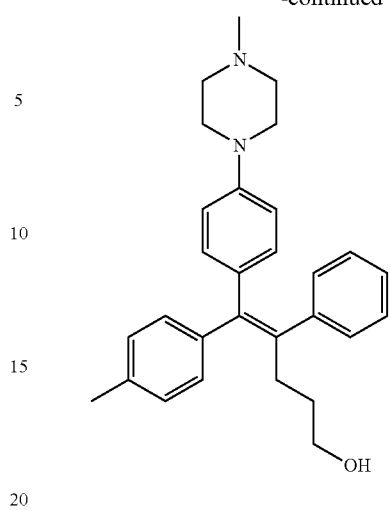
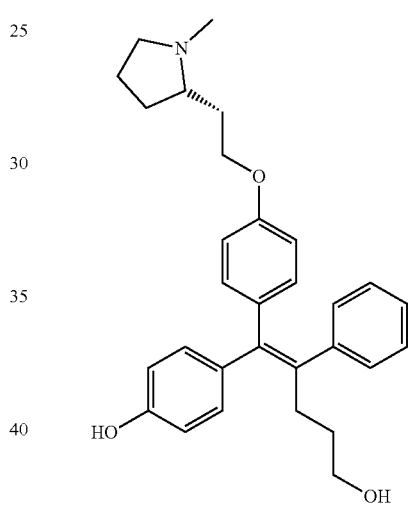
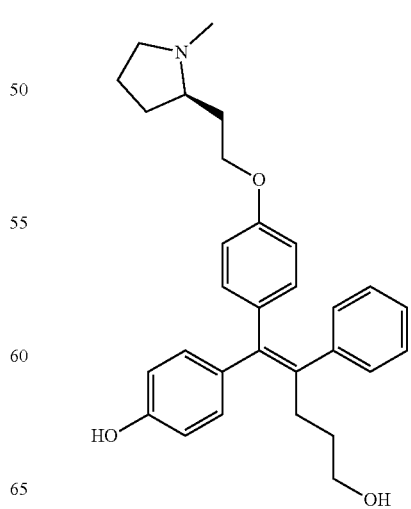

33
-continued
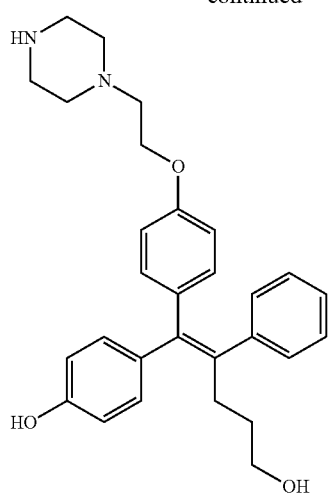
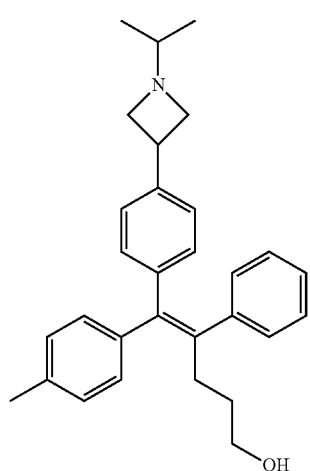
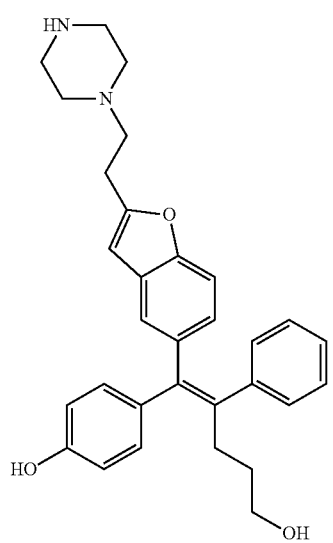
34
-continued
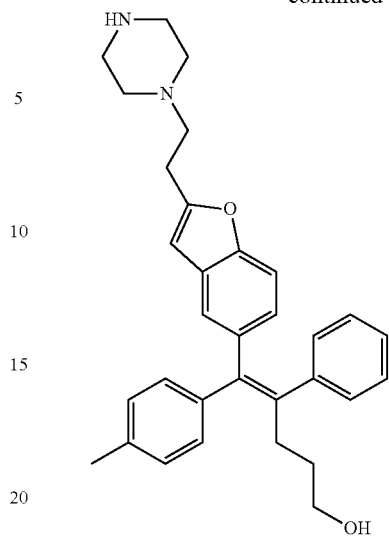
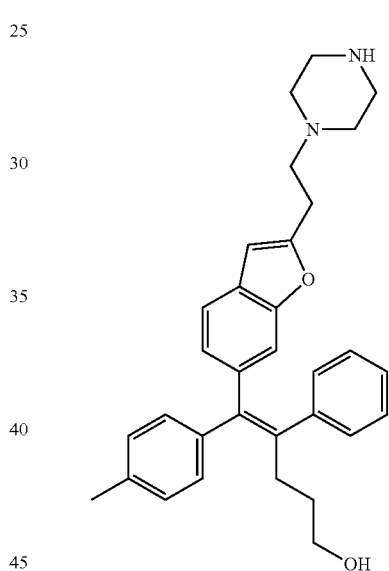
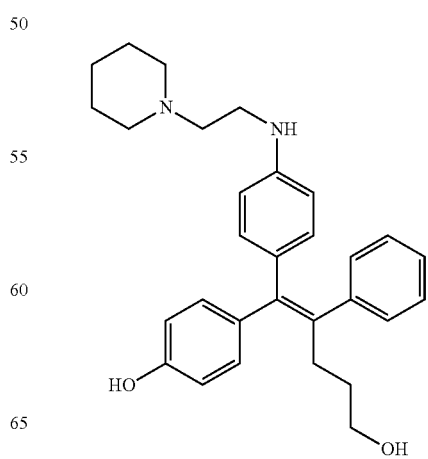

35
-continued
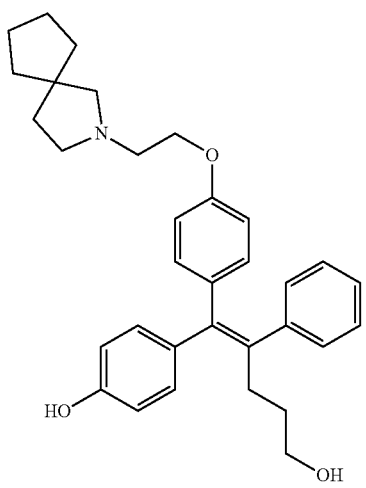
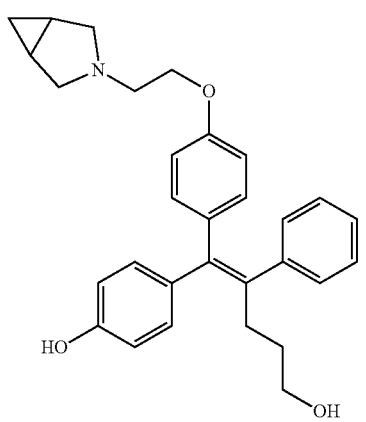
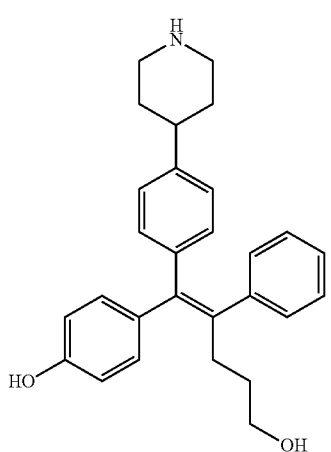
36
-continued
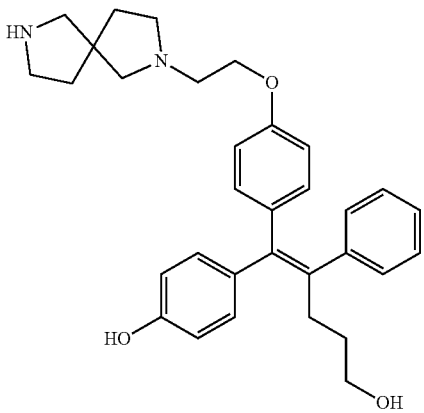
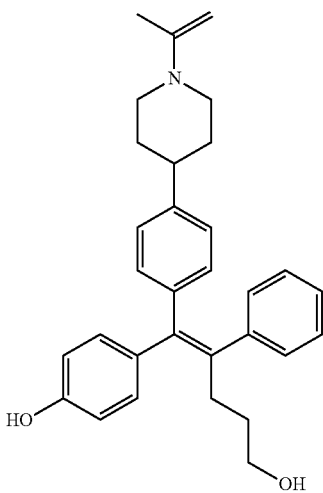
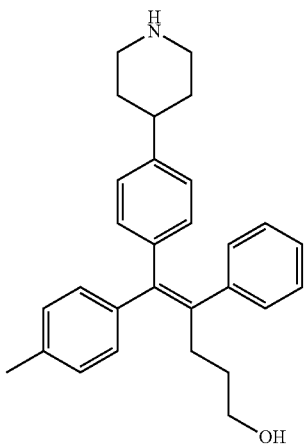

37
-continued
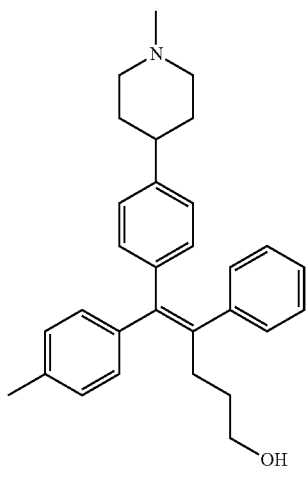
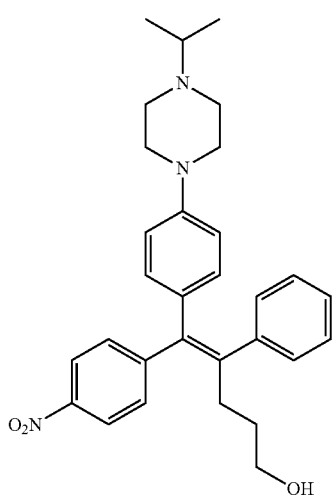
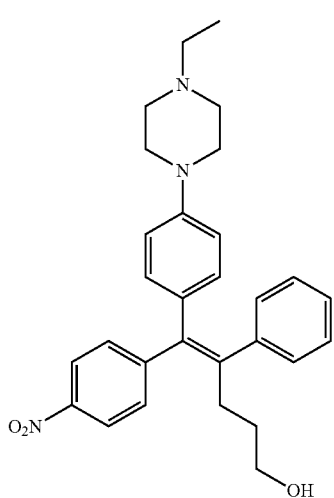
38
-continued
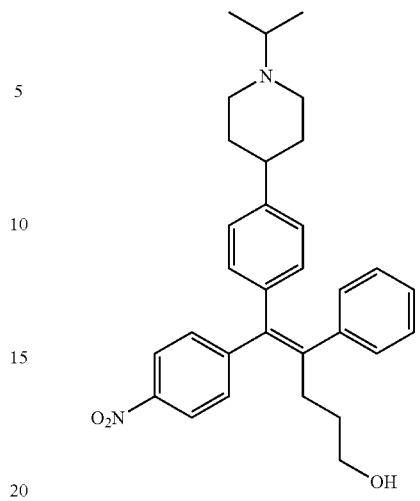
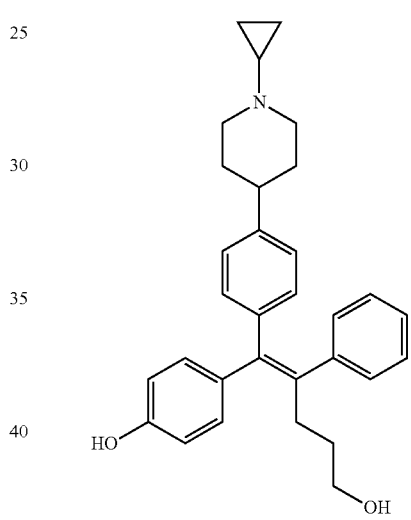
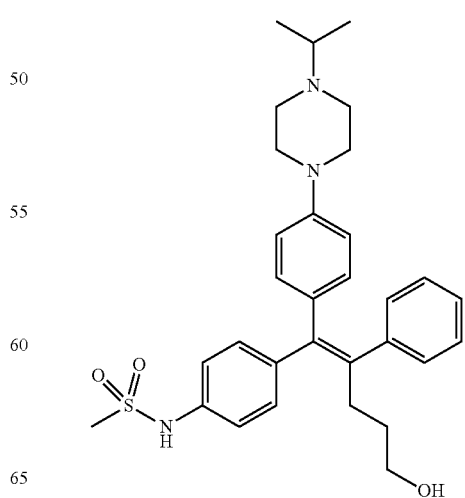

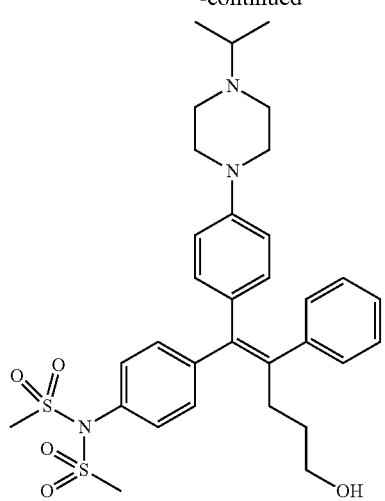
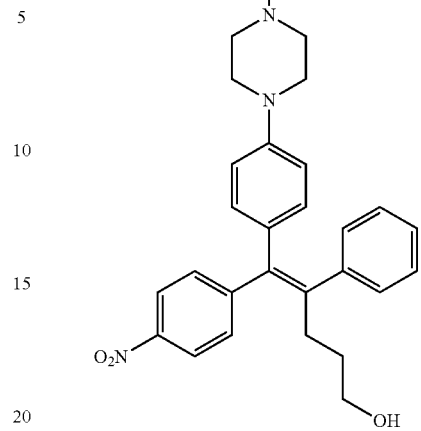
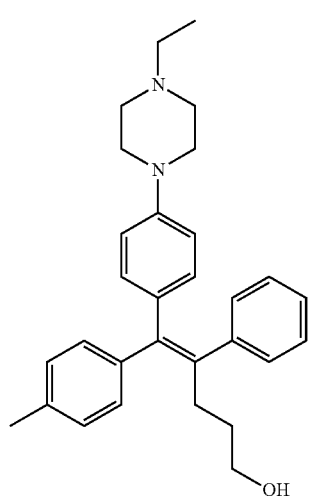
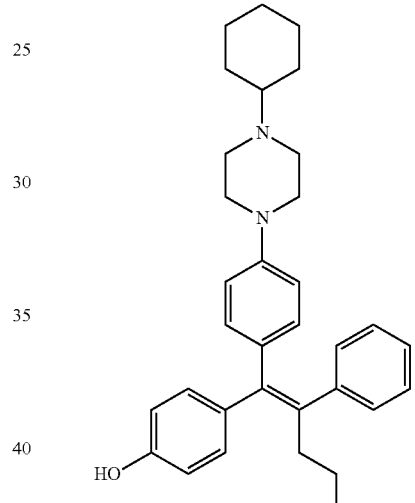
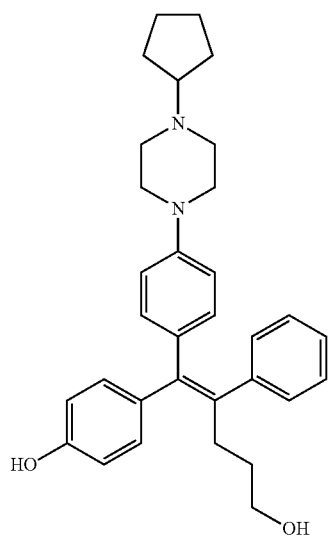
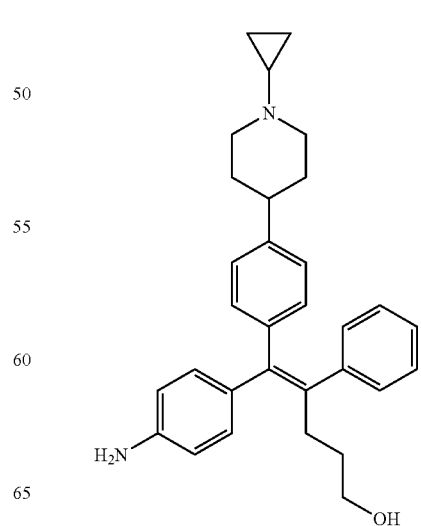

41
-continued
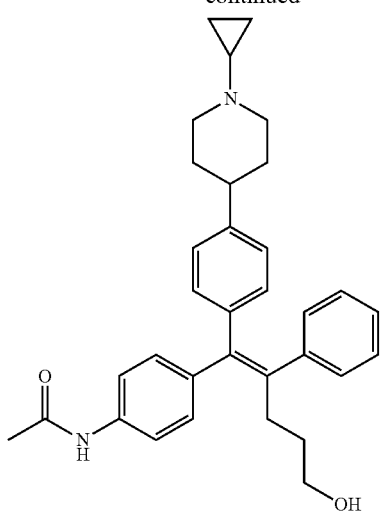
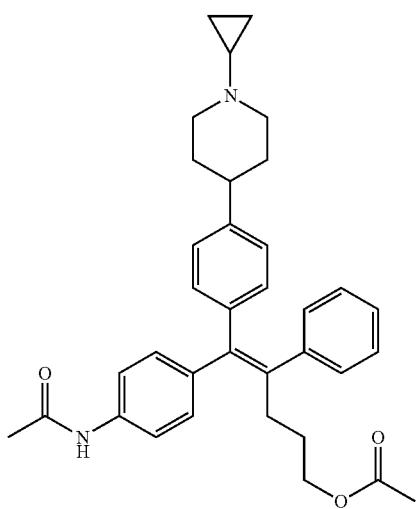
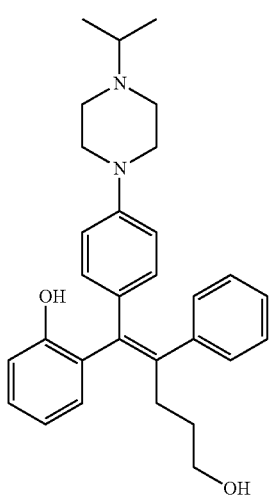
42
-continued
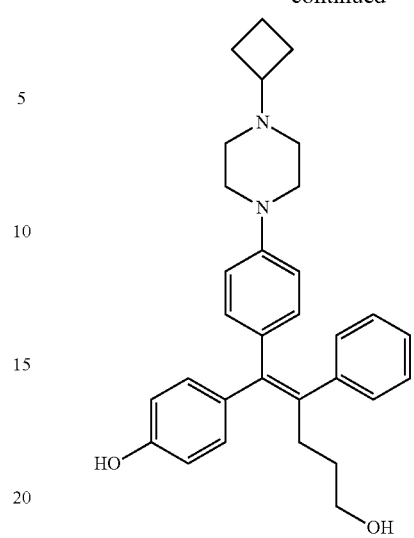
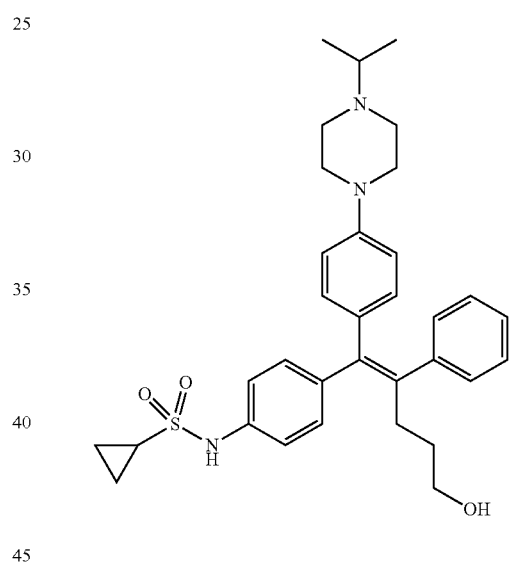
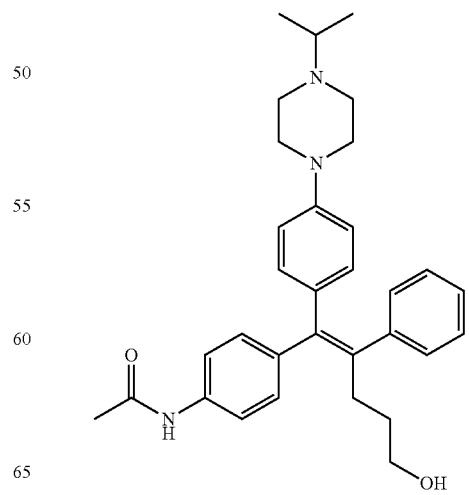

43
-continued
44
-continued
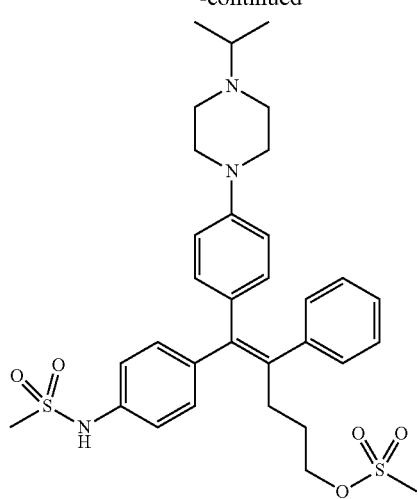
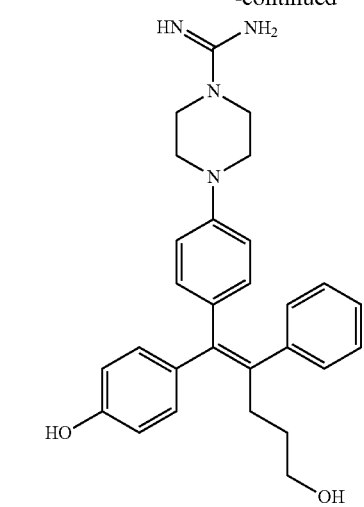
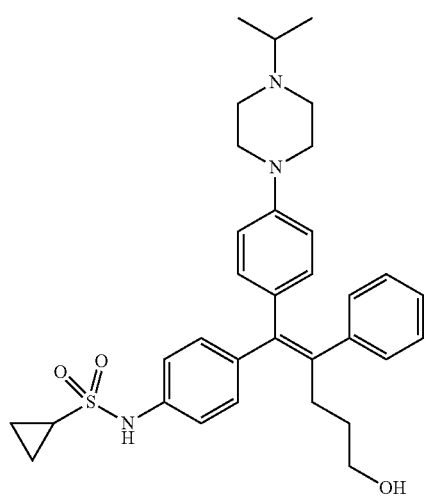
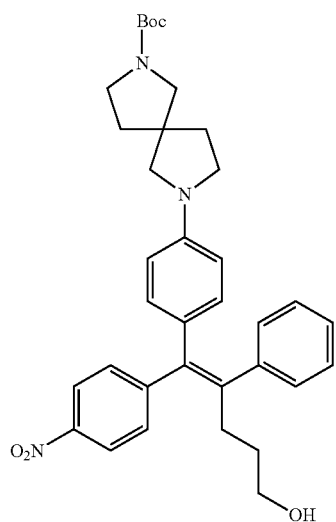
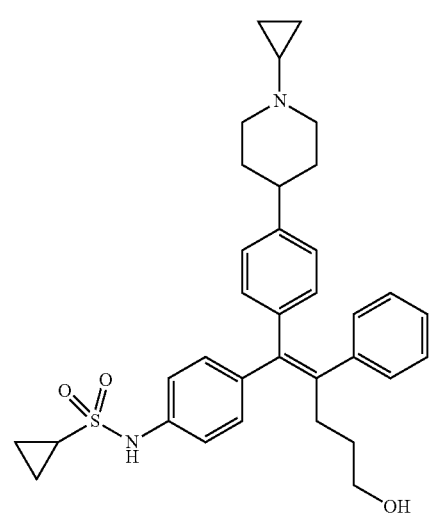

45
-continued
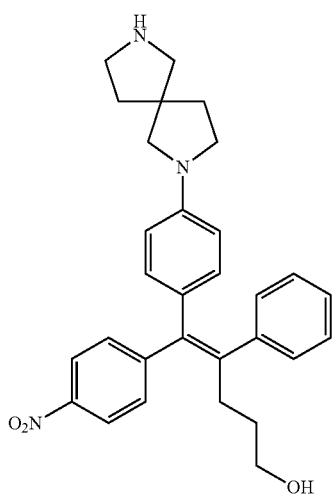
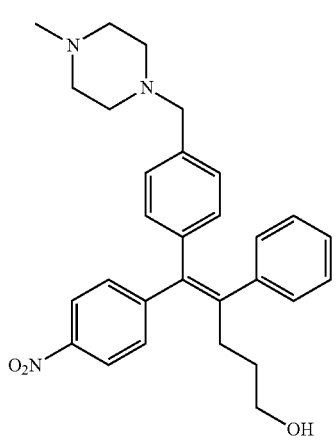
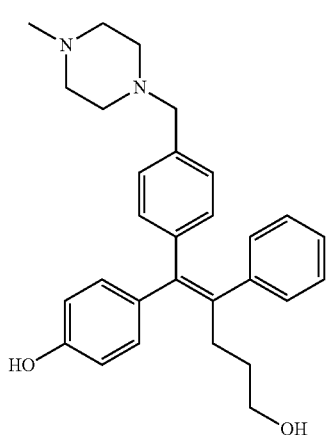
46
-continued
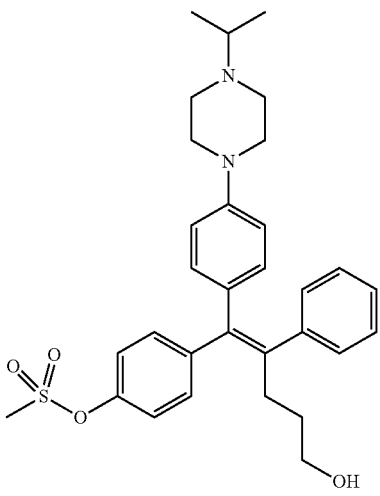
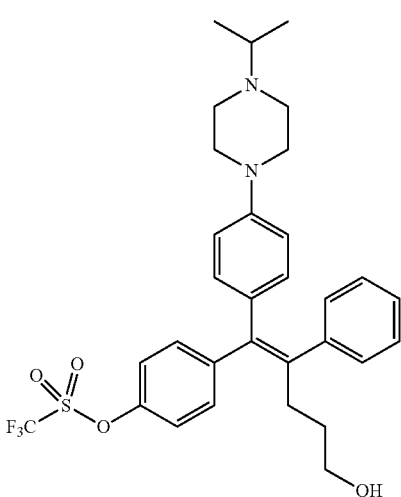
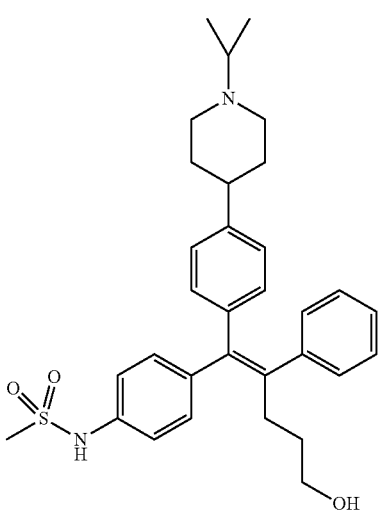

47
-continued
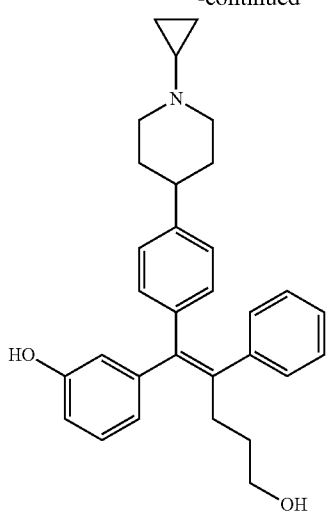
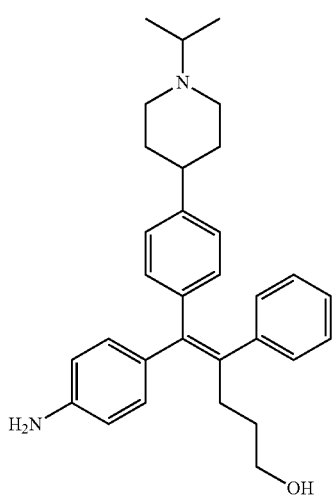
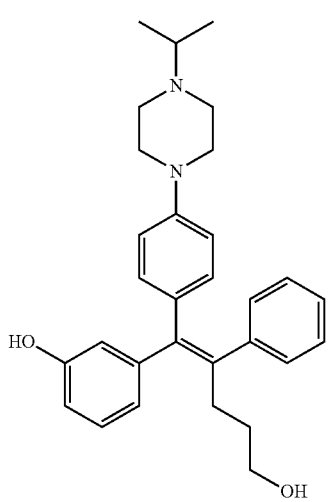
48
-continued
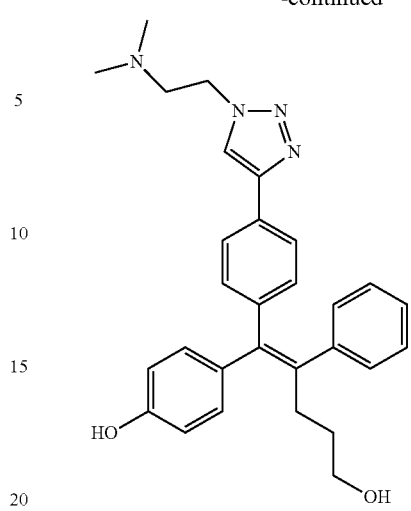
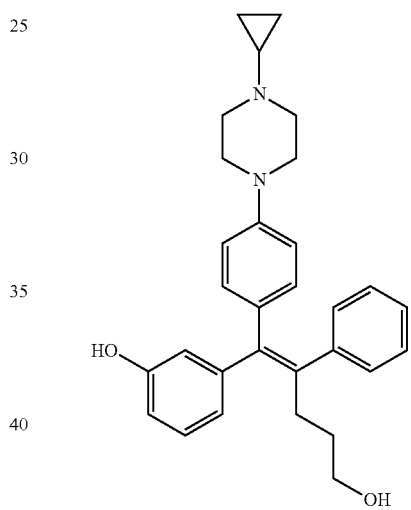
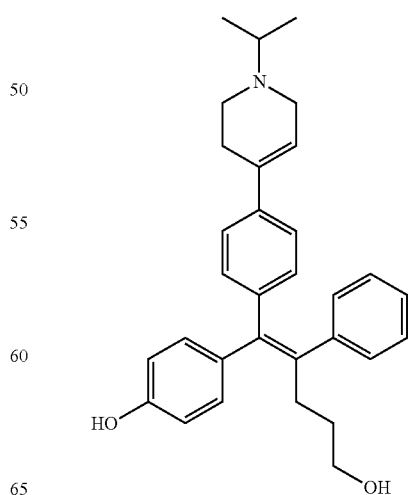

49
-continued
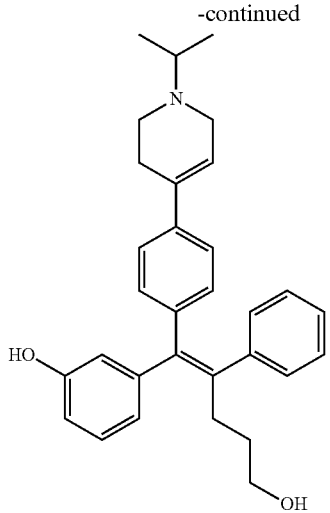
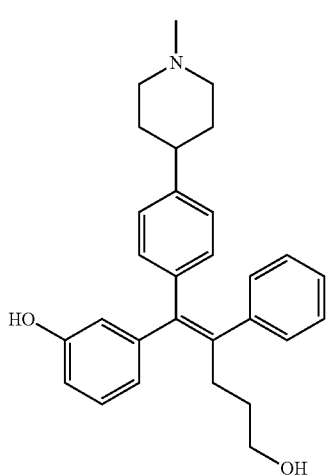
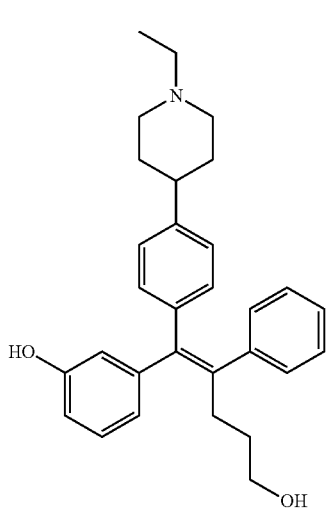
50
-continued
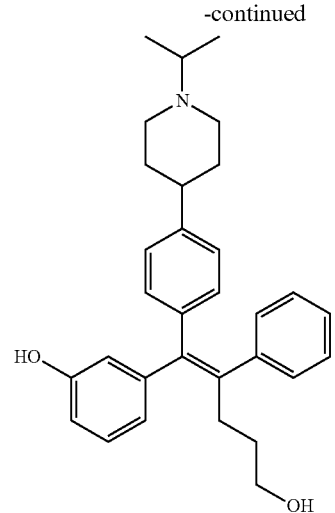
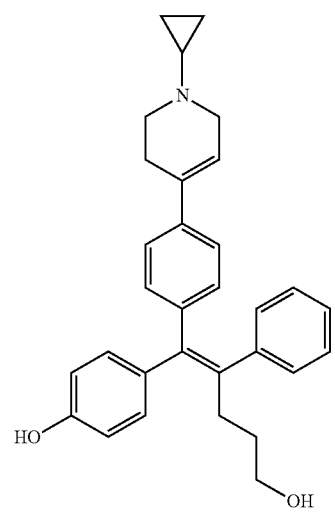
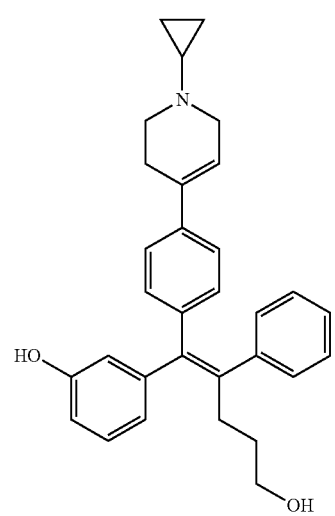

51
-continued
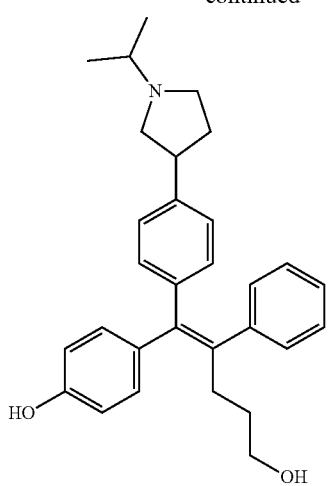
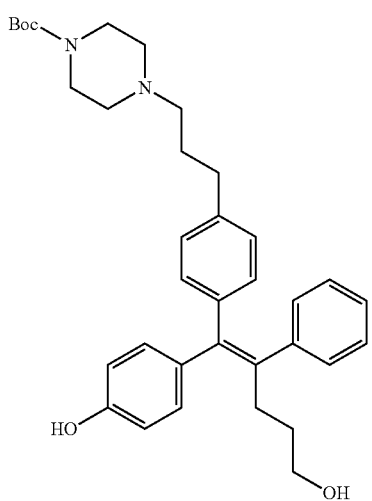
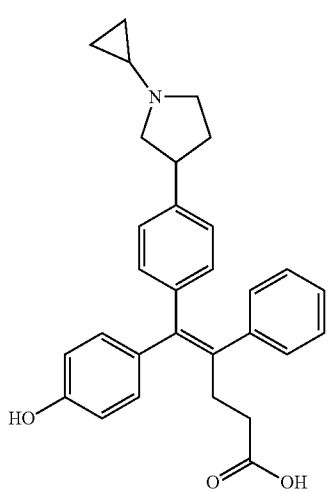
52
-continued
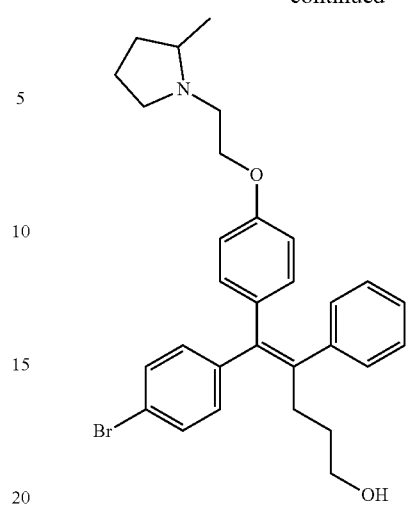
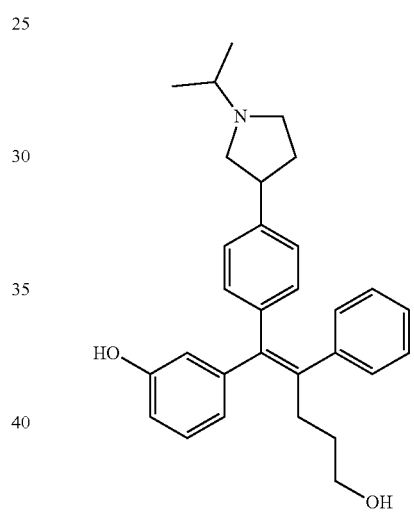
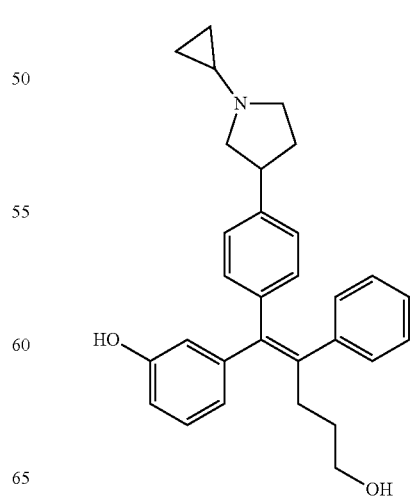

53
-continued
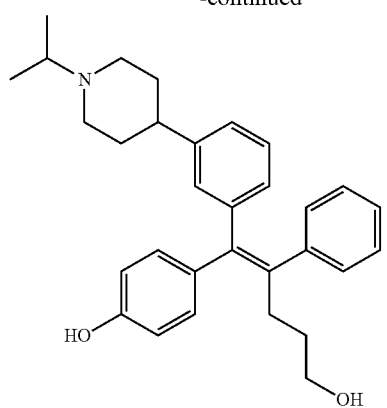
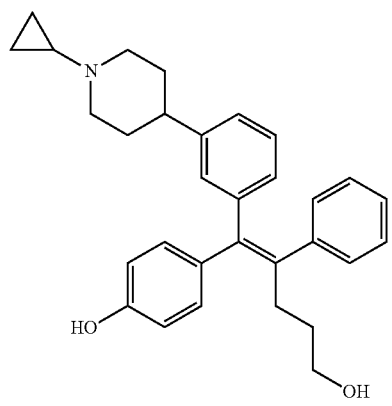
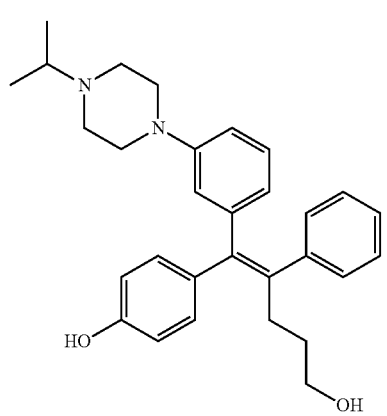
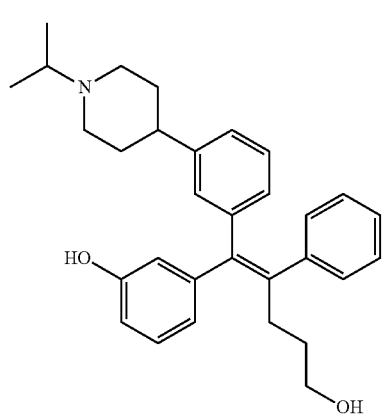
54
-continued
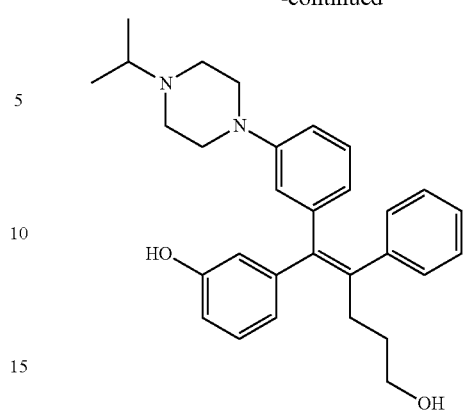
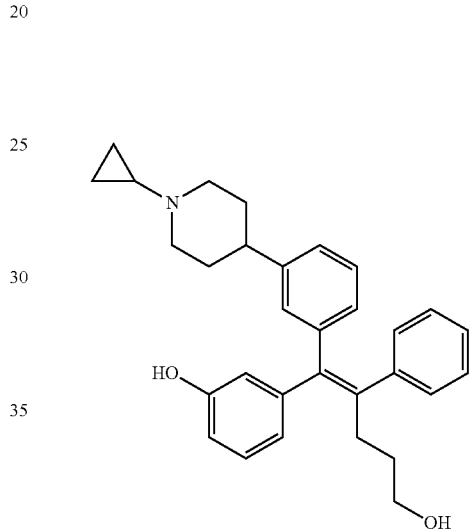
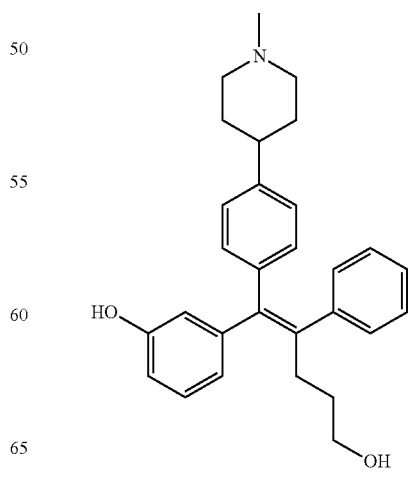

-continued
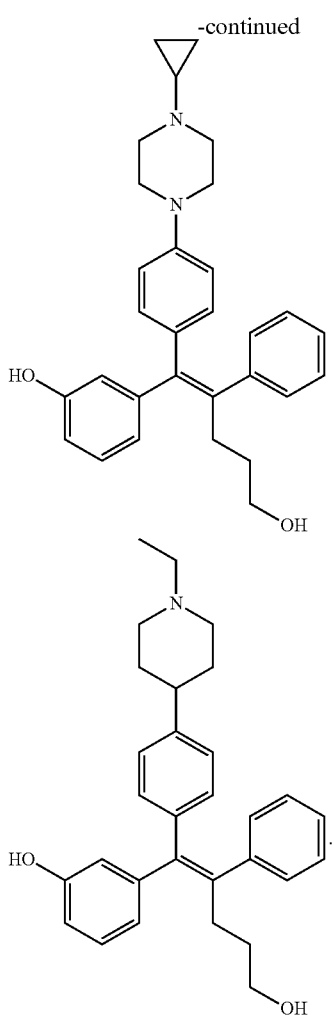
In still another embodiment, the compound of Chemical Formula 1 can be any of the following compounds:
Compound 18a (=DMRC200434)
(E)-5-(4-hydroxyphenyl)-5-(4-(4-isopropylpiperazin-1-yl)phenyl)-4-phenylpent-4-en-1-ol
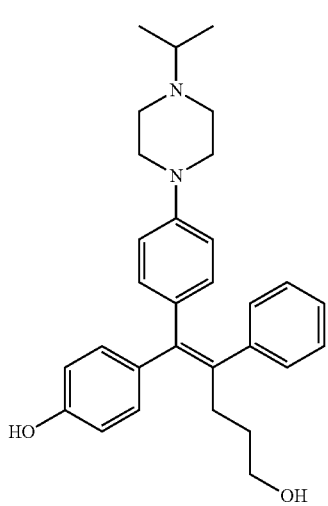
Compound 18k (=DMRC2001000)
(E)-5-(5-hydroxyphenyl)-5-(4-(4-isopropylpiperazin-1-yl)phenyl)-4-phenylpent-4-en-1-ol
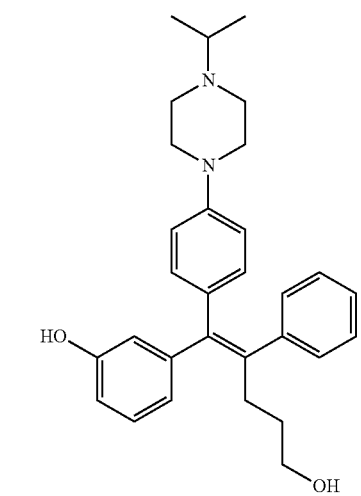
Compound 22i (DMRC200699)
(E)-5-(4-hydroxyphenyl)-5-(4-(N-cyclopropylpiperidin-4-yl)phenyl)-4-phenylpent-4-en-1-ol
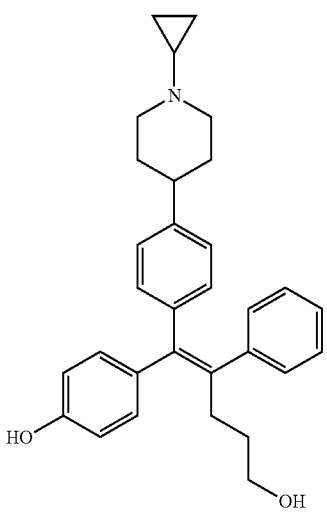

Compound 22r (DMRC200996)
(E)-5-(5-hydroxyphenyl)-5-(4-(N-cyclopropylpiperidin-4-yl)phenyl)-4-phenylpent-4-en-1-ol

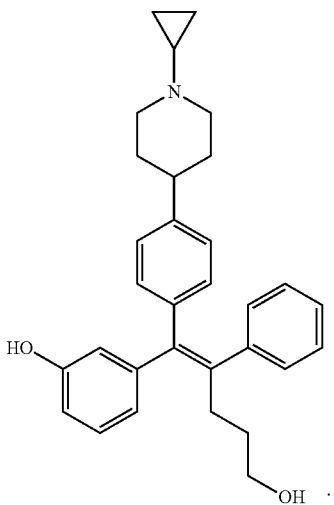 [SMILES: OCCC/C(=C(/c1ccc(C2CCN(C3CC3)CC2)cc1)c1cccc(O)c1)c1ccccc1]

The pharmaceutical composition according to an embodiment comprises a compound as described above, or a pharmaceutically acceptable salt thereof, or a solvate thereof, or an isomer thereof, as an active ingredient. The pharmaceutical composition may include a pharmaceutically acceptable carrier, excipient, or additive, known in the art.

Methods of Use

In general, the disclosure relates to methods or uses for treating pancreatitis, in particular acute pancreatitis, which comprises administering aryl ethene compounds of Chemical Formula 1 or a pharmaceutically acceptable salt, or a pharmaceutical composition thereof.

The methods of treatment according to an embodiment comprise administering a therapeutically effective amount of a compound of Chemical Formula 1, or a pharmaceutically acceptable salt thereof, or a pharmaceutical composition thereof, to a patient in need thereof. Individual embodiments include methods of treating pancreatitis by administering a therapeutically effective amount of a compound of Chemical Formula 1, or a pharmaceutically acceptable salt thereof, or a pharmaceutical composition thereof, to a patient in need thereof.

As used herein, "pancreatitis" may include a chronic pancreatitis or acute pancreatitis. The term "acute pancreatitis" as used herein may include severe acute pancreatitis that may be associated with organ failure and/or local complications such as necrosis, abscess, or pseudocyst as well as mild acute pancreatitis that may be associated with minimal organ dysfunction and an uneventful recovery and lacks the features of severe acute pancreatitis.

As used herein, "treat" or "treatment" in reference to a disorder means: (1) to ameliorate the disorder or one or more of the biological manifestations of the disorder, (2) to interfere with (a): one or more points in the biological cascade that leads to or is responsible for the disorder, or (b): one or more of the biological manifestations of the disorder, (3) to alleviate one or more of the symptoms or effects associated with the disorder, or (4) to slow the progression of the disorder or one or more of the biological manifestations of the disorder.

The term "treatment" of a disorder may include prevention or prophylaxis of the disorder. The term "prevention" refers to a prophylactic administration of a drug to substantially diminish the likelihood or severity of a disorder or biological manifestation thereof, or to delay the onset of such disorder or biological manifestation thereof.

The term "effective amount" as used herein in reference to a compound of Chemical Formula 1, or a pharmaceutically acceptable salt thereof, or other pharmaceutically active agent means an amount of the compound sufficient to treat the patient's condition within the scope of sound medical judgment. An effective amount of a compound will vary with the particular compound chosen (for example, the potency, efficacy, and half-life of the compound will be considered); the route of administration chosen; the disorder being treated; the severity of the disorder being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

The term "patient" or "subject" as used herein refers to a human or other mammal. In one embodiment, "patient" refers to a human.

An embodiment of the disclosure further provides a method for the treatment of acute pancreatitis, which method comprises administering to a patient in need thereof an effective amount of a compound of Chemical Formula 1, a pharmaceutically acceptable salt thereof, or a solvate thereof.

In one embodiment there is provided a method for the treatment of acute pancreatitis, which method comprises administering to a patient in need thereof a therapeutically effective amount of a compound of Chemical Formula 1, a pharmaceutically acceptable salt thereof, or a solvate thereof.

In one embodiment there is provided a method for the treatment of acute pancreatitis, which method comprises administering to a patient in need thereof a therapeutically effective amount of (E)-5-(4-hydroxyphenyl)-5-(4-(4-isopropylpiperazin-1-yl)phenyl)-4-phenylpent-4-en-1-ol (Compound DMRC200344 or 18a) or a pharmaceutically acceptable salt thereof or a solvate thereof.

In another embodiment there is provided a method for the treatment of acute pancreatitis, which method comprises administering to a patient in need thereof a therapeutically effective amount of (E)-5-(5-hydroxyphenyl)-5-(4-(4-isopropylpiperazin-1-yl)phenyl)-4-phenylpent-4-en-1-ol (Compound DMRC2001000 or 18k), a pharmaceutically acceptable salt thereof, or a solvate thereof.

In another embodiment there is provided a method for the treatment of acute pancreatitis, which method comprises administering to a patient in need thereof a therapeutically effective amount of (E)-5-(4-hydroxyphenyl)-5-(4-(N-cyclopropylpiperidin-4-yl)phenyl)-4-phenylpent-4-en-1-ol (Compound DMRC200699 or 22i), a pharmaceutically acceptable salt thereof, or a solvate thereof.

In another embodiment there is provided a method for the treatment of acute pancreatitis, which method comprises administering to a patient in need thereof a therapeutically effective amount of (E)-5-(5-hydroxyphenyl)-5-(4-(N-cyclopropylpiperidin-4-yl)phenyl)-4-phenylpent-4-en-1-ol (Compound DMRC200699 or 22r), a pharmaceutically acceptable salt thereof, or a solvate.

In a further aspect, there is provided a compound of Chemical Formula 1, a pharmaceutically acceptable salt thereof, or a solvate thereof for use in therapy.

In one embodiment there is provided a compound of Chemical Formula 1, a pharmaceutically acceptable salt thereof, or a solvate thereof for use in the treatment of acute pancreatitis.

In one embodiment there is provided the use of a compound of Chemical Formula 1, a pharmaceutically acceptable salt thereof, or a solvate thereof, in the manufacture of a medicament for use in the treatment of acute pancreatitis.

In one embodiment there is provided the use of (E)-5-(4-hydroxyphenyl)-5-(4-(4-isopropylpiperazin-1-yl)phenyl)-4-phenylpent-4-en-1-ol (DMRC200344 or 18a), a pharmaceutically acceptable salt thereof, or a solvate thereof, in the manufacture of a medicament for use in the treatment of acute pancreatitis.

In one embodiment there is provided the use of (E)-5-(5-hydroxyphenyl)-5-(4-(4-isopropylpiperazin-1-yl)phenyl)-4-phenylpent-4-en-1-ol (DMRC2001000 or 18k), a pharmaceutically acceptable salt thereof, or a solvate thereof, in the manufacture of a medicament for use in the treatment of acute pancreatitis.

In one embodiment there is provided the use of (E)-5-(4-hydroxyphenyl)-5-(4-(N-cyclopropylpiperidin-4-yl)phenyl)-4-phenylpent-4-en-1-ol (DMRC200699 or 22i), a pharmaceutically acceptable salt thereof, or a solvate thereof, in the manufacture of a medicament for use in the treatment of acute pancreatitis.

In one embodiment there is provided the use of (E)-5-(5-hydroxyphenyl)-5-(4-(N-cyclopropylpiperidin-4-yl)phenyl)-4-phenylpent-4-en-1-ol (DMRC200699 or 22r), a pharmaceutically acceptable salt thereof, or a solvate thereof, in the manufacture of a medicament for use in the treatment of acute pancreatitis.

In one aspect, the disclosure relates to a method or use for treating pancreatitis, which comprises administering a compound of Chemical Formula 6:

Chemical Formula 6

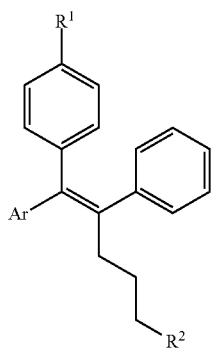

wherein
$R^1$ is (C3-C10)heterocycloalkyl or —O—(CH2)$_m$-$R^{11}$;
$R^{11}$ is (C3-C10)heterocycloalkyl;
m is an integer of 1 to 3;
Ar is s (C6-C12)aryl or (C3-C12)heteroaryl,
wherein the heterocycloalkyl, the aryl, or heteroaryl may be further substituted by one or more selected from the group consisting of hydroxy, halogen, (C1-C10)alkyl, halo(C1-C10)alkyl, (C1-C10)alkoxy, nitro, cyano, amino, (C1-C10)alkylsulfonylamino, (C3-C10)cycloalkylsulfonylamino, di((C1-C10)alkyl sulfonyl)amino, (C1-C10)alkylcarbonyloxy, (C1-C10)alkylcarbonylamino, guanidino, (C1-C10)alkyl sulfonyl, (C1-C10)alkylsulfonyloxy, halo(C1-C10)alkylsulfonyloxy, and (C3-C10)cycloalkylsulfonyloxy; and $R^2$ is hydroxyl, halogen, (C1-C10) alkyl carbonyl oxy, or (C1-C10)alkylsulfonyloxy, a pharmaceutically acceptable salt thereof or a solvate thereof to a patient in need thereof. In an embodiment, the pancreatitis is acute pancreatitis.

In another aspect, the present disclosure relates to a method or use for treating pancreatitis, which comprises administering a compound of Chemical Formula 6, wherein $R^2$ is hydroxyl, and $R^1$ is a heterocycloalkyl group selected from the following structures:

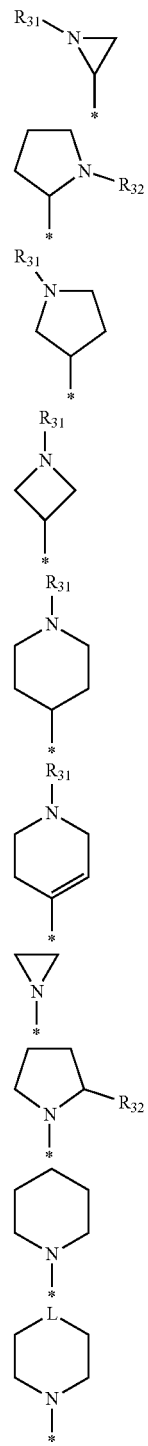

-continued

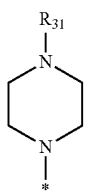

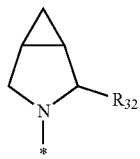

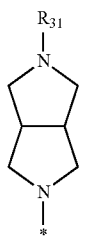

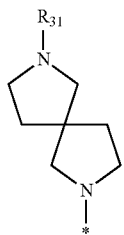

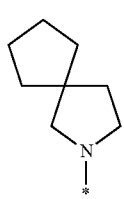

wherein $R^{31}$ and $R^{32}$ are independently hydrogen, (C1-C10)alkyl, (C3-10)cycloalkyl, (C2-C10)alkenyl, amidino, (C1-C10)alkoxycarbonyl, hydroxy(C1-C10)alkyl, or di(C1-C10)alkylamino(C1-C10)alkyl; and L is O or S, a pharmaceutically acceptable salt thereof or a solvate thereof to a patient in need thereof. In an embodiment, the pancreatitis is acute pancreatitis.

In still another aspect, the present disclosure relates to a method or use for treating pancreatitis, which comprises administering a compound selected from the following compounds:

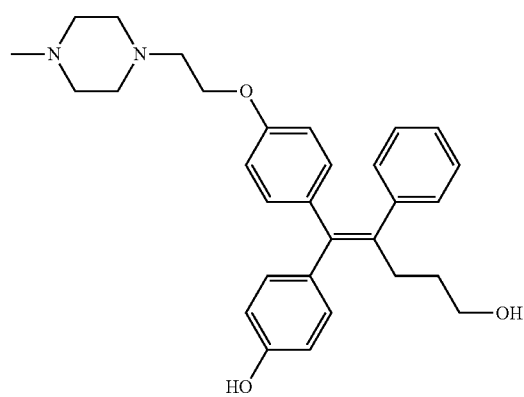

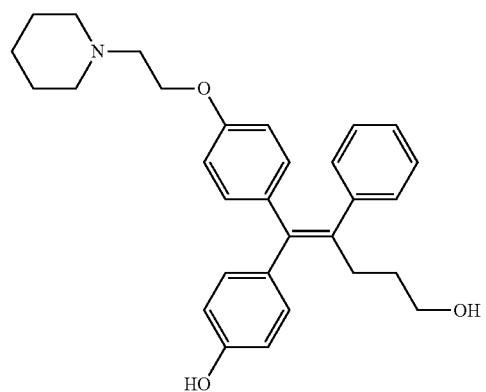

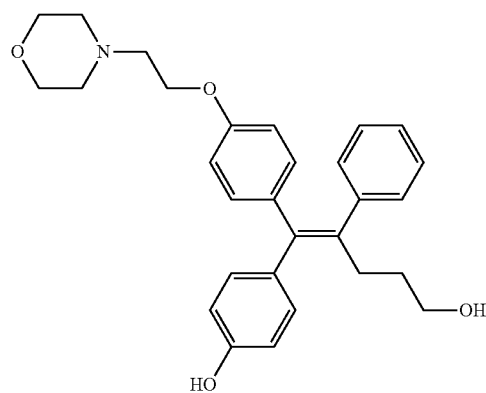

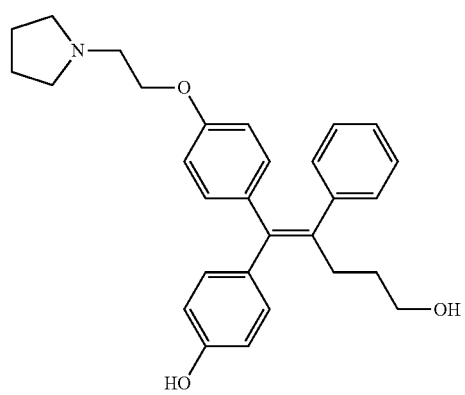

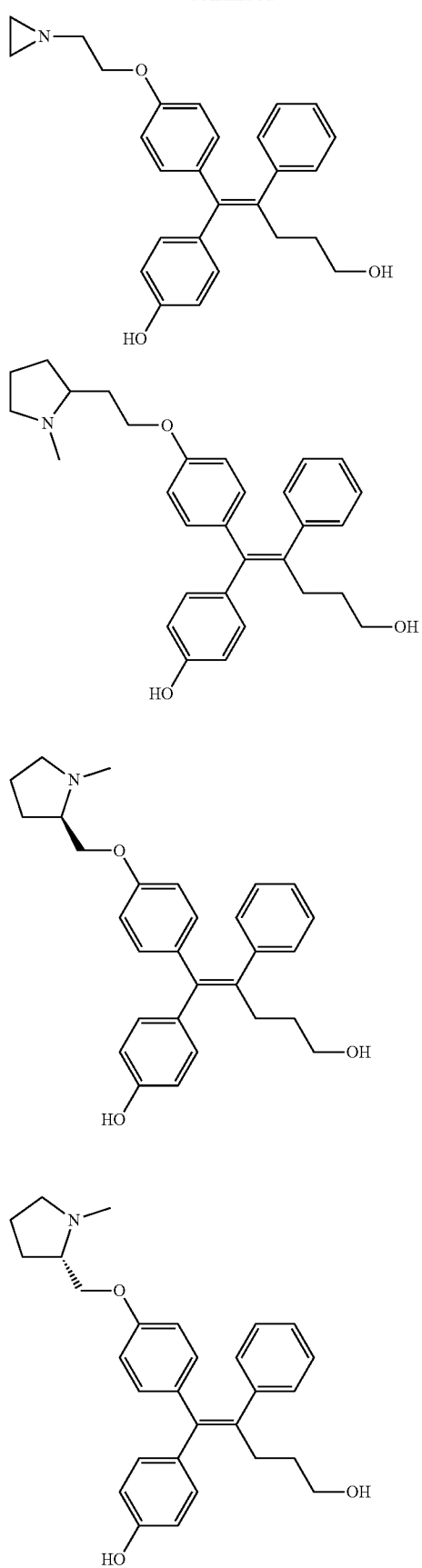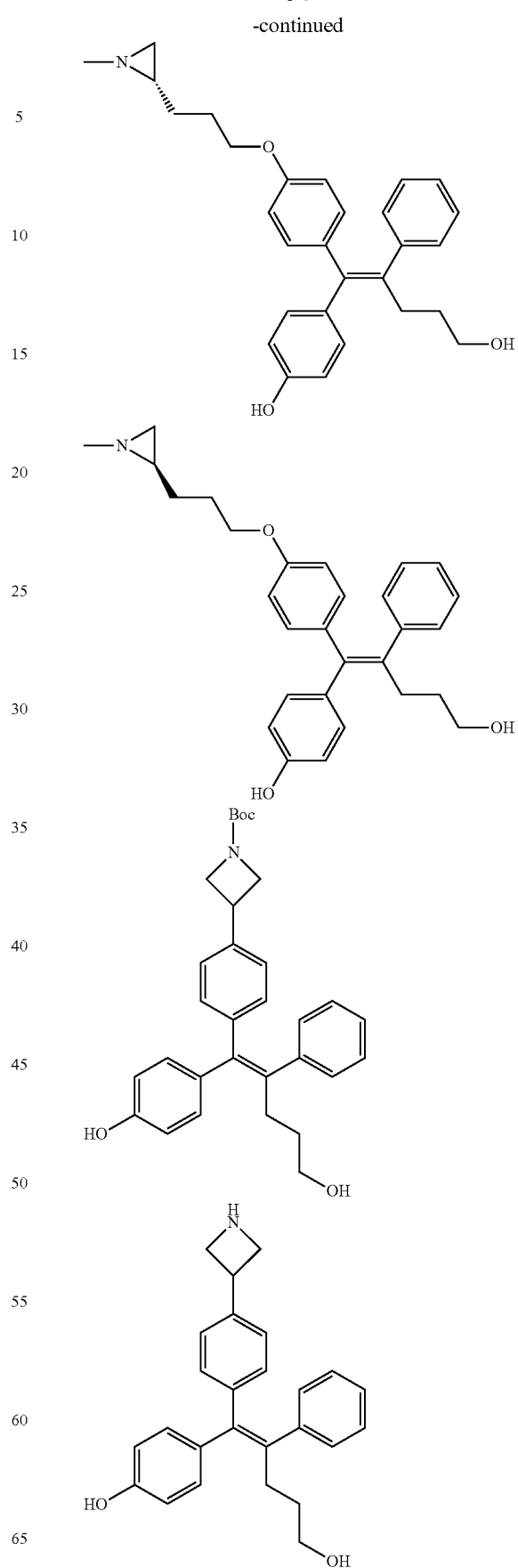

65
-continued
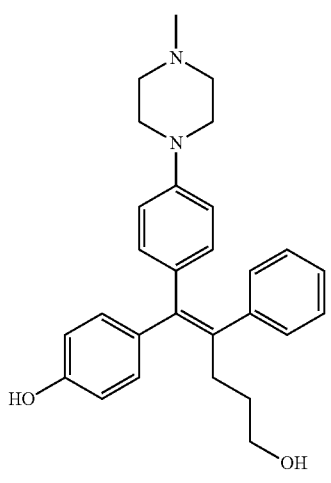
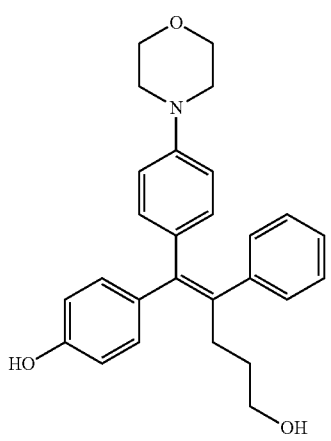
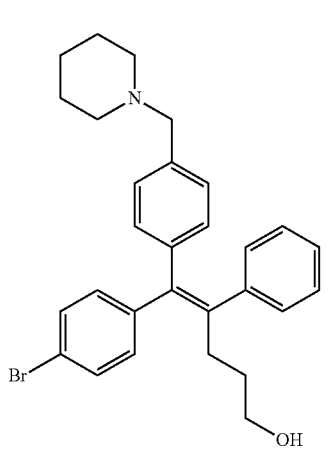
66
-continued
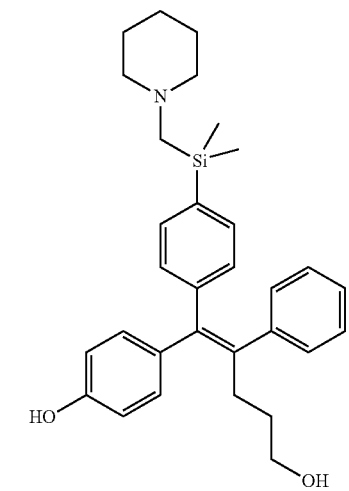
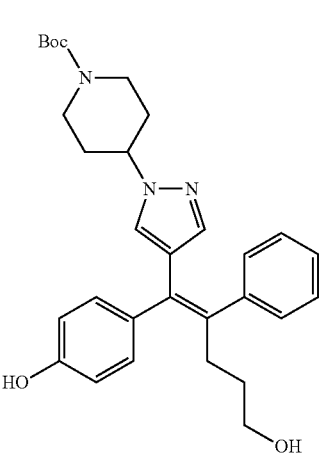
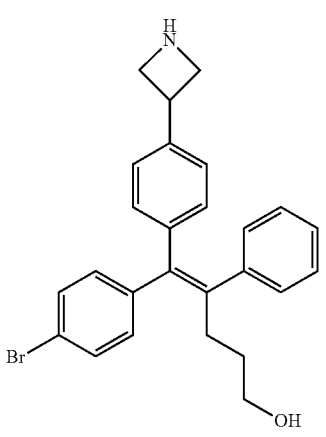

67
-continued
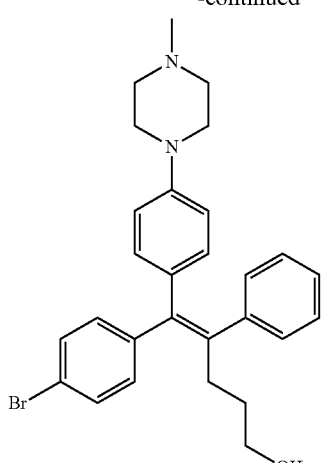
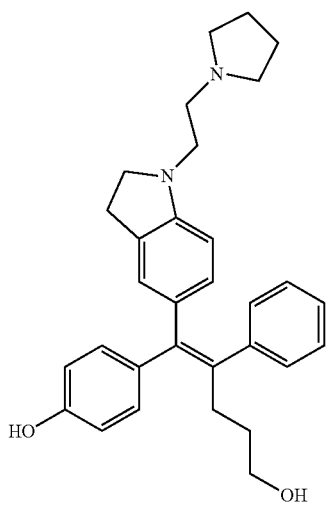
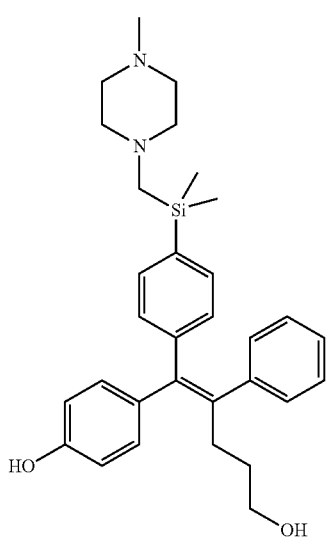
68
-continued
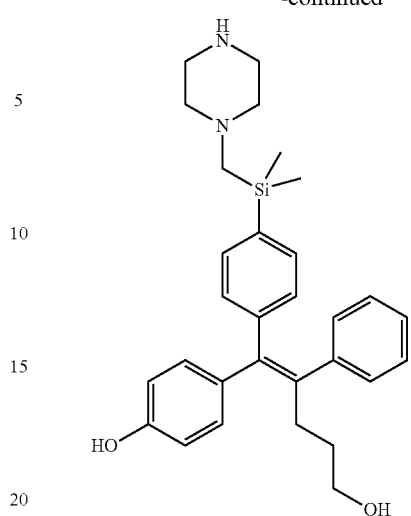
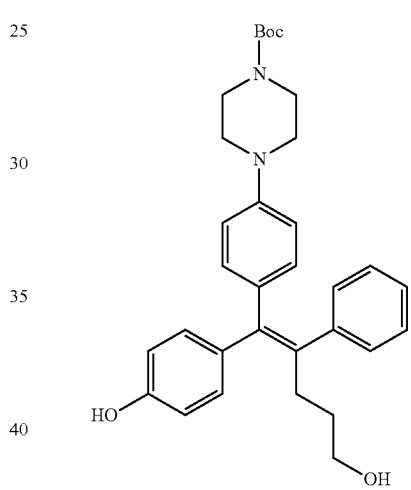
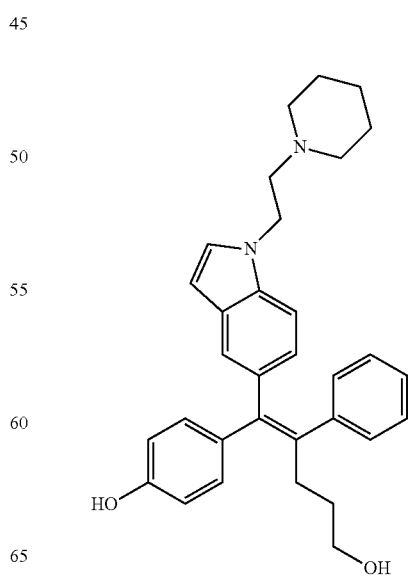

69
-continued
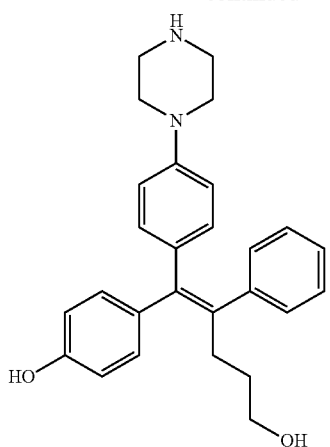
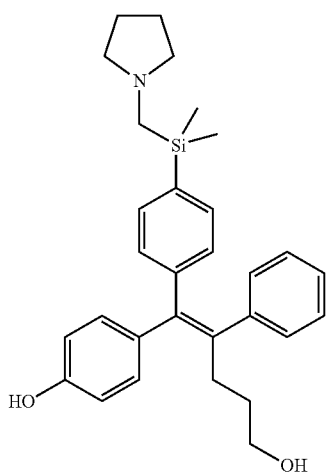
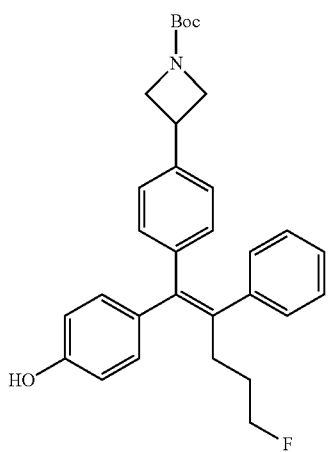
70
-continued
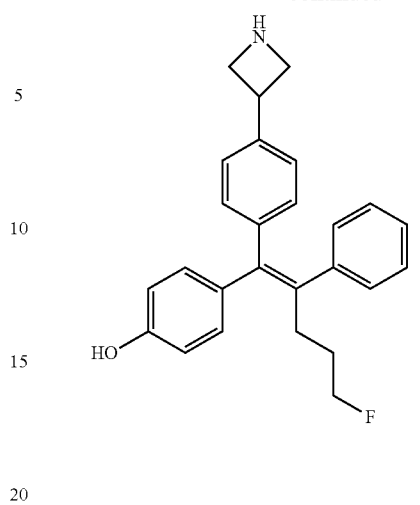
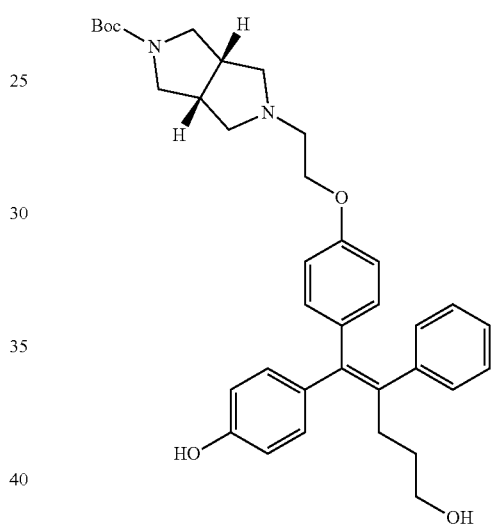
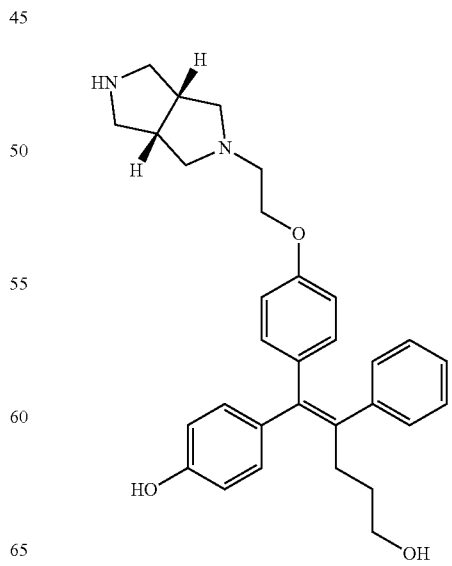

71
-continued
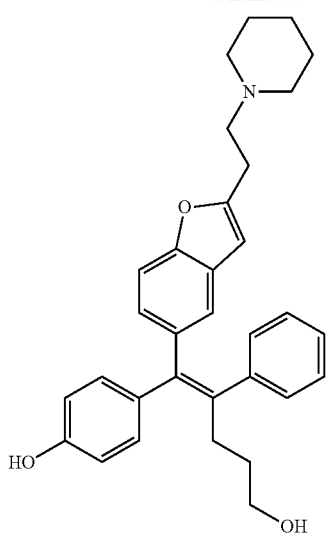
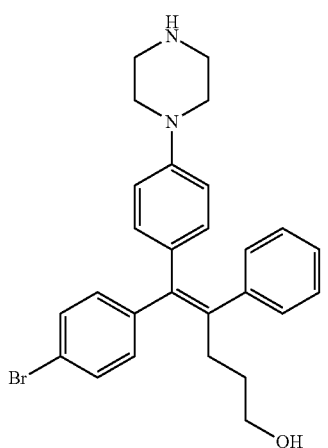
72
-continued
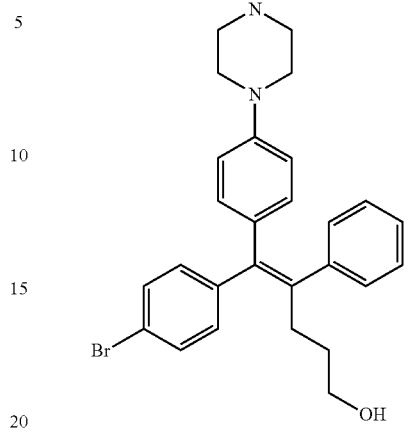
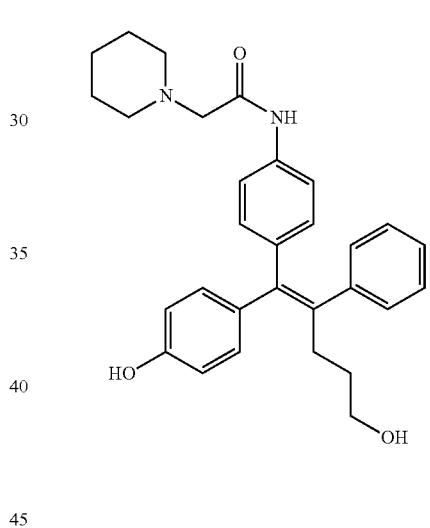
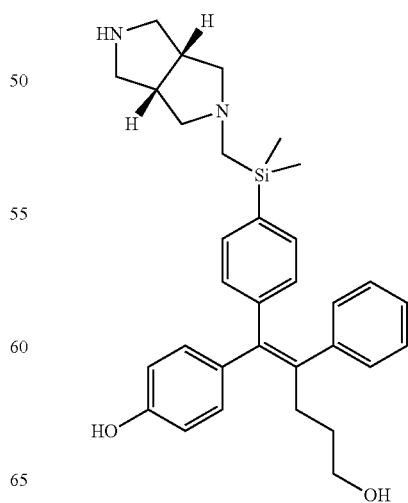

73
-continued
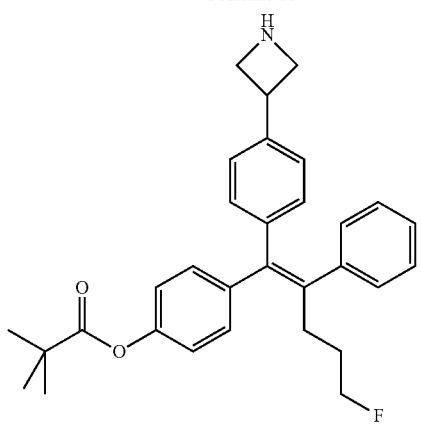
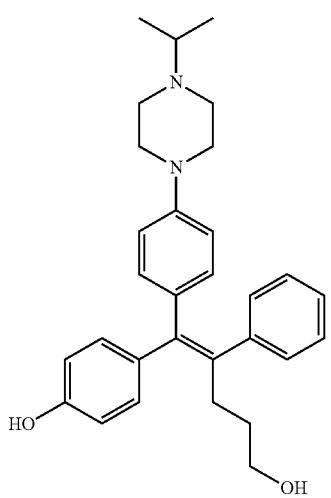 [SMILES: CC(C)N1CCN(c2ccc(/C(=C(/CCCO)c3ccccc3)c3ccc(O)cc3)cc2)CC1]
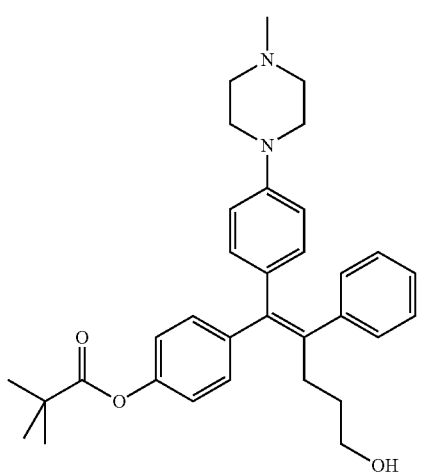
74
-continued
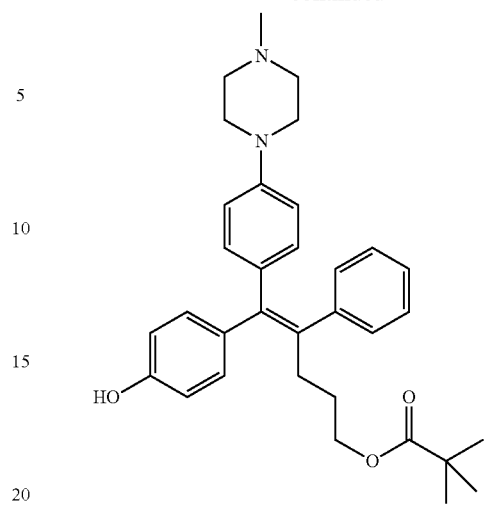
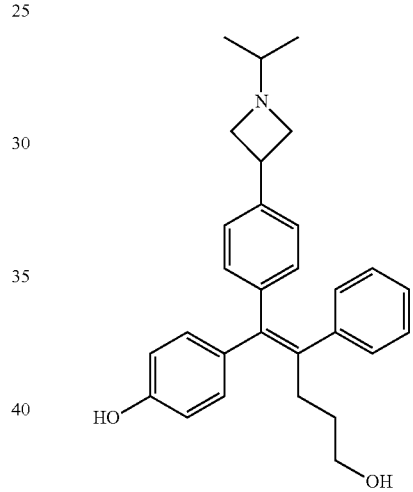
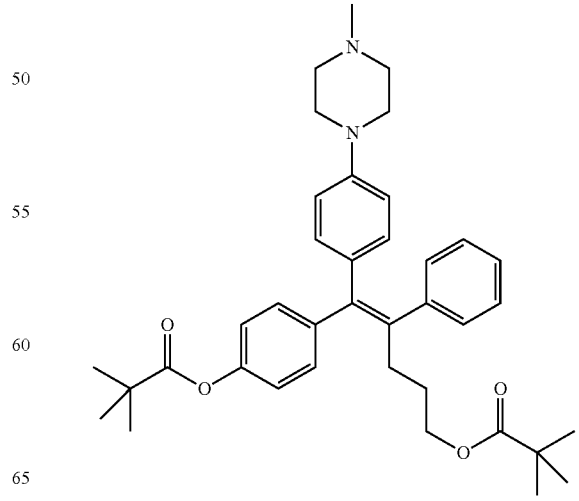

75
-continued
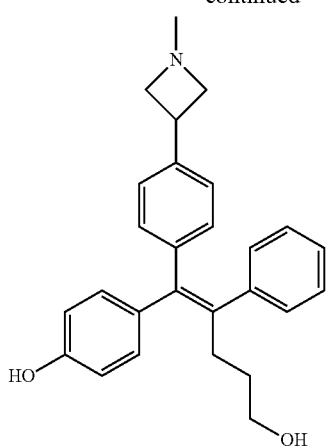
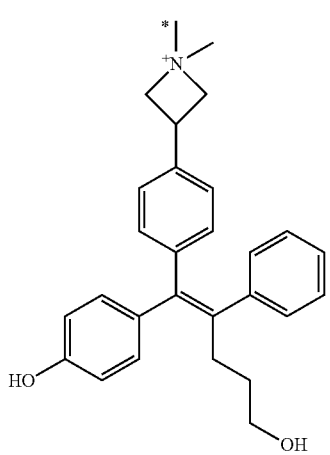
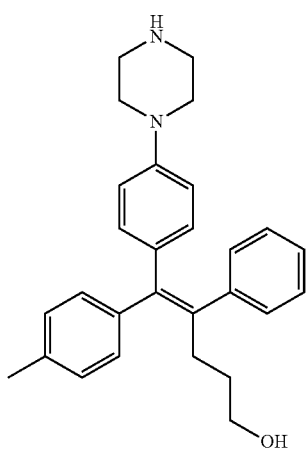
76
-continued
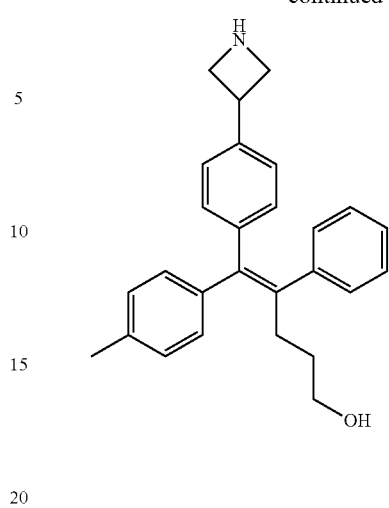
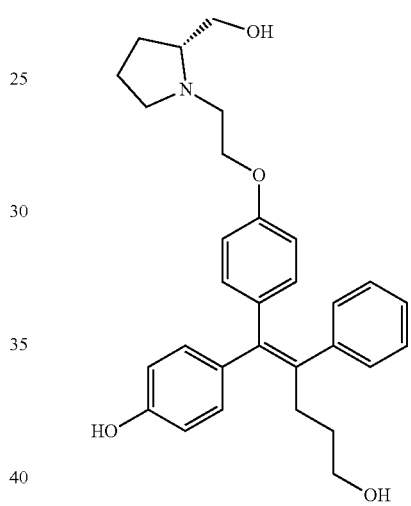
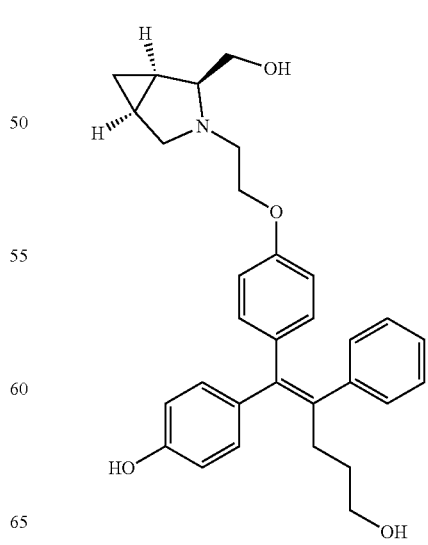

77                                          78
-continued                                  -continued
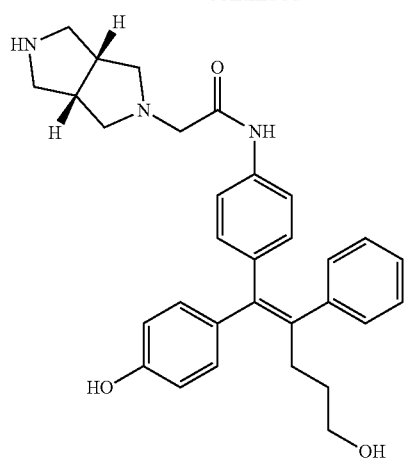
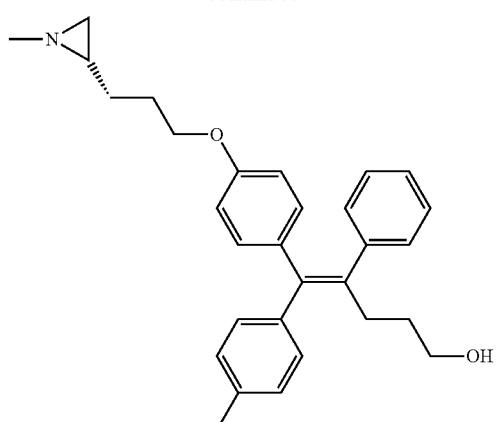
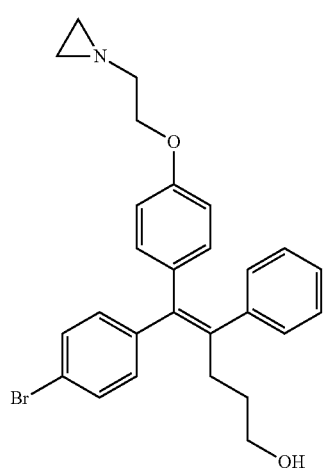
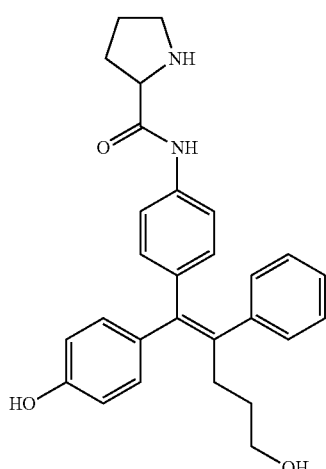
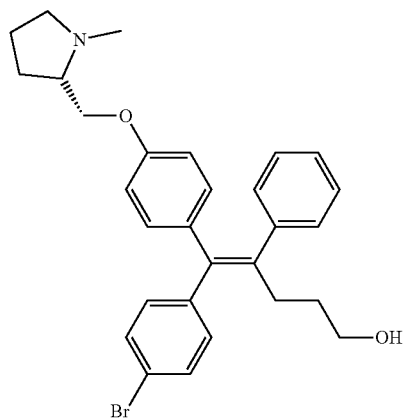
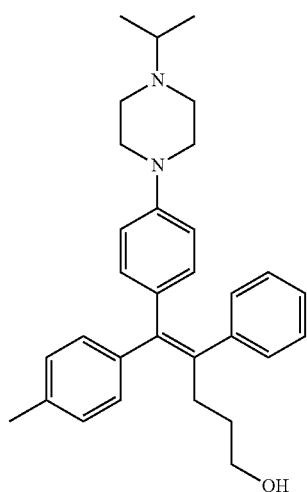

79
-continued
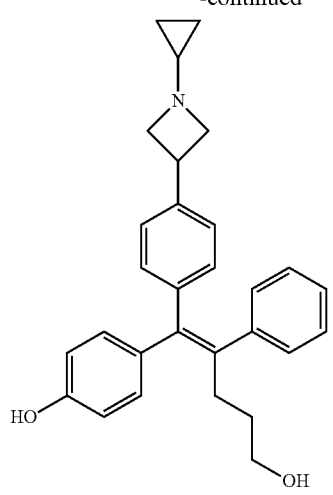
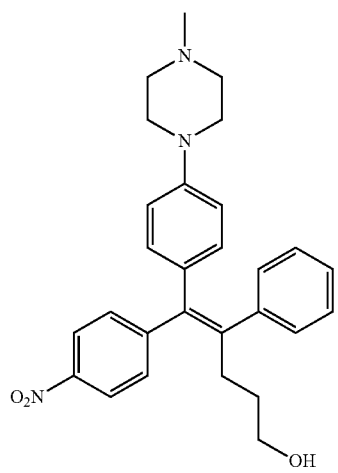
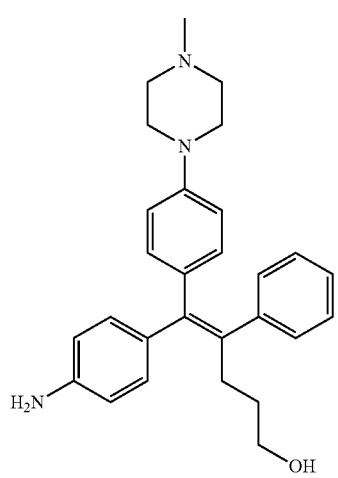
80
-continued
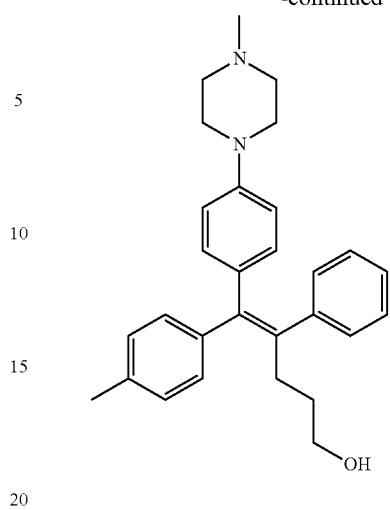
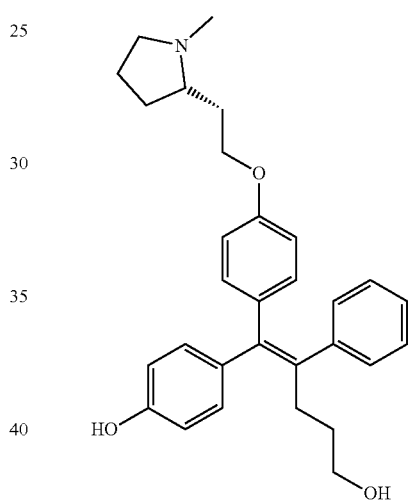
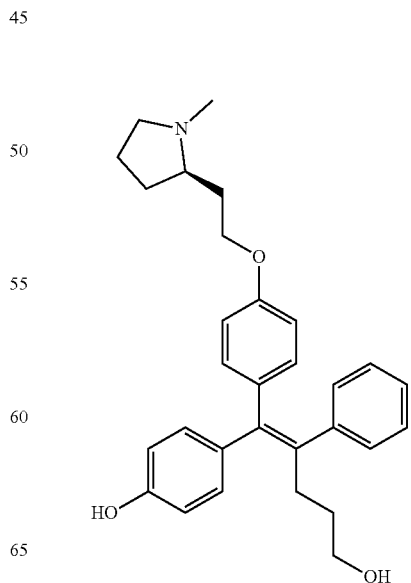

81
-continued
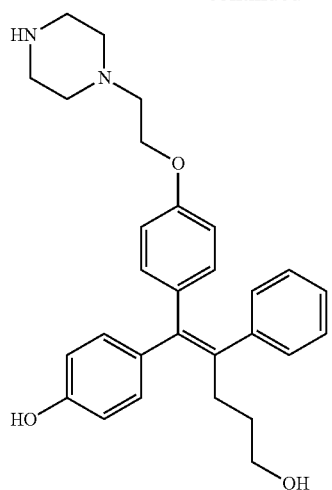
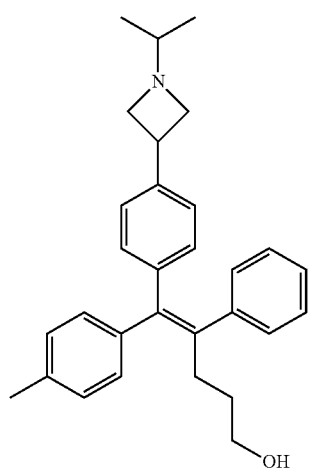
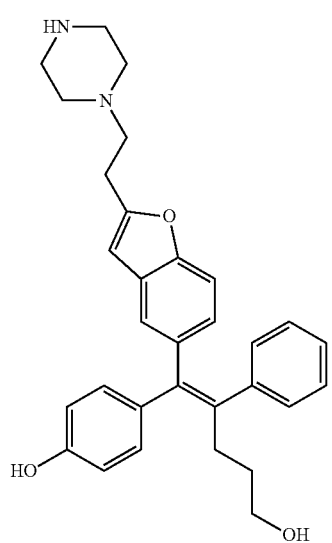
82
-continued
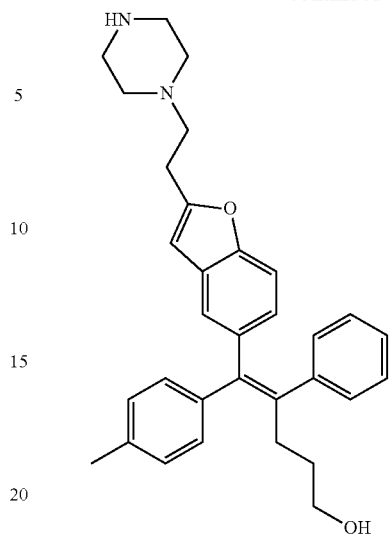
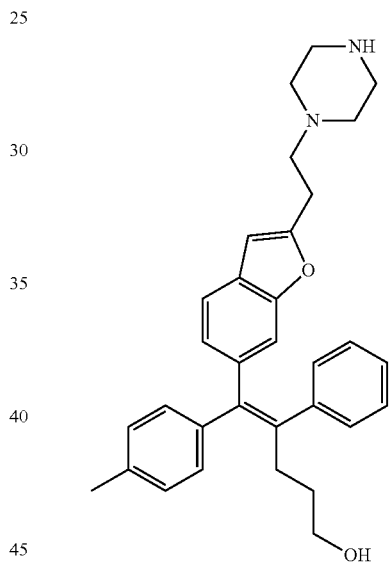
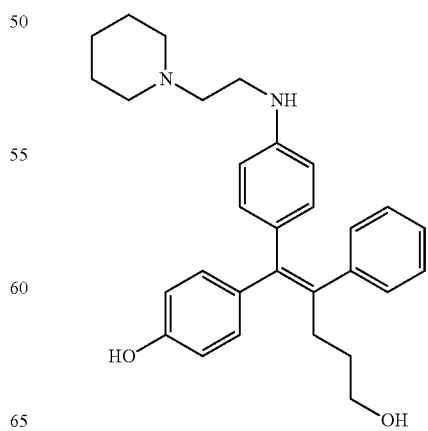

83
-continued
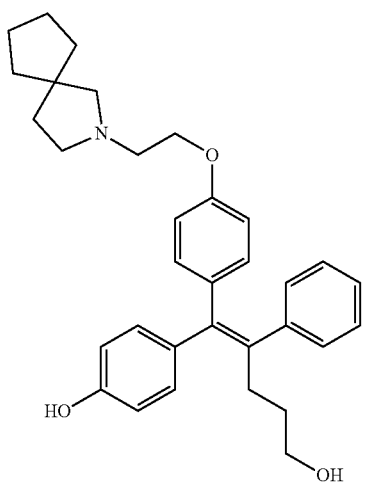
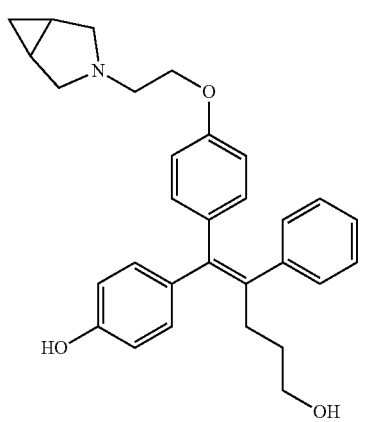
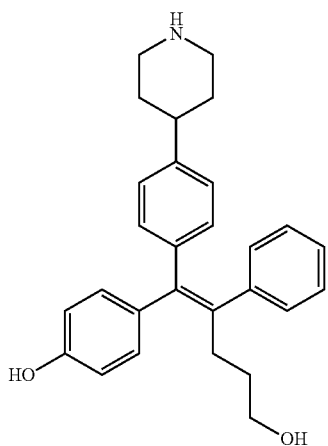
84
-continued
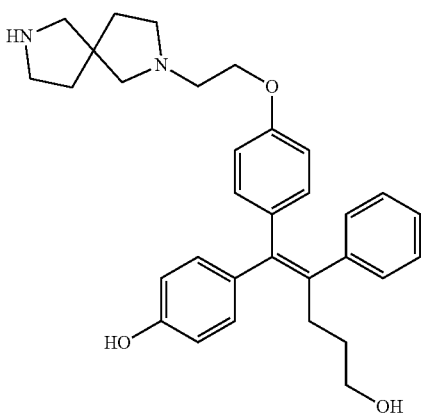
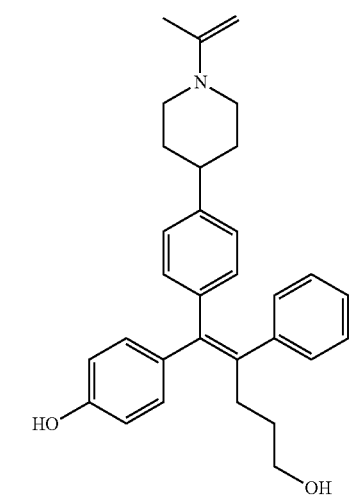
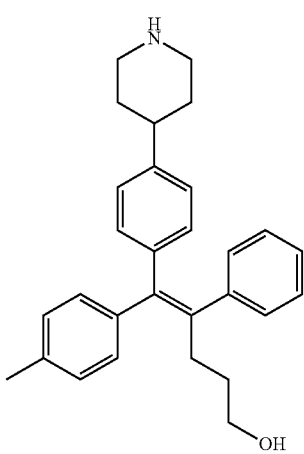

85
-continued
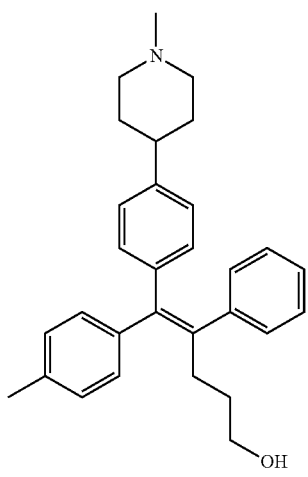
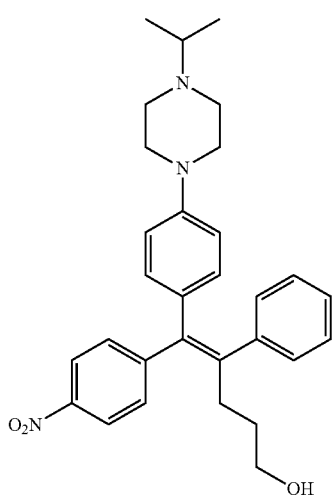
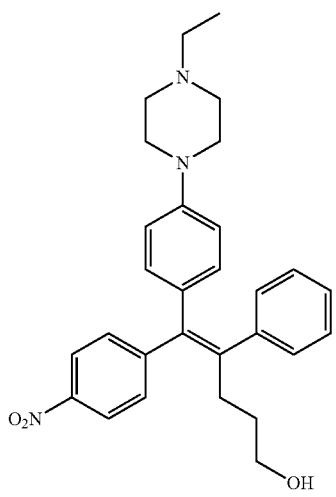
86
-continued
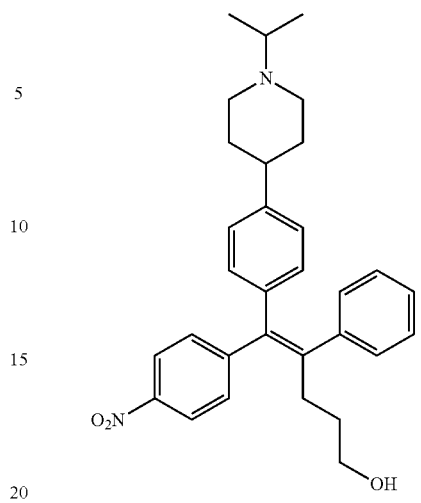
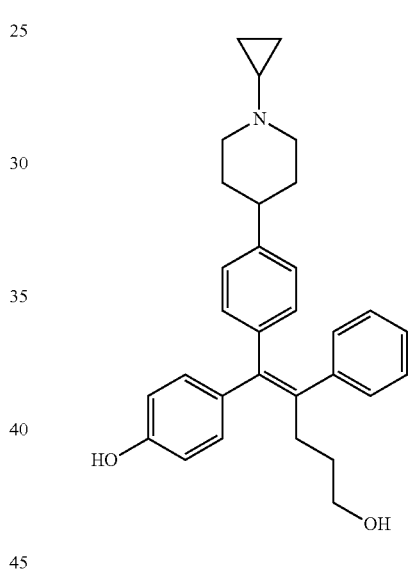
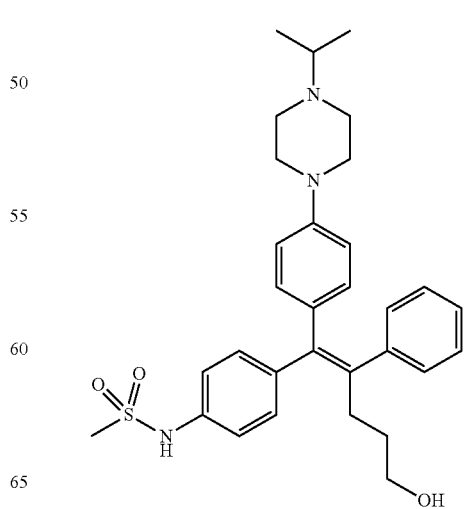

87
-continued
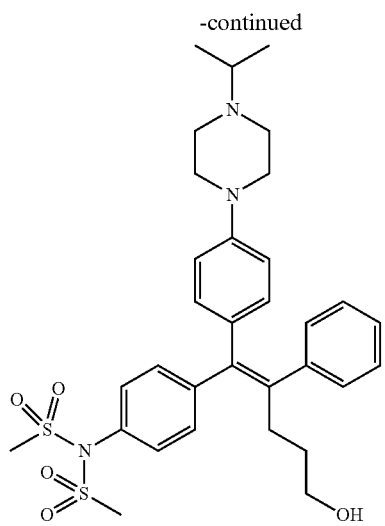
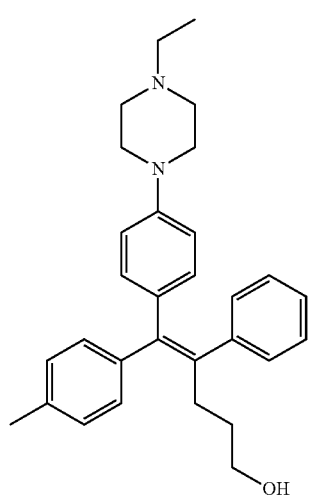
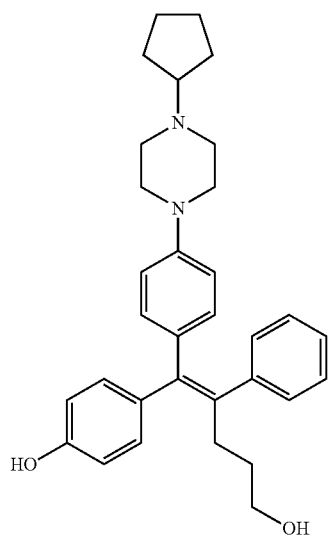
88
-continued
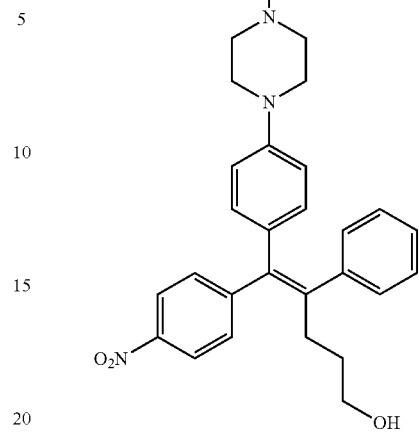
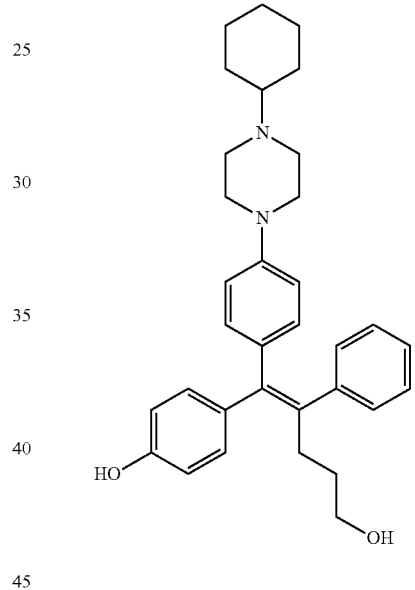
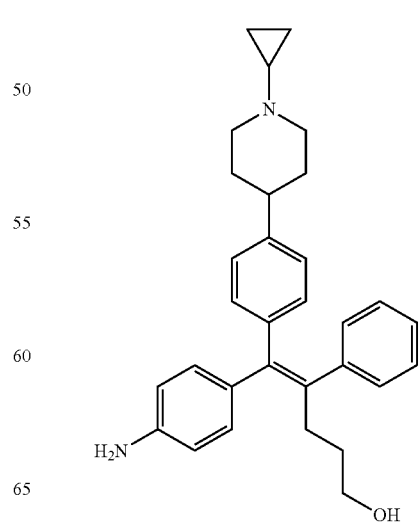

89
-continued
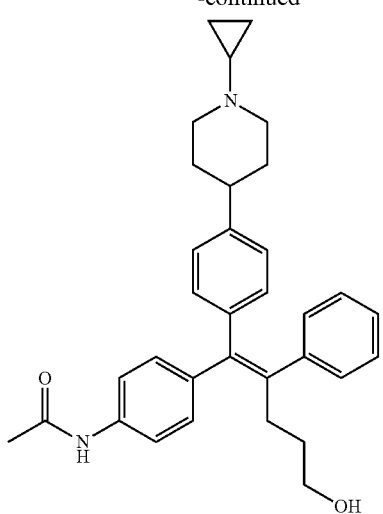
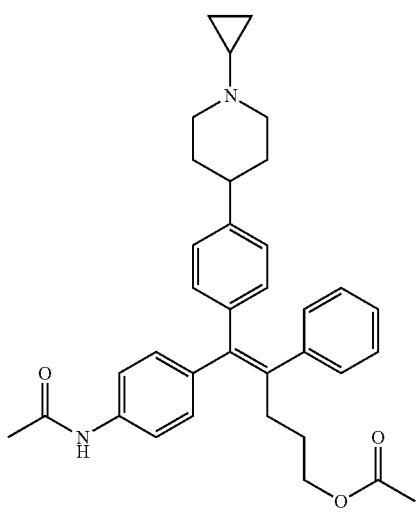
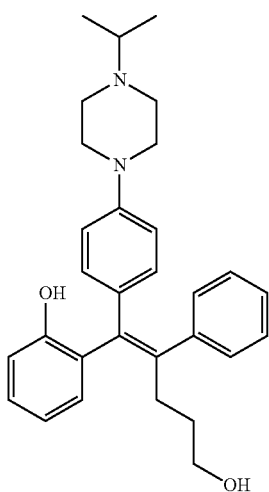
90
-continued
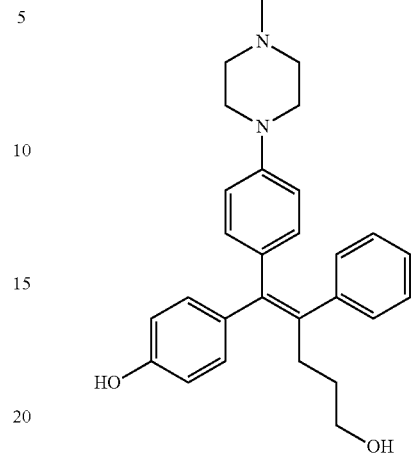
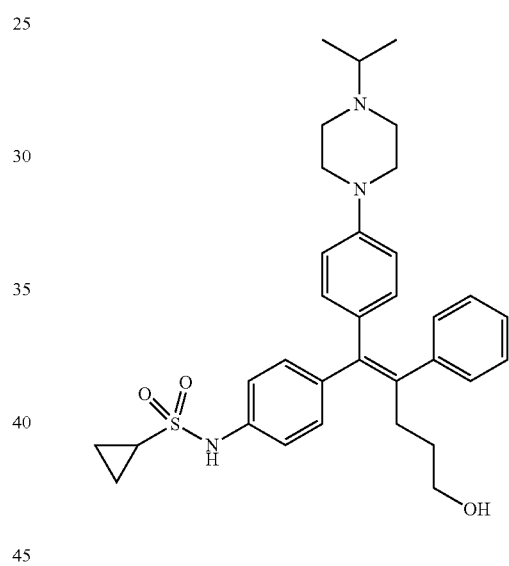
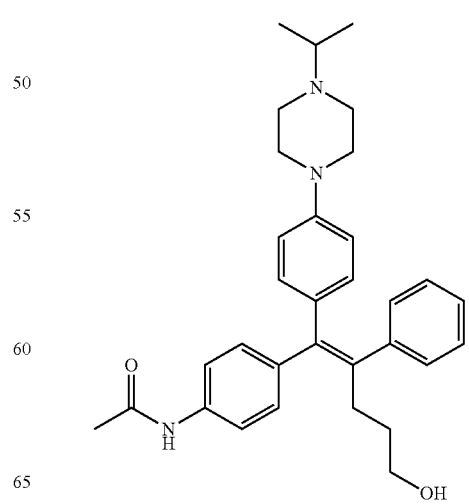

91
-continued
92
-continued
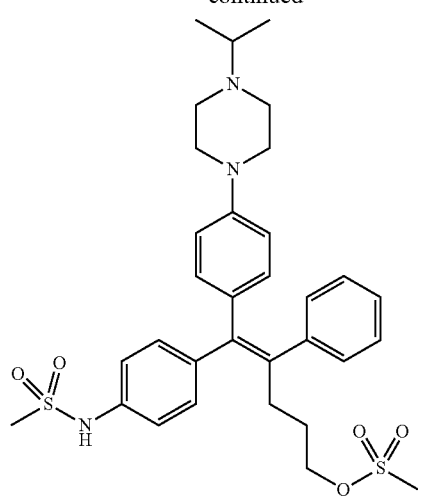
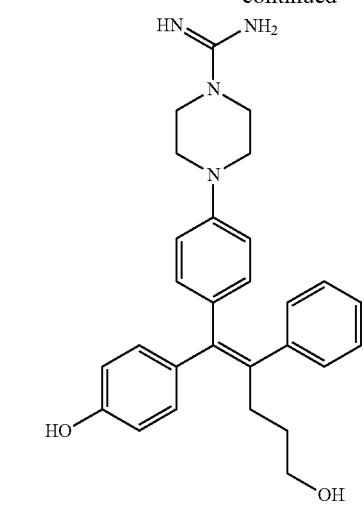
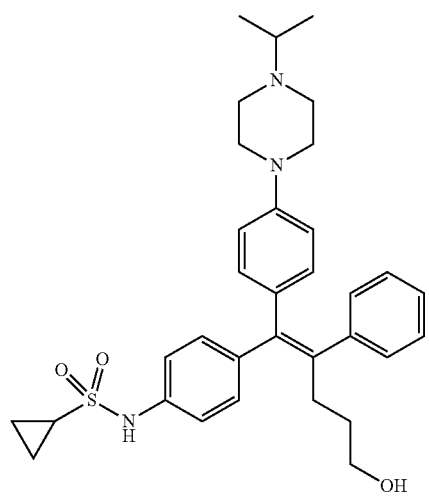
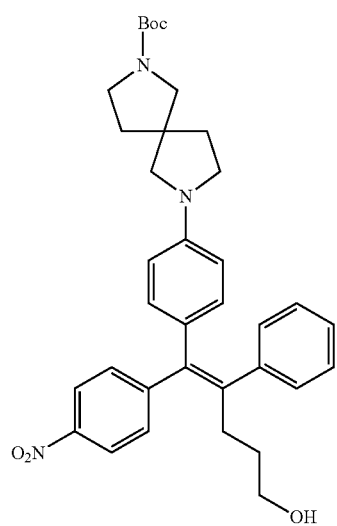
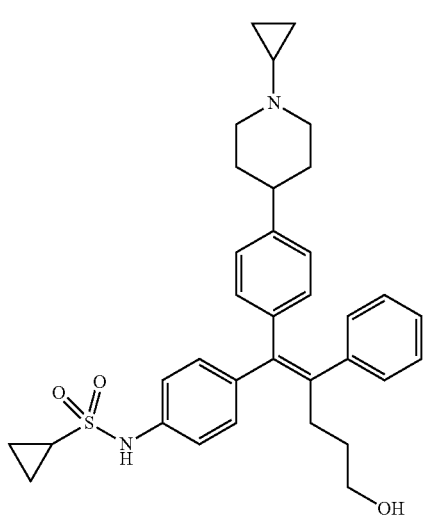

93
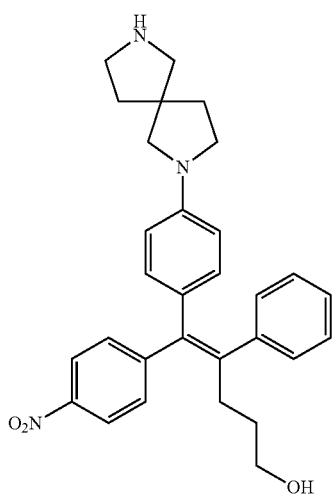
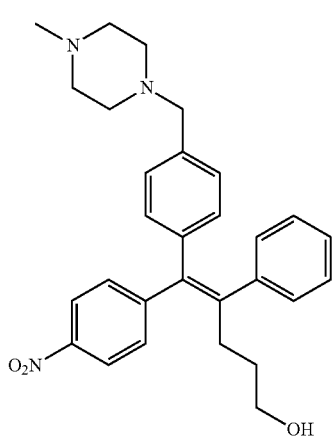
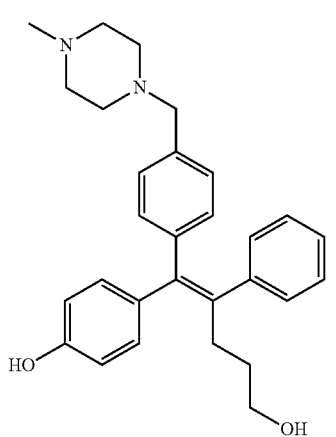
94
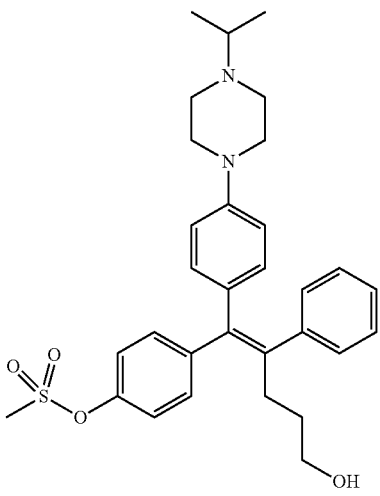
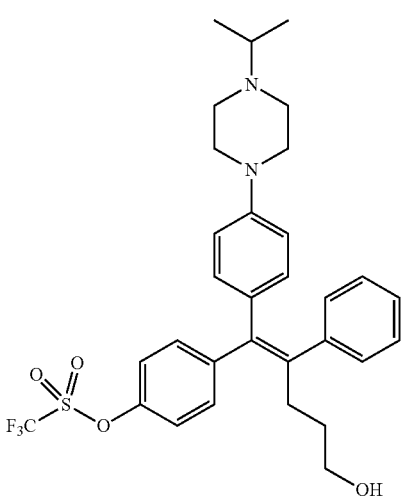
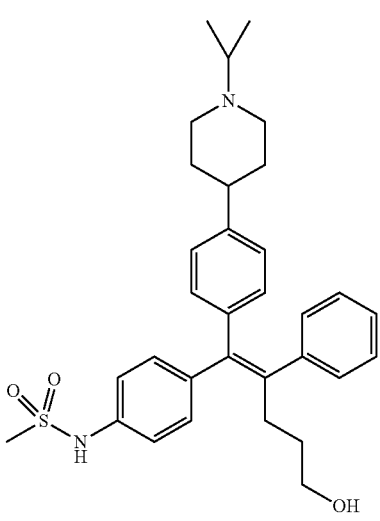

95
-continued
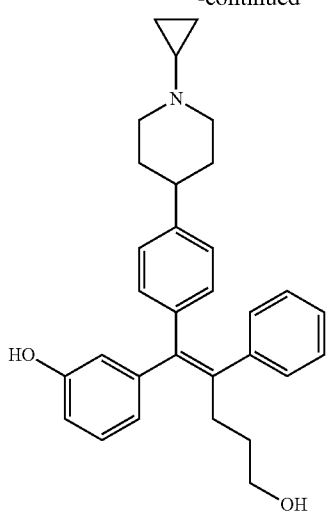
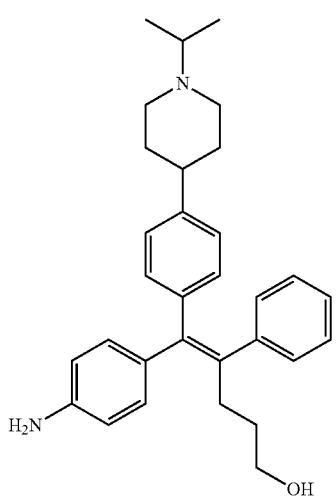
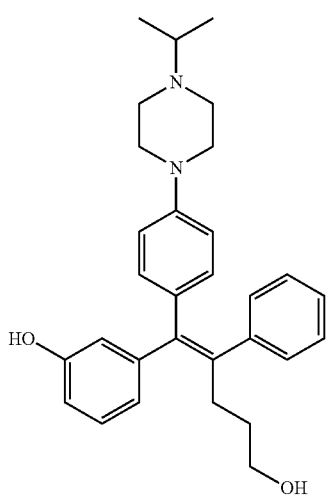 [SMILES: CC(C)N1CCN(c2ccc(/C(=C(/CCCO)c3ccccc3)c3cccc(O)c3)cc2)CC1]
96
-continued
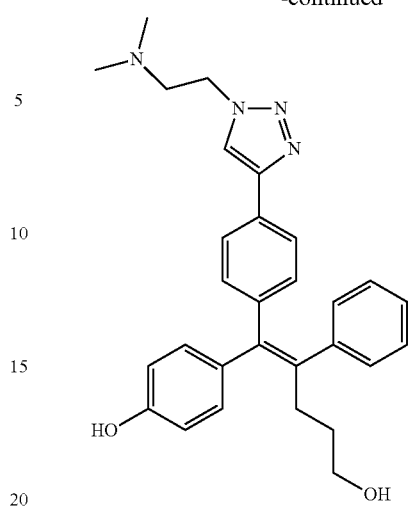
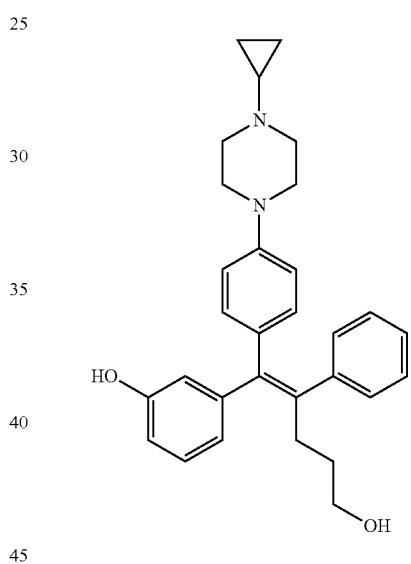
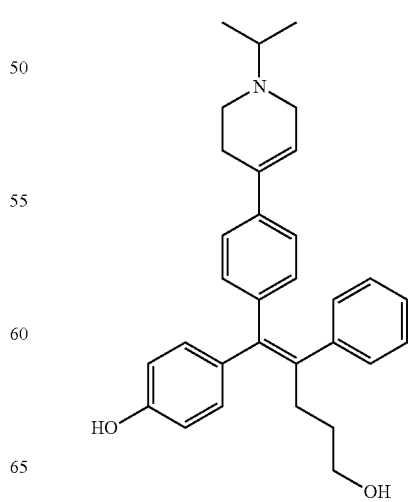

97
-continued
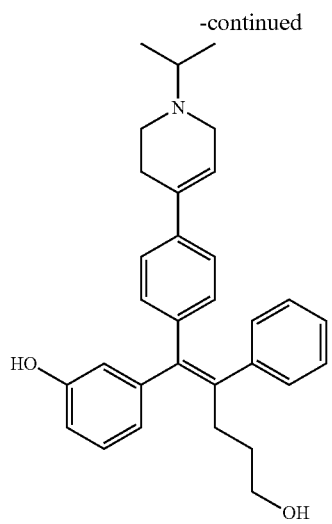
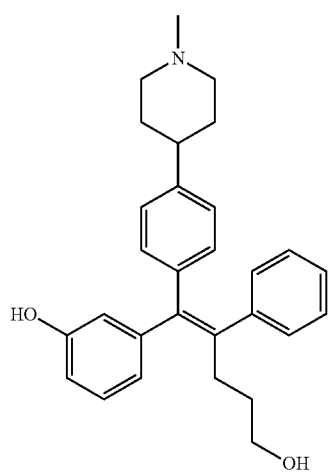
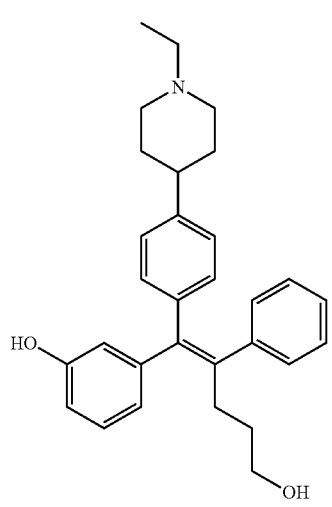
98
-continued
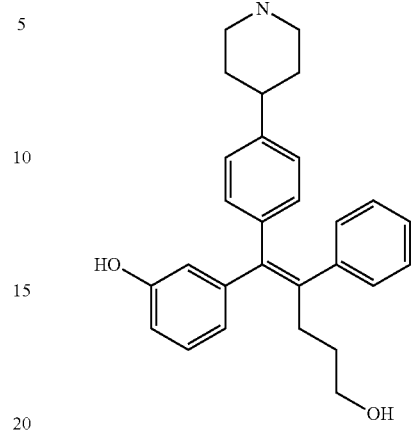
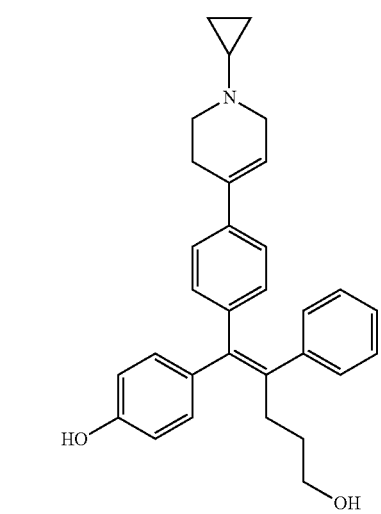 [SMILES: OCCC/C(=C(\c1ccc(O)cc1)c1ccc(C2CCN(C3CC3)CC2)cc1)c1ccccc1]
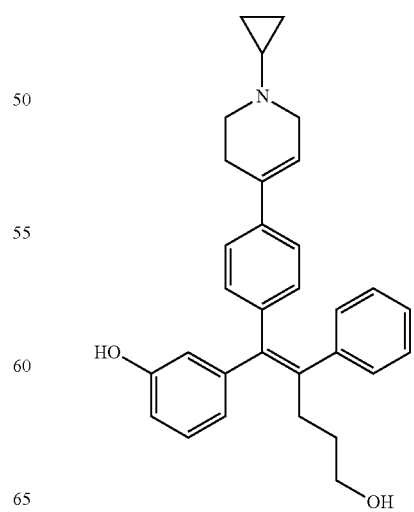

| 99 | 100 |
|---|---|
| -continued | -continued |
| 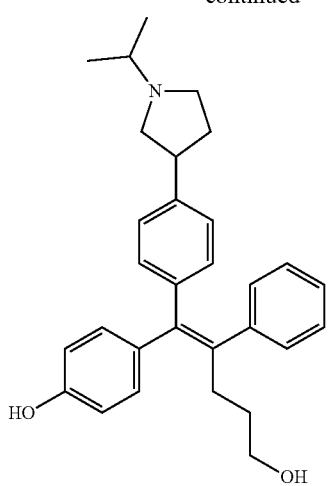 | 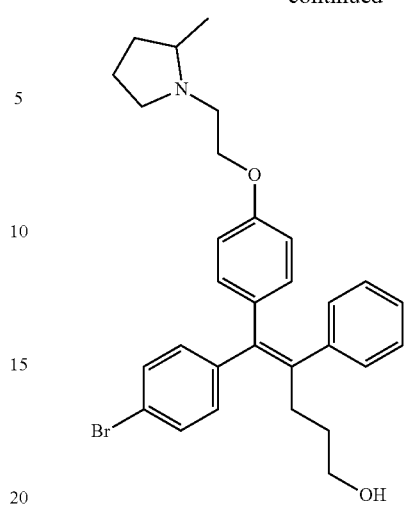 |
| 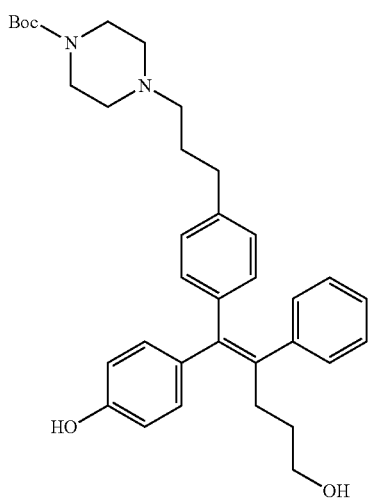 | 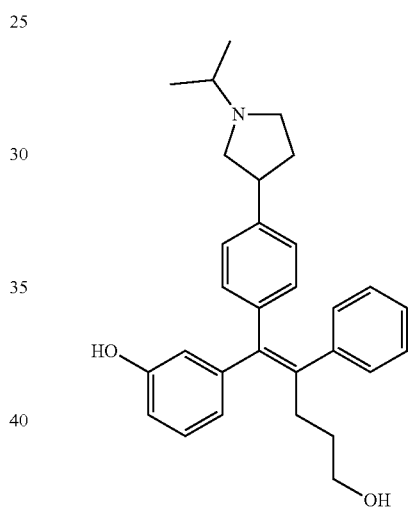 |
| 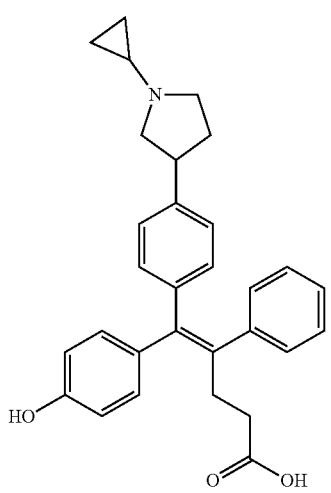 | 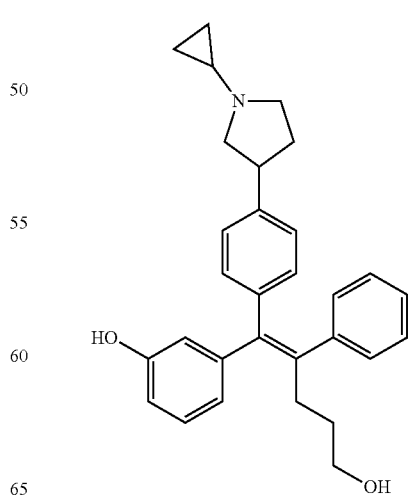 |

101
-continued
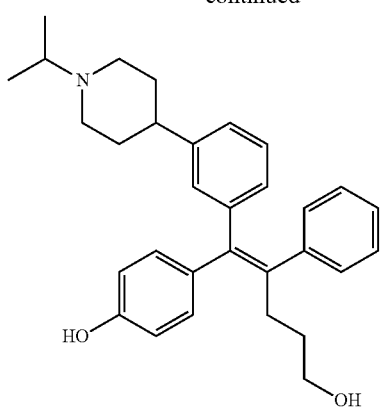
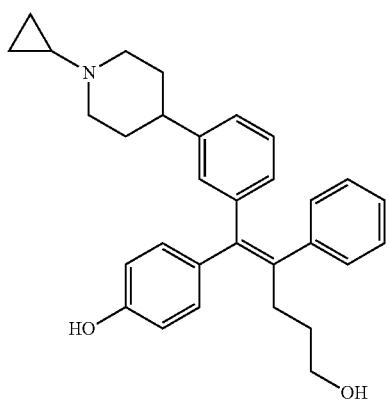
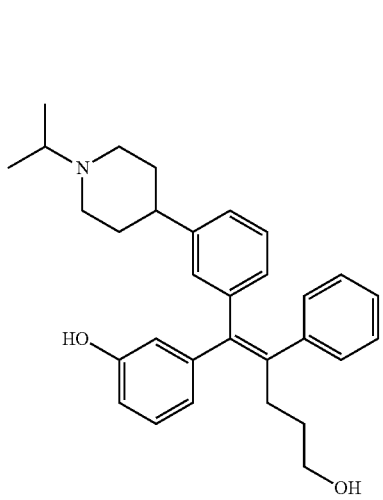
102
-continued
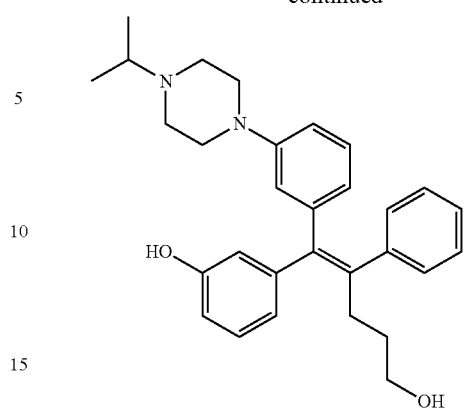
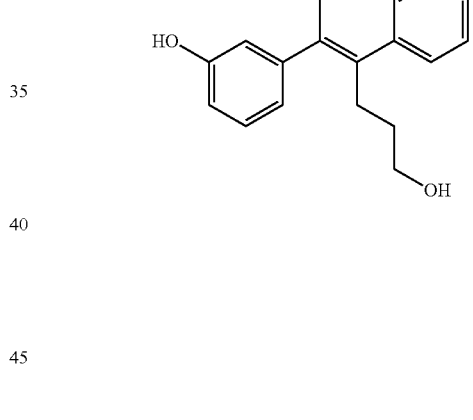
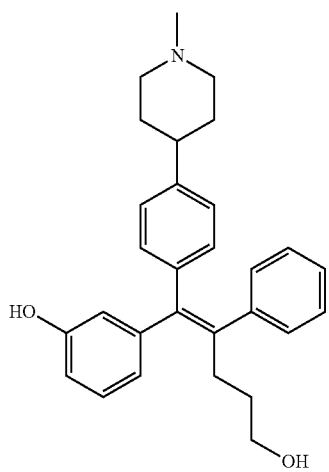

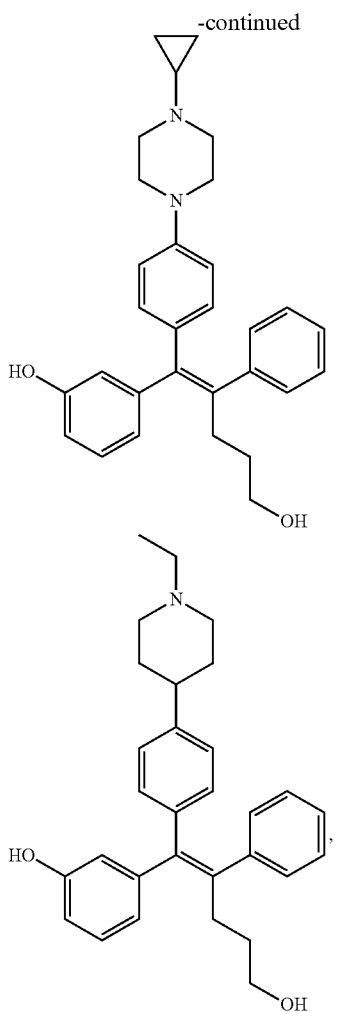

a pharmaceutically acceptable salt thereof, or a solvate thereof, a patient in need thereof. In an embodiment, the pancreatitis is acute pancreatitis.

In still another aspect, the present disclosure relates to a method or use for treating acute pancreatitis, which comprises administering (E)-5-(4-hydroxyphenyl)-5-(4-(4-isopropylpiperazin-1-yl)phenyl)-4-phenylpent-4-en-1-ol (Compound 18a, DMRC200434), (E)-5-(5-hydroxyphenyl)-5-(4-(4-isopropylpiperazin-1-yl)phenyl)-4-phenylpent-4-en-1-ol (Compound 18k, DMRC2001000), (E)-5-(4-hydroxyphenyl)-5-(4-(N-cyclopropylpiperidin-4-yl)phenyl)-4-phenylpent-4-en-1-ol (Compound 22i, DMRC200699), or (E)-5-(5-hydroxyphenyl)-5-(4-(N-cyclopropylpiperidin-4-yl)phenyl)-4-phenylpent-4-en-1-ol (Compound 22r, DMRC200996), a pharmaceutically acceptable salt thereof, or a solvate thereof, a patient in need thereof. In an embodiment, the pancreatitis is acute pancreatitis.

In an aspect, the compound of chemical formula 1 can be administered at a dose ranging from about 0.01 mg/kg to about 1,000 mg/kg, about 0.01 mg/kg to about 500 mg/kg, about 0.01 mg to about 100 mg/kg, about 0.05 mg/kg to 500 mg/kg, about 0.05 mg/kg to 100 mg/kg, about 0.01 mg/kg to about 200 mg/kg, about 0.01 mg/kg to 100 mg/kg, about 0.1 mg/kg to 500 mg/kg, about 0.1 mg/kg to 200 mg/kg, about 0.1 mg/kg to about 100 mg/kg, about 0.1 mg/kg to about 50 mg/kg, or about 0.1 mg/kg to about 10 mg/kg.

Compositions

The compounds of the disclosure may, but not necessarily, be formulated into pharmaceutical compositions prior to administration to a patient. Accordingly, in one aspect, there is provided a pharmaceutical composition comprising a compound of formula 1 or a pharmaceutically acceptable salt or solvate thereof and one or more pharmaceutically acceptable excipient or carrier. The pharmaceutical composition, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories.

Suitable pharmaceutically acceptable excipient or carrier will vary depending upon the particular dosage form chosen. In addition, suitable pharmaceutically acceptable excipient or carrier may be chosen for a particular function that they may serve in the composition. For example, certain pharmaceutically acceptable excipient or carrier may be chosen for their ability to facilitate the production of uniform dosage forms. Certain pharmaceutically acceptable excipient or carrier may be chosen for their ability to facilitate the production of stable dosage forms. Certain pharmaceutically acceptable excipient or carrier may be chosen for their ability to facilitate the carrying or transporting of the compound or compounds of formula 1 or pharmaceutically acceptable salts thereof once administered to the patient from one organ, or portion of the body, to another organ, or portion of the body. Certain pharmaceutically acceptable excipient or carrier may be chosen for their ability to enhance patient compliance.

Suitable pharmaceutically acceptable excipient or carrier includes the following types of excipients or carriers: diluents, fillers, binders, disintegrants, lubricants, glidants, granulating agents, coating agents, wetting agents, solvents, co-solvents, suspending agents, emulsifiers, sweetners, flavouring agents, flavour-masking agents, colouring agents, anti-caking agents, humectants, chelating agents, plasticisers, viscosity increasing agents, antioxidants, preservatives, stabilisers, surfactants, and buffering agents. The skilled artisan will appreciate that certain pharmaceutically acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically acceptable excipient or carrier in appropriate amounts.

The pharmaceutical composition according to an embodiment is prepared using techniques and methods known to those skilled in the art.

The pharmaceutical composition according to an embodiment, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories.

The pharmaceutical composition may contain from 0.1% to 99% by weight, of the active material, depending on the method of administration. The dose of the compound used in the treatment of the aforementioned conditions or disorders will vary in the usual way with the seriousness of the conditions or disorders, the weight of the subject, and other similar factors. However, as a general guide suitable unit doses may be 0.05 to 5000 mg, 1.0 to 500 mg or 1.0 to 200 mg and such unit doses may be administered more than once a day, for example two or three times a day. Such therapy may extend for a number of weeks, months or years.

In one embodiment, the pharmaceutical composition is formulated into injectable or infusible solutions, or reconstitutable powders.

In one embodiment, the pharmaceutical composition is adapted for oral formulation.

Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavorings or colorants, buffer salts and sweetening agents as appropriate. Preparations for oral administration may be suitably formulated to give controlled release of the active compound.

For parenteral administration, fluid unit dosage forms are prepared utilizing a compound of the invention or pharmaceutically acceptable salt thereof and a sterile vehicle. Formulations for injection may be presented in unit dosage form e.g. in ampoules or in multi-dose, utilizing a compound of the invention or pharmaceutically acceptable salt thereof and a sterile vehicle, optionally with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilized before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilizing agents, dispersing agents, suspending agents, thickening agents, or coloring agents. Drops may be formulated with an aqueous or non-aqueous base also comprising one or more dispersing agents, stabilizing agents, solubilizing agents or suspending agents. They may also contain a preservative.

The pharmaceutical composition may also be formulated in rectal compositions such as suppositories or retention enemas, e.g. containing conventional suppository bases such as cocoa butter or other glycerides.

The pharmaceutical composition may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unitary dose device or alternatively as a powder mix with a suitable carrier for administration using a suitable delivery device. Thus compounds of formula (I) may be formulated for oral, buccal, parenteral, topical (including ophthalmic and nasal), depot or rectal administration or in a form suitable for administration by inhalation or insufflation (either through the mouth or nose).

The pharmaceutical composition may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilized components.

An aspect of the disclosure provides for a pharmaceutical composition for use in the treatment of pancreatitis which comprises a compound of formula 1, a pharmaceutically acceptable salt thereof, or a solvate thereof, and one or more pharmaceutically acceptable excipient or carrier. In an embodiment, the pancreatitis is acute pancreatitis.

Reference Preparation Example

The compound of chemical formula 1 can be prepared by following the procedure described in U.S. application Ser. No. 16/313,360, of which entire contents are incorporated herein by reference.

Reference Preparation Example 1: Preparation of (E)-5-(4-(2-(aziridin-1-yl)ethoxy)phenyl)-5-(4-bromophenyl)-4-phenylpent-4-en-1-ol hydrochloride salt (Compound 18t)

By employing the following reaction scheme, compound 18t was prepared:

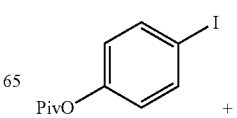

-continued

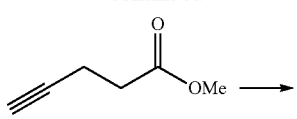

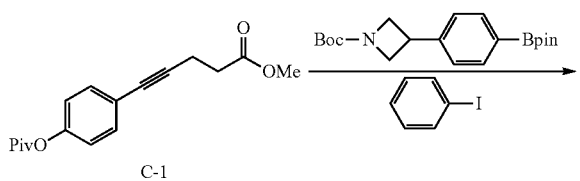

C-1

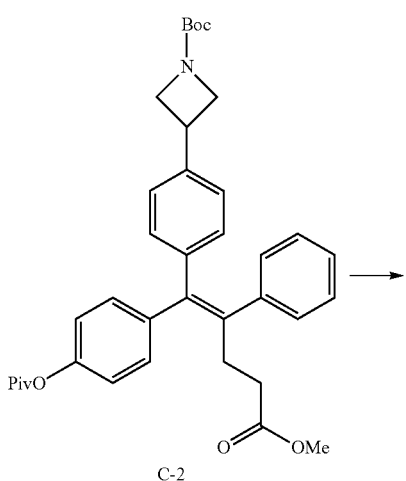

C-2

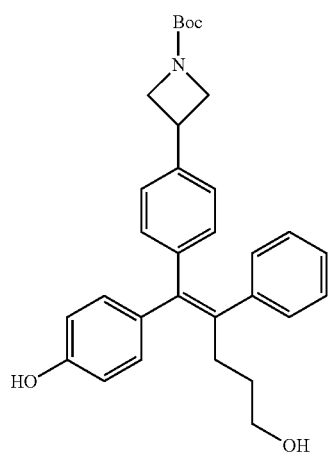

18t

Step 1: Preparation of methyl 5-(4-(pivaloyloxy) phenyl)pent-4-ynoate (C-1)

4-Iodophenyl pivalate (2 g, 6.6 mmol), copper (I) chloride (0.13 g, 0.66 mmol), bis(triphenylphosphine)palladium (II) dichloride ($PdCl_2(PPh_3)_2$, 0.23 g, 0.33 mmol), and methyl pent-4-ynoate (0.74 g, 0.66 mmol) were dissolved in trimethylamine (15 mL), and the reaction was carried out at 50° C. for 12 hours. The reaction solution was concentrated under reduced pressure, and 1.1 g of the desired compound C-1 (58%) was obtained using column chromatography.

Step 2: Preparation of (E)-tert-butyl 3-(4-(5-methoxy-5-oxo-2-phenyl-1-(4-(pivaloyloxy)phenyl) pent-1-en-1-yl)phenyl)azetidin-1-carboxylate (C-2)

tert-Butyl 3-(4-(4,4,5,5-tetramethyl-1,3,2-dioxaboran-2-yl)phenyl)azetidin-1-carboxylate (0.27 g, 0.75 mmol), compound C-1 (0.14 g, 0.5 mmol), and iodobenzene (84 μL, 0.75 mmol) were dissolved in DMF (8 mL) and water (4 mL), 0.025 M $PdCl_2(PhCN)_2$ (0.2 mL, 5 μmol) was added thereto, and heating was performed at 45° C. for 10 minutes. Cesium carbonate (0.24 g, 0.75 mmol) was added thereto, and heating was performed at 45° C. for 12 hours. When the reaction was completed, brine and ethyl acetate was further added to the reaction solution, and an organic layer was extracted. The organic layer was dried with anhydrous $Na_2SO_4$ and filtered. The solvent was distilled under reduced pressure to obtain a residue, which was purified using column chromatography, thereby obtaining 81 mg of the desired compound C-2 (27%).

Step 3: Preparation of tert-butyl (E)-3-(4-(5-hydroxy-1-(4-hydroxyphenyl)-2-phenylpent-1-en-1-yl) phenyl)azetidine-1-carboxylate (18t)

Compound C-2 (0.021 mmol) was added to tetrahydrofuran (2 mL), the temperature was lowered to 0° C., and 1 M lithium aluminum hydride, diisobutylaluminum hydride, or lithium borohydride (0.024 mL, 0.024 mmol) was added thereto. The temperature was raised to room temperature, and stirring was performed for 1 hour. Water and ethyl acetate were further added to the reaction solution and an organic layer was extracted. The organic layer was dried with anhydrous $Na_2SO_4$ and filtered. The solvent was distilled under reduced pressure to obtain a residue, which was purified using column chromatography and then dissolved in methanol:dichloromethane (1:1), the temperature was lowered to 0° C., a 1M aqueous HCl solution was slowly added thereto, and distillation under reduced pressure was performed, thereby obtaining 24 mg of the desired compound 18t (78%).

Reference Preparation Examples 2-3

Compounds 18a and 18t were prepared using the process of Reference Preparation Example 1. Identification data of the thus-prepared compounds 18a and 18t is shown in the following Table 1.

TABLE 1

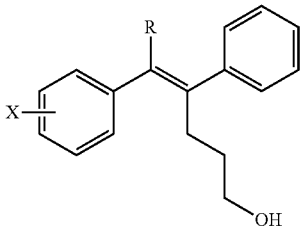

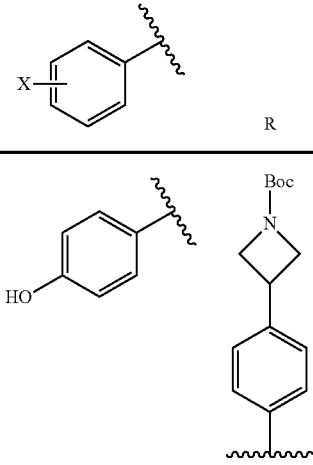

| Example | Cmpd No. | X | R | Identification data |
|---|---|---|---|---|
| 1 | 18t | 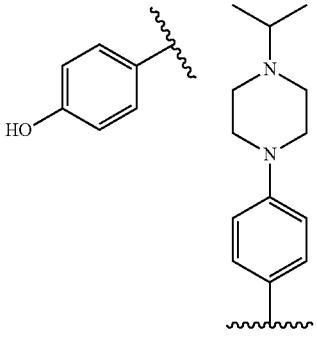 HO | Boc (azetidine with 4-phenyl substituent) | ¹H-NMR (CD₃OD, 400 MHz) δ 7.18-7.10 (m, 5H), 7.05 (d, J = 8.4 Hz, 2H), 6.98 (d, J = 8.2 Hz, 2H), 6.88 (d, J = 8.2 Hz, 2H), 6.79 (d, J = 8.4 Hz, 2H), 4.25 (t, J = 8.4 Hz, 2H), 3.81 (t, J = 6.6 Hz, 2H), 3.66 (m, 1H), 3.43 (t, J = 6.8 Hz, 2H), 2.55 (m, 2H), 1.57 (m, 2H), 1.45 (s, 9H). MS (ESI) m/z: 386 [M + H]⁺. |
| 2 | 18a | HO (4-hydroxyphenyl) | isopropyl-piperazine with 4-phenyl | ¹H-NMR (CD₃OD, 400 MHz) δ 7.14-7.07 (m, 5H), 7.02 (d, J = 8.0 Hz, 2H), 6.78 (m, 4H), 6.69 (d, J = 8.3 Hz, 2H), 3.76 (m, 2H), 3.52 (m, 3H), 3.41 (t, J = 6.4 Hz, 2H), 3.23 (m, 2H), 2.96 (m, 2H), 2.51 (m, 2H), 1.53 (m, 2H), 1.39 (d, J = 6.5 Hz, 6H). MS (ESI) m/z: 457 [M + H]⁺. |
| 3 | 18k | HO (3-hydroxyphenyl) | isopropyl-piperazine with 4-phenyl | ¹H-NMR (CD₃OD, 400 MHz) δ 7.19-7.09 (m, 6H), 6.81 (d, J = 8.7 Hz, 2H), 6.69 (m, 4H), 6.63 (m, 1H), 3.76 (m, 2H), 3.53 (m, 3H), 3.40 (t, J = 5.6 Hz, 2H), 3.21 (m, 2H), 2.91 (m, 2H), 2.50 (m, 2H), 1.53 (m, 2H), 1.38 (d, J = 6.6 Hz, 6H). MS (ESI) m/z: 457 [M + H]⁺. |

Reference Preparation Example 4

Preparation of (E)-4-(5-hydroxy-1-(4-(1-isopropylazetidin-3-yl)phenyl)-2-phenylpent-1-en-1-yl)phenol (Compound 22a)

By employing the following reaction scheme, compound 22a was prepared:

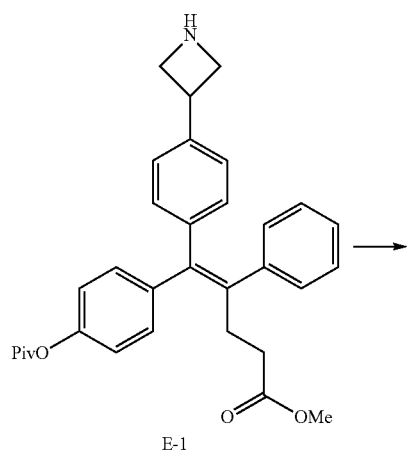

E-1

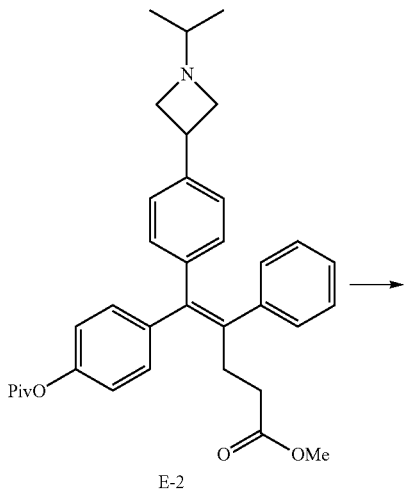

E-2

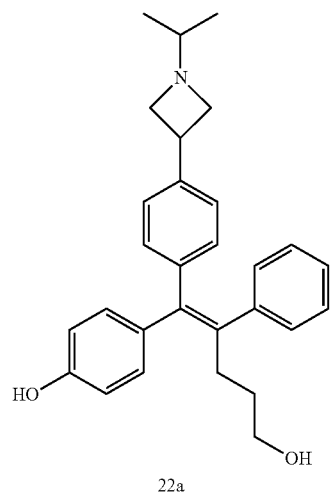

22a

Step 1: Preparation of methyl (E)-5-(4-(1-isopropylazetidin-3-yl)phenyl)-4-phenyl-5-(4-(pivaloyloxy)phenyl)pent-4-enoate (E-2)

Compound E-1 (0.03 g, 0.06 mmol), acetone (0.14 mL, 1.9 mmol), and sodium triacetoxyborohydride (NaBH(OAc)$_3$, 41 mg, 0.19 mmol) were added to dichloroethane (3 mL), and stirred at room temperature for 1 hour. Water and ethyl acetate were further added to the reaction solution and an organic layer was extracted. The organic layer was dried with anhydrous Na$_2$SO$_4$ and filtered. The solvent was distilled under reduced pressure to obtain a residue, which was purified using column chromatography, thereby obtaining 18 mg of the desired compound E-2 (54%).

Step 2: Preparation of (E)-4-(5-hydroxy-1-(4-(1-isopropylazetidin-3-yl)phenyl)-2-phenylpent-1-en-1-yl)phenol (22a)

4 mg of the desired compound 22a (27%) was obtained by the same process as step 3 of Example 4, using compound E-2.

Reference Preparation Examples 5-6

Compounds 22i and 22r e were prepared, using the process of Reference Preparation Example 4. Identification data of the thus-prepared compounds 22i and 22r is shown in the following Table 2.

TABLE 3
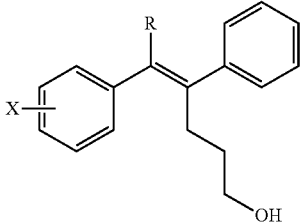
| Example | Cmpd No. | 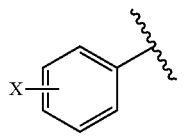 | R | Identification data |
|---|---|---|---|---|
| 4 | 22a | 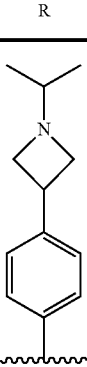 | 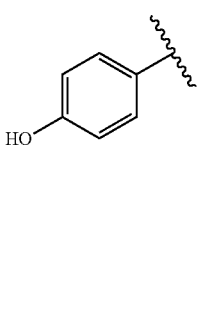 | ¹H-NMR (CD₃OD, 400 MHz) δ 7.17-7.08 (m, 5H), 7.08-7.02 (m, 4H), 6.94 (d, J = 8.2 Hz, 2H), 6.78 (d, J = 8.5 Hz, 2H), 4.38 (t, J = 8.3 Hz, 2H), 4.21 (m, 1H), 4.10 (t, J = 9.8 Hz, 2H), 3.98 (m, 1H), 3.43 (t, J = 7.5 Hz, 2H), 2.55 (m, 2H), 1.56 (m, 2H), 1.24 (d, J = 6.4 Hz, 6H). MS (ESI) m/z: 428 [M + H]⁺. |
| 5 | 22l | 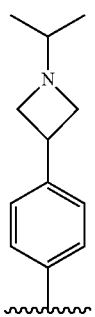 | 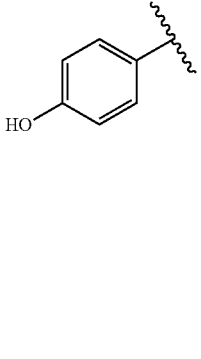 [SMILES: *c1ccc(O)cc1] | 1H-NMR (CD3OD, 400 MHz) δ 7.15-7.06 (m, 5H), 7.01 (d, J = 8.4 Hz, 2H), 6.90 (d, J = 8.2 Hz, 2H), 6.84 (d, J = 8.2 Hz, 2H), 6.75 (d, J = 8.5 Hz, 2H), 3.68 (m, 2H), 3.41 (t, J = 6.6 Hz, 2H), 3.24 (m, 2H), 2.79 (m, 2H), 2.52 (m, 2H), 2.02 (m, 2H), 1.78 (m, 2H), 1.54 (m, 2H), 0.97 (m, 4H). MS (ESI) m/z: 454 [M + H]+. |
| 6 | 22r | 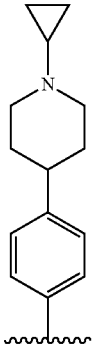 | 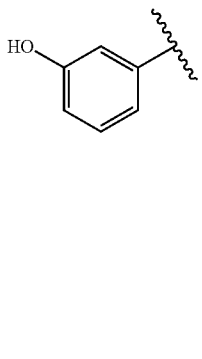 [SMILES: *c1cccc(O)c1] | ¹H-NMR (CD₃OD, 400 MHz) δ 7.21-7.10 (m, 7H), 6.90 (m, 4H), 6.72 (d, J = 7.9 Hz, 2H), 3.71 (m, 2H), 3.43 (t, J = 6.8 Hz, 2H), 3.27 (m, 2H), 2.80 (m, 2H), 2.52 (m, 2H), 2.01 (m, 2H), 1.79 (m, 2H), 1.52 (m, 2H), 0.98 (m, 4H). MS (ESI) m/z: 454 [M + H]⁺. |

Compounds 18a (DMRC200434), Compound 18k (DMRC2001000), Compound 22i (DMRC200699), and Compound 22r (DMRC200996), which were used in the Biological Examples, have the following structure.
Compounds 18a (DMRC200434)
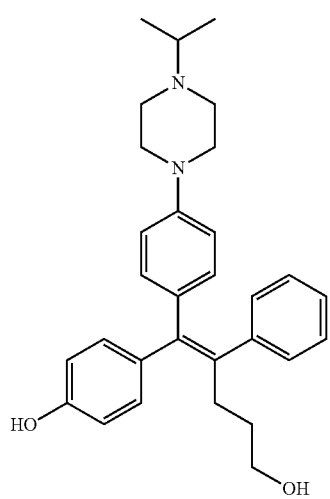
Compound 18k (=DMRC2001000)
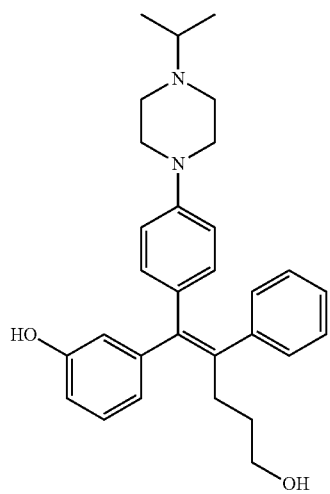
Compound 22i (DMRC200699)
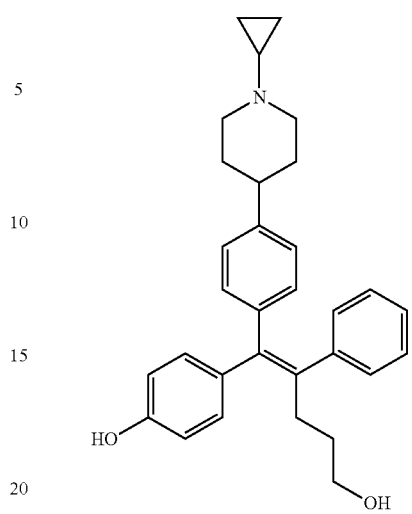
Compound 22r (DMRC200996)
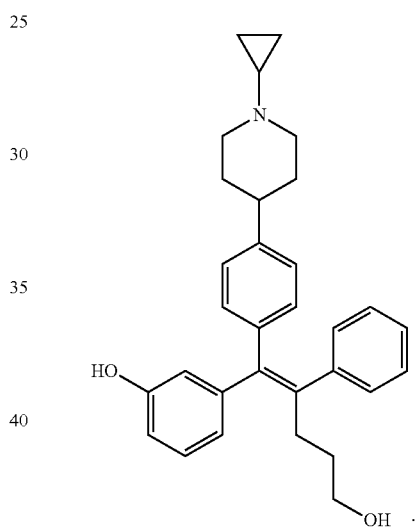
A reference compound GSK5182 has the following structure:
GSK5182
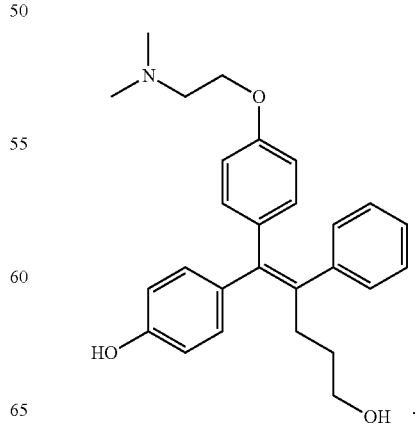

Biological Example 1

(A) Materials and Methods

Materials; Caerulein (C9026) and Taurolithocholic acid 3-sulfate disodium salt (TLCS; T0512) was purchased from Sigma.

Animal models; Eight to ten-week male C57BL/6 mice (Jackson Lab) were used according to an animal protocol approved by the Institutional Animal Care and Use Committee of Kyungpook National University.

1. Caerulein-Induced Model of Pancreatitis

Acute pancreatitis (AP) was induced by intraperitoneal injections of caerulein at 50 μg/kg/h given 6 times. As an ERRg antagonist, Compound DMRC 200434 (20 mg/kg) was dissolved in a solution of 5%—DMSO: 95%-20% PEG400(Saline) and was injected at two points—at 24 hours prior to, and at the start of the Caerulein treatment—and animals were sacrificed 16 hours after the last injection of Caerulein.

2. Intraductal Bile Acid Infusion Model of Pancreatitis

Pancreatitis was induced by retrograde infusion of the bile acid TLCS (1%) dissolved in saline into the distal common bile duct and pancreatic duct. Mice were anesthetized with a ketamine (120 mg/kg)/xylazine (12 mg/kg) mixture (Butler Schein, Chicago, Ill.). A ventral incision was made to reveal the abdominal cavity. The duodenum was flipped to reveal its distal side and held in place by ligatures. The bile duct was identified, and a 30-gauge needle was inserted through the antimesenteric aspect of the duodenum to cannulate the biliopancreatic duct. TLCS was infused at 10 μl/min for 5 min using a P33 perfusion pump (Harvard Apparatus, Holliston, Mass.). The exterior wound was closed using 7-mm wound clips, and a single injection of buprenorphine (0.075 mg/kg) was given immediately after the surgery. Normal saline-infused animals served as shams. Animals were allowed to recover on a heating pad for 90 min after the procedure. Mice were euthanized 24 h after induction.

Upon completion of experiments with above-mentioned animal models (1) and (2), pancreas tissue were snap frozen in liquid nitrogen and stored at −80° C. for analysis of trypsin activity, for protein analysis by Western blots and for gene expression analysis by RT-qPCR. Pancreas were dissected and fixed in 10% neutral-buffered formalin and embedded in paraffin. Five-μm sections were prepared and stained with hematoxylin and eosin (H&E). Pancreas injury was determined by measuring serum amylase (K711-100, Biovision), serum lipase (MAK046, Sigma) and pancreatic tissue trypsin activity (Biovision) was determined using commercially available kit.

Mouse Primary Acinar Cell Culture and Treatment.

Primary acinar cells were isolated from mice as described previously (*Isolation and Culture of Mouse Primary Pancreatic Acinar Cells*. Johann Gout, Roxane M. Pommier, David F. Vincent, Bastien Kaniewski, Sylvie Martel, Ulrich Valcourt, Laurent Bartholin. *J Vis Exp.* 2013 (78); 50514).

Western Blotting.

Cells were lysed in cell lysis buffer (Cell Signaling Technology, 9803) supplemented with protease inhibitor (Thermo Fisher Scientific, A32953) and phosphatase inhibitor (PhosSTOP™, Sigma Aldrich, 04906837001). Proteins were separated on 4-20% Mini-PROTEAN® TGX Precast Protein Gels by SDS PAGE electrophoresis and transferred to onto PVDF membranes (IPVH00010, EMD Millipore). Membranes were blocked in 5% BSA (Blotting-Grade Blocker, BioRad, 1706404) dissolved in TBS-T for 1 h and incubated overnight at 4° C. with primary antibody for ERRA (PP-H5844-00, R&D Systems) and ERRG (PP-H6812-00, R&D Systems). Membranes were washed three times with TBS-T and incubated with secondary antibodies for 1 h at room temperature: anti-mouse IgG, HRP-linked (Cell Signaling Technology, 7076). Images were obtained by Chemiluminescence buffer ECL (GE Healthcare) using a ChemiDoc™ (GE Healthcare).

Quantitative Reverse-Transcription PCR (RT-qPCR)

Total RNA was extracted using TRIzol® (Thermo Fisher Scientific) and, and then reversed transcribed using RevertAid™ First Strand cDNA Synthesis Kit (K1622Thermo Fisher Scientific) with oligo-dT primers. Quantitative PCR was performed with SYBR® Green Supermix (Bio-rad) on the ABI Prism 7300 sequence detection system (Applied Biosystems). The reaction conditions were as follows: predenaturation at 95° C. for 10 minutes and 40 cycles of denaturation at 95° C. for 15 s, annealing at 60° C. for 60 s, and extending at 72° C. for 1 minutes. The quantity of mRNA was calculated using the ΔCt method and normalized by the 36b4 (also known as Rplp0) house-keeping gene. Sequences for qPCR primers are as follows:

```
Esrra-forward:
                                    (SEQ ID NO: 1)
5'-TACGGTGTGGCATCCTGTGA Esrra-reverse:
                                    (SEQ ID NO: 2)
5'-CTCCCCTGGATGGTCCTCTT Esrrg-forward:
                                    (SEQ ID NO: 3)
5'-GCCCAGCCACGAATGAAT Esrrg-reverse:
                                    (SEQ ID NO: 4)
5'-GCAGGCCTGGCAGGATTT 36b4-forward:
                                    (SEQ ID NO: 5)
5'-ACCTCCTTCTTCCAGGCTTT 36b4-reverse:
                                    (SEQ ID NO: 6)
5'-CTCCAGTCTTTATCAGCTGC
```

(B) Results:

Upregulation of Esrrg in Caerulein-Treated Mouse Pancreas.

Figure 1B:
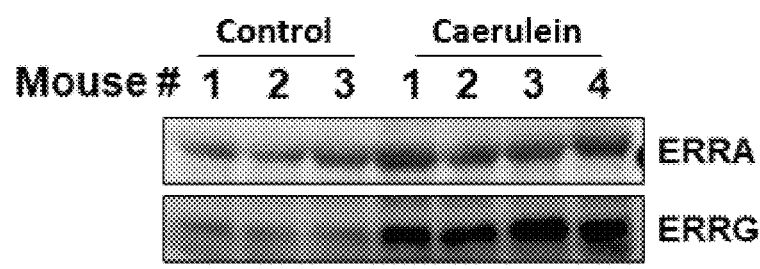
Figure 2A:
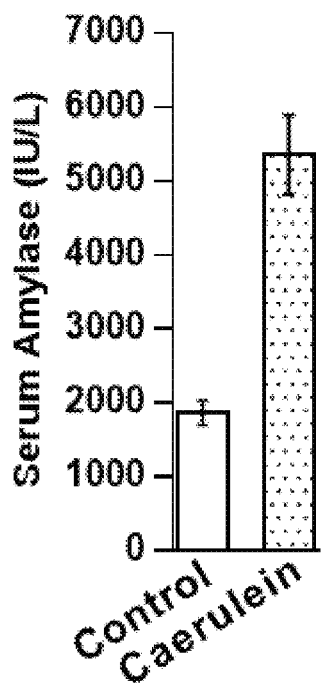
FIGS. 2A and 2B shows enhancement of serum amylase and lipase secretion in mice by Caerulein. Amylase level (FIG. 2A) or Lipase level (FIG. 2B) were measured in mice serum challenged with Caerulein or saline.
Figure 2B:
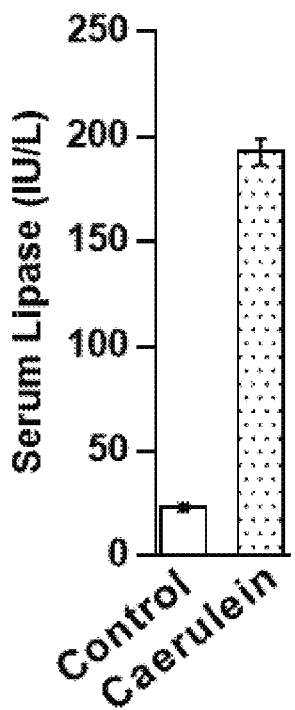

In contrast to Esrra mRNA expression pattern, Esrrg mRNA expression was highly increased in the pancreas of caerulein-challenged mouse when compared to control treatment (FIG. 1A). Immunoblotting confirmed that ERRG protein was highly increased upon caerulein-challenge in mouse pancreas (FIG. 1B). To analyze and confirm the extent of pancreatic injury upon caerulein-challenge, the inventors analyzed serum amylase and lipase levels in these animals. The inventors found that Caerulein treatment led to a dramatic upregulation in the amylase (FIG. 2A) and lipase (FIG. 2B) levels in the serum samples of these mice. These results indicated that pancreatic injury induced by caerulein can preferentially upregulated ERRG when compared to ERRA.

Reduction of Caerulein-Induced ERRG Protein Level in Mouse Pancreatic Acinar Cells.

Next, the inventors synthesized several compounds of Chemical Formula 1 as potential ERRG inhibitors and analyzed the toxicity of these compounds in vivo (Table 3).

Table 3 shows biochemical properties of Compounds 18a (DMRC200434), 18k (DMRC2001000), 22i (DMRC200699), and 22r (DMRC200996), and reference compound GSK5182.

TABLE 3

| Biochemistry of several ERRγ inverse agonist molecules. | | | | |
|---|---|---|---|---|
| | | GSK5182 | DMRC200434 | DMRC200699 |
| Binding Selectivity | ERRγ IC$_{50}$ (μM) | 0.110 | 0.040 | 0.056 |
| | ERRα IC$_{50}$ (μM) | >10 | >10 | >10 |
| | ERRβ IC$_{50}$ (μM) | >10 | 1.33 | 1.7 |
| | ERα IC$_{50}$ (μM) | 2 | 1.24 | 2.1 |
| ERRγ functional assay IC$_{50}$ (μM) | | 0.077 | 0.006 | 0.044 |
| Molecular Weight | | 417.6 | 456.6 | 453.6 |
| Water Solubility (mg/mL) | | >1 | >1 | >1 |
| In vitro safety | CYP (% remaining at 10 μM) | OK All >73% | OK All >64% | 1A2(57), 2C9(64), 2C19(32), 2D6(48), 3A4(54) |
| | hERG binding IC$_{50}$ (μM) | >30 | >10 | >30 |
| | hERG current IC$_{50}$ (μM) | — | 21.3 | 5.9 |
| | Ames (at 2 mM Max) | — | OK | OK |
| MS (% of control) | | H (43), d (10), r (26), m (7) | h (27), d (50), r (33), m (20) | h (36), d (92), r (92), m (84) |
| Plasma Stability (% of remaining after 2 h) | | — | h (92.1), r (97.1) | — |
| Permeability (PAMPA) (10$^{-6}$ cm/s) | | 0.11~0.82 | 0.46 | 0.35 |
| PK | po AUC (μMK) | 0.68 | 0.82 | 2.24 |
| | iv AUC (uMh) | 0.89 | 0.42 | 0.50 |
| | BA (%) | 8.4 | 22 | 46 |
| | Cmax (nM) | 130 | 208 | 380 |
| | CL (ml/min/kg) | 44 | 75 | 68 |
| | T½ (h) | 2.3 | 3.7 | 3.0 |
| | Vss (L/kg) | 9.1 | 16 | 12 |
| In vivo safety | Single dose Tox (mg/kg) | — | LD50 > 2000 | — |
| | Repeated dose Tox | — | Done | — |

| | | DMRC200966 | DMRC2001000 |
|---|---|---|---|
| Binding Selectivity | ERRγ IC$_{50}$ (μM) | 0.533 | 0.035 |
| | ERRα IC$_{50}$ (μM) | >10 | >10 |
| | ERRβ IC$_{50}$ (μM) | 3.1 | >10 |
| | ERα IC$_{50}$ (μM) | >10 | 1.94 |
| ERRγ functional assay IC$_{50}$ (μM) | | 0.134 | 0.020 |
| Molecular Weight | | 453.6 | 456.6 |
| Water Solubility (mg/mL) | | >1 | >1 |
| In vitro safety | CYP (% remaining at 10 μM) | OK All >83% | 1A2(100), 2C9(76), 2C19(100), 2D6(66), 3A4(48) |
| | hERG binding IC$_{50}$ (μM) | 17 | 25 |
| | hERG current IC$_{50}$ (μM) | >30 | >30 |
| | Ames (at 2 mM Max) | OK | OK |
| MS (% of control) | | h (62), d (57), r (50), m (25) | h (65), d (61), r (55), m (27) |
| Plasma Stability (% of remaining after 2 h) | | — | — |
| Permeability (PAMPA) (10$^{-6}$ cm/s) | | 0.014 | 1.29 |
| PK | po AUC (μMK) | 4.93 | 4.18 |
| | iv AUC (uMh) | 0.85 | 0.99 |
| | BA (%) | 58.2 | 42.4 |
| | Cmax (nM) | 1,510 | 970 |
| | CL (ml/min/kg) | 45 | 37 |
| | T½ (h) | 1.8 | 1.2 |
| | Vss (L/kg) | 4.6 | 3.0 |
| In vivo safety | Single dose Tox (mg/kg) | — | LD50 > 2000 |
| | Repeated dose Tox | — | Done |

Figure 3:
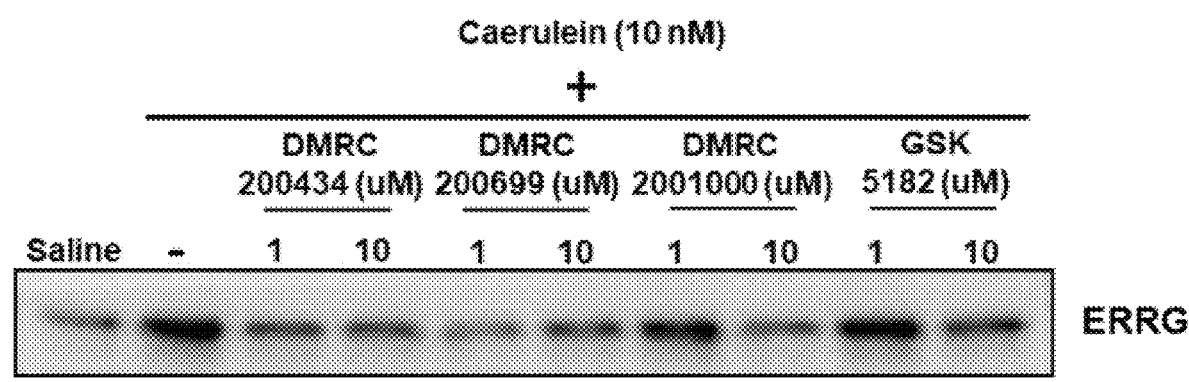
FIG. 3 shows a differential effect of ERRg inverse agonists on Caerulein-induced ERRg protein level in pancreatic acinar cells. Pancreatic acinar cells were isolated from mouse and stimulated with Caerulein (10 nM) for 16 hr in the absence or presence of indicated molecules. Protein extracts from these cells were subjected to SDS-PAGE and immunoblotted by anti-ERRg antibody.

To test the effectiveness of the compound of Chemical Formula 1 (DMRC200434, DMRC2001000, DMRC200699, and DMRC200996), and reference compound GSK5182 in vitro, the inventors isolated, harvested and cultured primary acinar cells from mouse and treated them with Caerulein for 16 hours in the absence or presence of these compounds (FIG. 3). Caerulein treatment led to marked increase in ERRG protein level in mouse primary acinar cells as demonstrated by immunoblotting. It was found the compound of Chemical Formula 1 which has ERRG antagonistic activity, showed activity. In particular Compound DMRC200434 showed strongest inhibitory effect on caerulein-induced ERRG protein level at a very low dose. This result indicated that DMRC200434 can be a potential candidate to inhibit ERRG during pancreatic injury.

Preventive Effects on Pancreatic Injury-Induced Acute Pancreatitis.

Figure 4A:
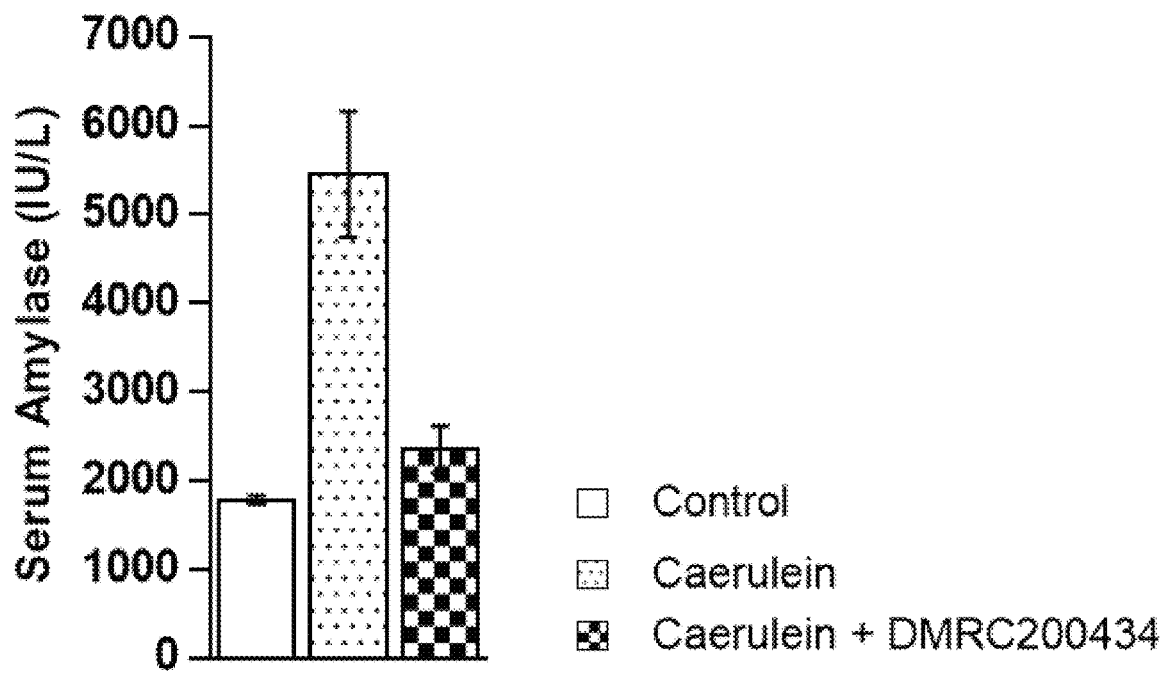
FIGS. 4A, 4B, 4C, and 4D show the activity of DMRC200434 molecule that rescues mice from Caerulein-induced acute pancreatitis. Mice were intraperitoneally injected with Caerulein in the absence or presence of compound DMRC200434 (20 mg/kg). Serum amylase (FIG. 4A), lipase levels (FIG. 4B) of these treated mice were indicated. Trypsin activity (FIG. 4C) in the pancreatic tissues of these treated mice were indicated. Hematoxylin-Eosin staining (FIG. 4D) was performed in the tissue sections of these treated mice as indicated.
Figure 4B:
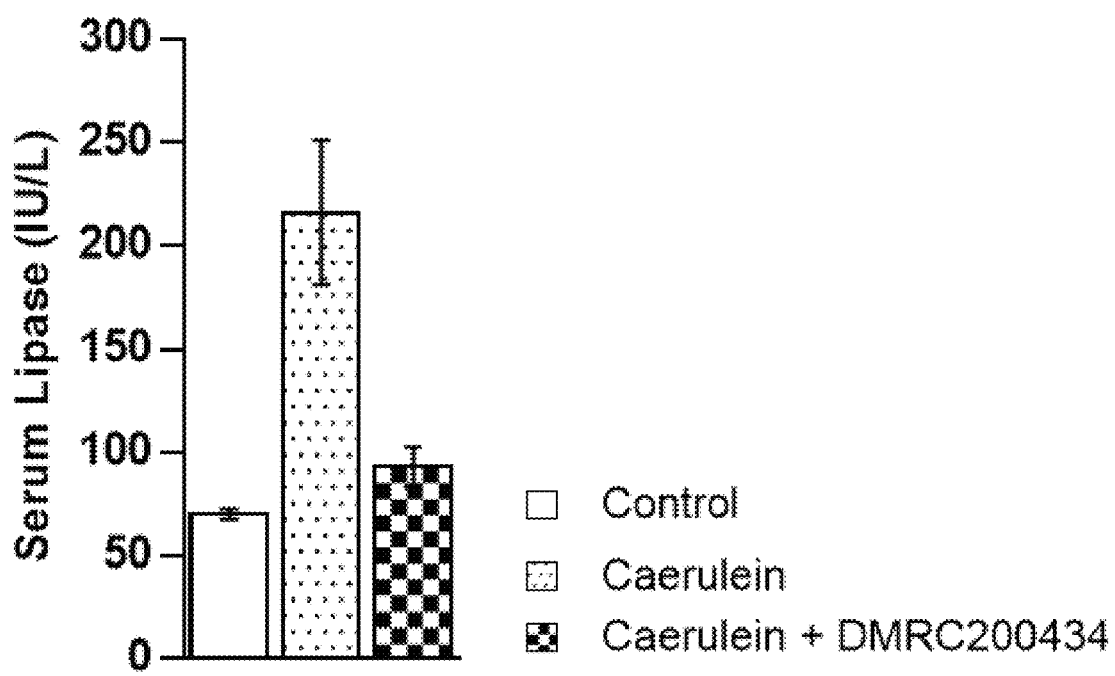
Figure 4C:
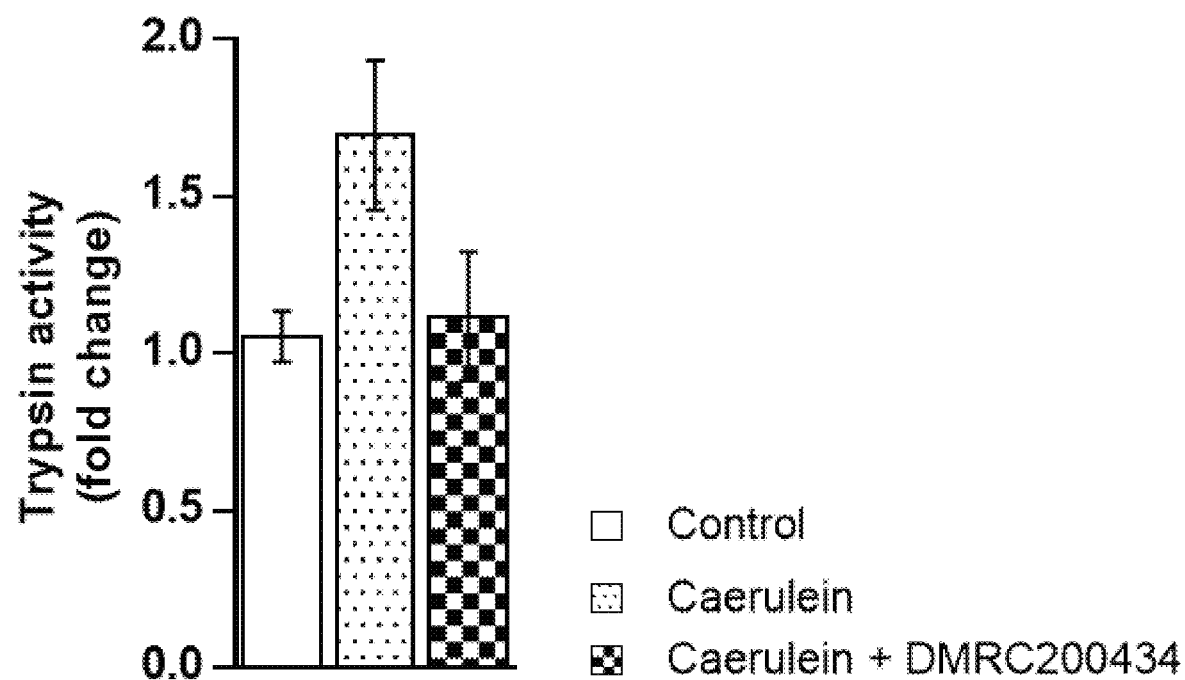
Figure 4D:
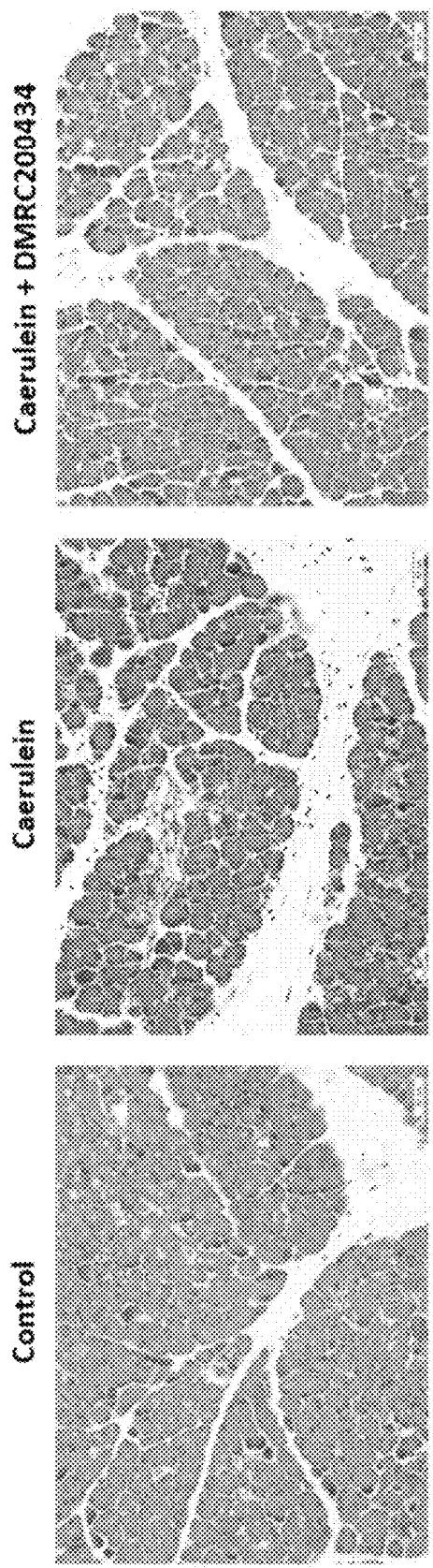

Next, the inventors analyzed the efficacy of the compound of Chemical Formula 1 in vivo using two different animal models of acute pancreatitis. Compound DMRC200434 was employed as compound of Chemical Formula 1. They pretreated mice with a single dose of DMRC200434, 24 hours prior to Caerulein challenge. An additional dose of DMRC200434 was administered to the animals at the beginning of Caerulein challenge. Upon completion of the experimental timeline, these animals were sacrificed and serum and pancreas tissue samples were collected and analyzed. The inventors found that when compared to Caerulein-challenge alone, mice treated with Caerulein in the presence of DMRC200434 showed a dramatic reduction in serum amylase (FIG. 4A), serum lipase (FIG. 4B) and tissue trypsin activity (FIG. 4C). The inventors further found that the pancreatic histopathology was dramatically improved in DMRC200434-treated mice, when compared to Caerulein-challenged mice alone (FIG. 4D). These results indicated that compound of Chemical Formula 1 (in particular DMRC200434) can protect against and ameliorate Caerulein-induced acute pancreatitis in vivo.

Figure 5A:
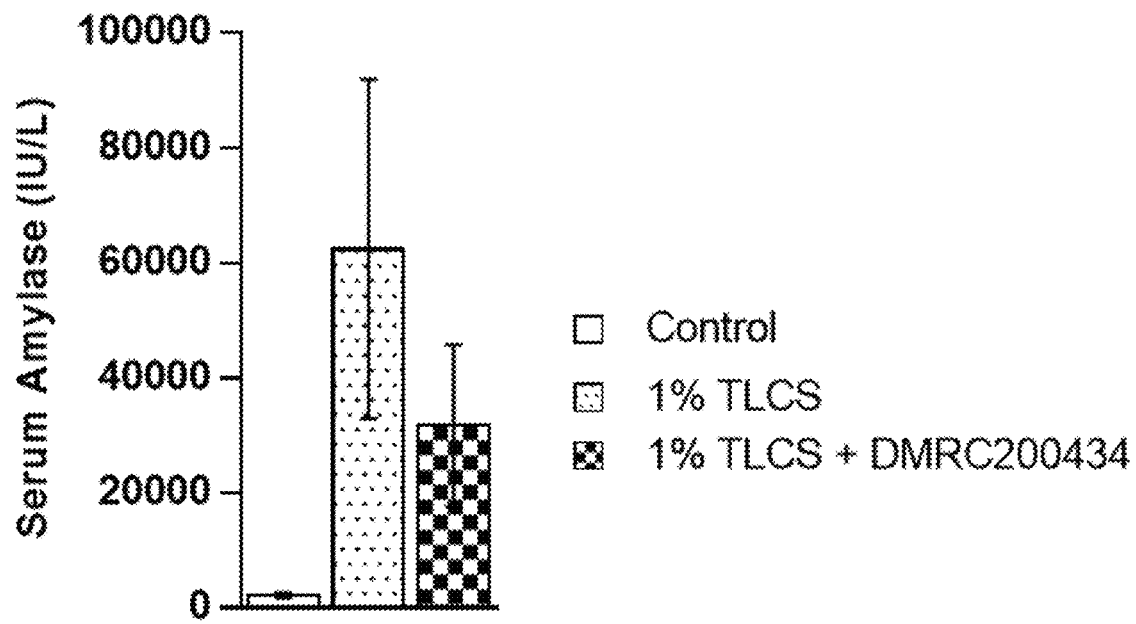
FIGS. 5A, 5B, and 5C show the activity of compound DMRC200434 molecule that rescues mice from Sodium Taurocholate-induced acute pancreatitis. Mice were intraperitoneally injected with Sodium taurocholate in the absence or presence of compound DMRC200434 (20 mg/kg). Serum amylase (FIG. 5A) and lipase levels (FIG. 5B) of these treated mice were indicated. Hematoxylin-Eosin staining (FIG. 5C) was performed in the tissue sections of these treated mice as indicated.
Figure 5B:
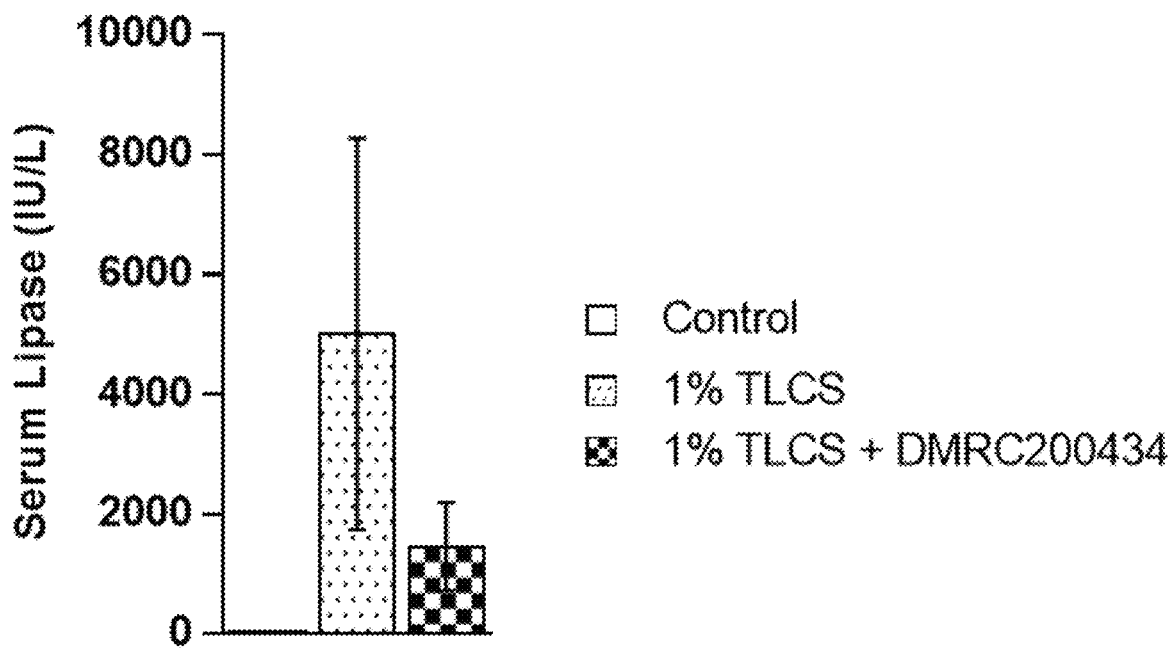
Figure 5C:
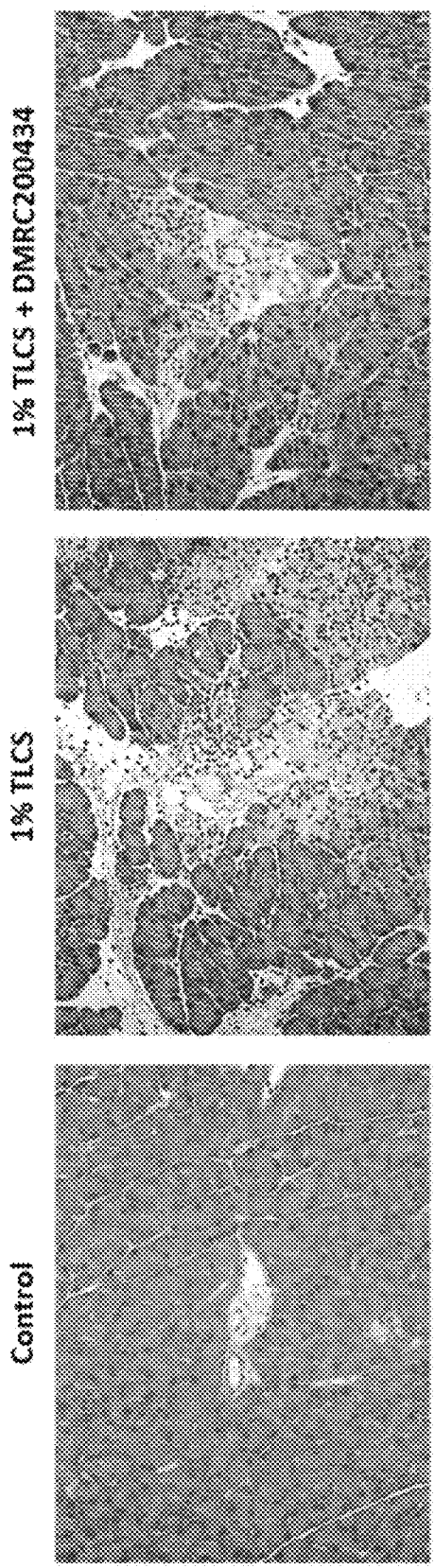

Additionally, the inventors assessed the efficacy of compound of Chemical Formula 1 using a different animal model of acute pancreatitis, viz., biliary pancreatitis which is a leading cause of acute pancreatitis in humans. The reflux of bile into the pancreatic duct is considered to be the cause of pancreatitis and this phenomenon was mimicked experimentally by challenging mice with TLCS. To that end, the inventors pretreated mice with a single dose of DMRC200434, 24 hours prior to TLCS challenge. An additional dose of DMRC200434 was administered to the animals at the beginning of TLCS challenge. Upon completion of the experimental timeline, these animals were sacrificed and serum and pancreas tissue samples were collected and analyzed. The inventors found that when compared to TLCS-challenge alone, mice treated with TLCS in the presence of DMRC200434 showed a dramatic reduction in serum amylase (FIG. 5A), serum lipase (FIG. 5B). The inventors further observed that the pancreatic histopathology was dramatically improved in DMRC200434-treated mice, when compared to TLCS-challenged mice alone (FIG. 5C).

These results indicated that compound of Chemical Formula 1, which shows an ERRg antagonistic activity can protect against TLCS-induced acute pancreatitis in vivo and ameliorate pancreatic pathology in this condition. In particular DMRC200434 showed strongest activity for preventing and/or treating pancreatitis.

Hereinabove, although various aspects have been described in detail with reference to the exemplary embodiments, it will be apparent to those skilled in the art that various modifications and alterations may be made without departing from the scope and spirit of the present disclosure. It should be understood that these modifications and alterations fall within the scope defined by the following claims.

---

What is claimed is:

1. A method for treating and/or preventing pancreatitis in a subject in need thereof, comprising administering to the subject an effective amount of a compound, wherein the compound is selected from the following compounds:

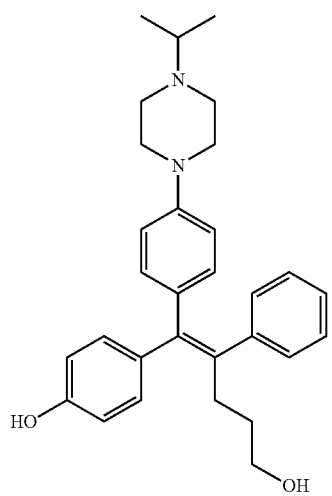 [SMILES: CC(C)N1CCN(c2ccc(/C(=C(/CCCO)c3ccccc3)c3ccc(O)cc3)cc2)CC1]

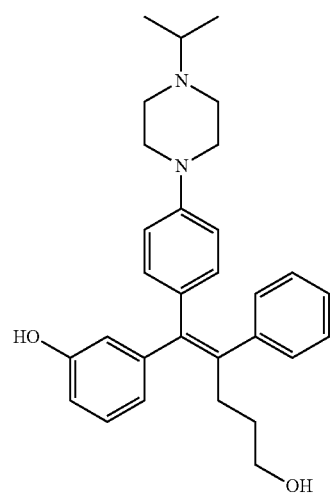 [SMILES: CC(C)N1CCN(c2ccc(/C(=C(/CCCO)c3ccccc3)c3cccc(O)c3)cc2)CC1]

-continued

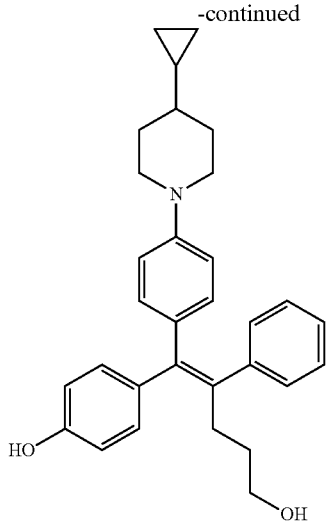

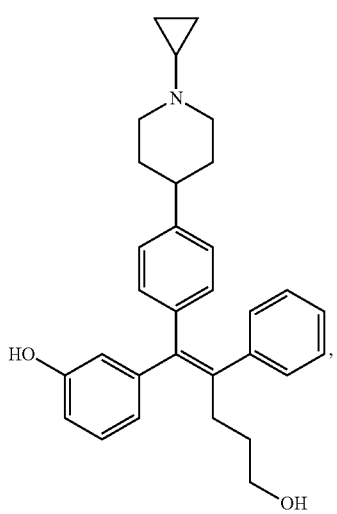

or an isomer, a pharmaceutically acceptable salt thereof, or a solvate thereof.

2. The method of claim 1, wherein the pancreatitis is acute pancreatitis.

3. The method of claim 1, wherein the subject is a mammal.

4. The method of claim 3, wherein the mammal is human.

5. The method of claim 1, wherein the compound is (E)-5-(4-hydroxyphenyl)-5-(4-(4-isopropylpiperazin-1-yl)phenyl)-4-phenylpent-4-en-1-ol of the following chemical formula:

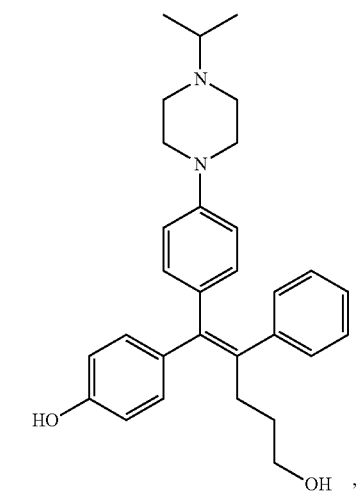 [SMILES: CC(C)N1CCN(c2ccc(/C(=C(/CCCO)c3ccccc3)c3ccc(O)cc3)cc2)CC1]

or an isomer, a pharmaceutically acceptable salt, or a solvate thereof.

6. A method for preventing and/or treating pancreatitis in a subject in need thereof, comprising administering an effective amount of (E)-5-(4-hydroxyphenyl)-5-(4-(4-isopropylpiperazin-1-yl)phenyl)-4-phenylpent-4-en-1-ol of the following chemical formula:

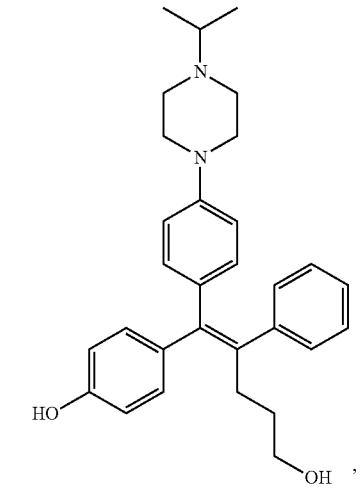 [SMILES: CC(C)N1CCN(c2ccc(/C(=C(/CCCO)c3ccccc3)c3ccc(O)cc3)cc2)CC1]

or a therapeutically acceptable salt thereof to the subject.

7. The method of claim 6, wherein the pancreatitis is acute pancreatitis.

* * * * *

UNITED STATES PATENT AND TRADEMARK OFFICE
CERTIFICATE OF CORRECTION

| | | |
|---|---|---|
| PATENT NO. | : 11,413,270 B2 | Page 1 of 1 |
| APPLICATION NO. | : 16/908195 | |
| DATED | : August 16, 2022 | |
| INVENTOR(S) | : Heon Jong Lee et al. | |

It is certified that error appears in the above-identified patent and that said Letters Patent is hereby corrected as shown below:

On the Title Page

Under (72) Inventors:
Add --Dipanjan CHANDA, Daegu (KR)--.

Signed and Sealed this
Twenty-second Day of November, 2022

Katherine Kelly Vidal
*Director of the United States Patent and Trademark Office*